US 9,498,390 B2

(12) United States Patent
Trennepohl et al.

(10) Patent No.: US 9,498,390 B2
(45) Date of Patent: Nov. 22, 2016

(54) METHOD OF CONSTRUCTING ABSORBENT ARTICLES COMPRISING GRAPHICS

(75) Inventors: Michael Dale Trennepohl, Cincinnati, OH (US); Andrew James Sauer, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 478 days.

(21) Appl. No.: 13/089,756

(22) Filed: Apr. 19, 2011

(65) Prior Publication Data

US 2011/0192011 A1    Aug. 11, 2011

Related U.S. Application Data

(63) Continuation of application No. 13/006,913, filed on Jan. 14, 2011, which is a continuation of application No. 11/999,229, filed on Dec. 4, 2007, now Pat. No. 7,896,858.

(60) Provisional application No. 60/872,697, filed on Dec. 4, 2006, provisional application No. 60/899,985, filed on Feb. 6, 2007.

(51) Int. Cl.
*A61F 13/15* (2006.01)
*B21D 39/00* (2006.01)
(Continued)

(52) U.S. Cl.
CPC ... *A61F 13/49014* (2013.01); *A61F 13/15699* (2013.01); *A61F 13/496* (2013.01);
(Continued)

(58) Field of Classification Search
CPC ............. Y10T 29/49885; A61F 13/42; A61F 13/8497; A61F 13/496; A61F 13/72; A61F 13/49011

USPC ...... 29/458; 101/483; 604/361, 367, 385.01, 604/396, 358
See application file for complete search history.

(56) References Cited

U.S. PATENT DOCUMENTS

| 364,029 A | 5/1887 | Macnab |
| 429,891 A | 6/1890 | Crowell |

(Continued)

FOREIGN PATENT DOCUMENTS

| DE | G 93 17 680.5 | 4/1995 |
| EP | 0 418 052 | 3/1991 |

(Continued)

OTHER PUBLICATIONS

"Pampers Ultra Trainers" package, Size 3 from Finneytown Kroger's dated Oct. 3, 1998.

(Continued)

*Primary Examiner* — Jermie Cozart
(74) *Attorney, Agent, or Firm* — Richard L. Alexander

(57) ABSTRACT

An absorbent article may comprise a first zone comprising graphics and a second zone comprising graphics, wherein the first and second zones have different elastic properties. Further, the absorbent article may comprise a first absorbent article component and a second absorbent article component having substantially different elastic properties, wherein the first absorbent article component comprises an elastomer. Additionally, the absorbent article may comprise a third absorbent article component overlapping the first and second absorbent article components, wherein the third absorbent article component comprises graphics on at least the portions which overlap the first and second absorbent article components.

28 Claims, 27 Drawing Sheets

(51) Int. Cl.
*A61F 13/49* (2006.01)
*A61F 13/496* (2006.01)
*A61F 13/514* (2006.01)
*A61F 13/72* (2006.01)
*A61F 13/84* (2006.01)

(52) U.S. Cl.
CPC ... *A61F13/49011* (2013.01); *A61F 13/51464* (2013.01); *A61F 13/51496* (2013.01); *A61F 13/72* (2013.01); *A61F 2013/8497* (2013.01); *Y10T 29/49826* (2015.01); *Y10T 29/49885* (2015.01)

(56) References Cited

U.S. PATENT DOCUMENTS

| | | |
|---|---|---|
| 1,639,218 A | 8/1927 | Ebersol |
| 2,075,189 A | 3/1937 | Galligan et al. |
| 2,111,613 A | 3/1938 | Bulford |
| 2,175,051 A | 10/1939 | Bromley |
| 2,378,444 A | 6/1945 | Smith et al. |
| 2,404,350 A | 7/1946 | Carlson et al. |
| 2,504,021 A | 4/1950 | Heinrich |
| 2,743,206 A | 4/1956 | Verduin |
| 3,306,194 A | 2/1967 | Cutri |
| 3,306,196 A | 2/1967 | Cutri |
| 3,442,211 A | 5/1969 | Beacham |
| 3,518,940 A | 7/1970 | Stroud et al. |
| 3,675,654 A | 7/1972 | Baker |
| 3,759,261 A | 9/1973 | Wang |
| 3,848,594 A | 11/1974 | Buell |
| 3,860,003 A | 1/1975 | Buell |
| 3,881,491 A | 5/1975 | Whyte |
| 3,911,173 A | 10/1975 | Sprague, Jr. |
| 3,921,232 A | 11/1975 | Whyte |
| 3,929,135 A | 12/1975 | Thompson |
| 3,978,789 A | 9/1976 | Fennekels et al. |
| 4,020,153 A | 4/1977 | Rowsell et al. |
| 4,022,210 A | 5/1977 | Glassman |
| 4,022,211 A | 5/1977 | Timmons |
| 4,032,661 A | 6/1977 | Rowsell et al. |
| 4,033,994 A | 7/1977 | Watson et al. |
| 4,034,109 A | 7/1977 | Rowsell et al. |
| 4,063,505 A | 12/1977 | Sasamoto et al. |
| 4,069,822 A | 1/1978 | Buell |
| 4,070,449 A | 1/1978 | Rowsell et al. |
| 4,070,496 A | 1/1978 | Rowsell et al. |
| 4,078,568 A | 3/1978 | Etes et al. |
| 4,089,765 A | 5/1978 | Dudley |
| 4,107,364 A | 8/1978 | Sisson |
| 4,140,115 A | 2/1979 | Schonfeld |
| 4,147,580 A | 4/1979 | Buell |
| 4,150,052 A | 4/1979 | Watson et al. |
| 4,153,679 A | 5/1979 | Rowsell et al. |
| 4,178,459 A | 12/1979 | Watson et al. |
| 4,192,311 A | 3/1980 | Felfoldi |
| 4,192,785 A | 3/1980 | Chen et al. |
| 4,193,936 A | 3/1980 | Watson et al. |
| 4,209,563 A | 6/1980 | Sisson |
| 4,218,973 A | 8/1980 | Bouffard et al. |
| 4,226,988 A | 10/1980 | Watson et al. |
| 4,227,531 A | 10/1980 | McLeod |
| 4,231,369 A | 11/1980 | Sorensen et al. |
| 4,231,370 A | 11/1980 | Mroz |
| 4,232,076 A | 11/1980 | Stetson et al. |
| 4,249,532 A | 2/1981 | Polansky et al. |
| 4,281,598 A | 8/1981 | Rump |
| 4,289,794 A | 9/1981 | Kleiner et al. |
| 4,292,916 A | 10/1981 | Bradley et al. |
| 4,296,093 A | 10/1981 | Rowsell et al. |
| 4,296,255 A | 10/1981 | Roswell et al. |
| 4,324,246 A | 4/1982 | Mullane et al. |
| 4,327,731 A | 5/1982 | Powell |
| 4,328,181 A | 5/1982 | Anders et al. |
| 4,340,212 A | 7/1982 | Simson |
| 4,342,314 A | 8/1982 | Radel et al. |
| 4,393,080 A | 7/1983 | Pawelchak et al. |
| 4,459,425 A | 7/1984 | Amano et al. |
| 4,463,045 A | 7/1984 | Ahr et al. |
| 4,501,072 A | 2/1985 | Jacobi, Jr. et al. |
| 4,505,976 A | 3/1985 | Doehnert et al. |
| 4,507,121 A | 3/1985 | Leung |
| 4,515,595 A | 5/1985 | Kievit et al. |
| 4,551,490 A | 11/1985 | Doyle et al. |
| 4,573,986 A | 3/1986 | Minetola et al. |
| 4,585,450 A | 4/1986 | Rosch et al. |
| D284,036 S | 6/1986 | Birring |
| 4,593,053 A | 6/1986 | Jevne et al. |
| 4,609,518 A | 9/1986 | Curro et al. |
| 4,609,587 A | 9/1986 | Giordano et al. |
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,663,220 A | 5/1987 | Wisneski et al. |
| 4,673,402 A | 6/1987 | Weisman et al. |
| 4,695,278 A | 9/1987 | Lawson |
| 4,699,146 A | 10/1987 | Sieverding |
| 4,699,622 A | 10/1987 | Toussant et al. |
| 4,704,116 A | 11/1987 | Enloe |
| 4,705,513 A | 11/1987 | Sheldon |
| 4,710,189 A | 12/1987 | Lash |
| 4,720,415 A | 1/1988 | Vander Wielen et al. |
| 4,738,257 A | 4/1988 | Meyer et al. |
| 4,785,996 A | 11/1988 | Ziecker et al. |
| 4,795,454 A | 1/1989 | Dragoo |
| 4,808,178 A | 2/1989 | Aziz et al. |
| 4,812,053 A | 3/1989 | Bhattacharjee |
| 4,816,025 A | 3/1989 | Foreman |
| 4,824,503 A | 4/1989 | Wilen |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,903,254 A | 2/1990 | Haas |
| 4,909,803 A | 3/1990 | Aziz et al. |
| 4,931,051 A | 6/1990 | Castello |
| 4,940,464 A | 7/1990 | Van Gompel et al. |
| 4,946,527 A | 8/1990 | Battrell |
| D310,880 S | 9/1990 | Majewski |
| 4,963,140 A | 10/1990 | Robertson et al. |
| 4,965,122 A | 10/1990 | Morman |
| 4,967,660 A | 11/1990 | Yamanari et al. |
| 4,968,312 A | 11/1990 | Khan |
| D313,076 S | 12/1990 | Harju |
| 4,980,705 A | 12/1990 | Akutsu et al. |
| 4,981,747 A | 1/1991 | Morman |
| 4,987,849 A | 1/1991 | Sherman |
| 4,990,147 A | 2/1991 | Freeland |
| 5,006,394 A | 4/1991 | Baird |
| 5,026,364 A | 6/1991 | Robertson |
| 5,037,416 A | 8/1991 | Allen et al. |
| 5,045,283 A | 9/1991 | Patel |
| 5,053,339 A | 10/1991 | Patel |
| 5,058,088 A | 10/1991 | Haas et al. |
| 5,062,840 A | 11/1991 | Holt et al. |
| 5,064,421 A | 11/1991 | Tracy |
| 5,086,700 A | 2/1992 | Van Den Berg |
| 5,092,861 A | 3/1992 | Nomura et al. |
| D325,256 S | 4/1992 | Landsman et al. |
| 5,114,781 A | 5/1992 | Morman |
| 5,116,662 A | 5/1992 | Morman |
| 5,124,188 A | 6/1992 | Roe et al. |
| 5,133,707 A | 7/1992 | Rogers et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| D330,590 S | 10/1992 | Pressley et al. |
| 5,156,793 A | 10/1992 | Buell et al. |
| D331,969 S | 12/1992 | Hunt |

(56) References Cited

U.S. PATENT DOCUMENTS

| | | |
|---|---|---|
| 5,167,653 A | 12/1992 | Igaue et al. |
| 5,167,655 A | 12/1992 | McCoy |
| 5,167,897 A | 12/1992 | Weber et al. |
| 5,171,236 A | 12/1992 | Dreier et al. |
| 5,178,139 A | 1/1993 | Angelillo et al. |
| D334,426 S | 3/1993 | Meis |
| 5,197,958 A | 3/1993 | Howell et al. |
| 5,214,442 A | 5/1993 | Roller |
| 5,221,274 A | 6/1993 | Buell et al. |
| 5,224,405 A | 7/1993 | Pohjola |
| 5,226,992 A | 7/1993 | Morman |
| 5,246,432 A | 9/1993 | Suzuki et al. |
| 5,246,433 A | 9/1993 | Hasse et al. |
| D341,197 S | 11/1993 | Patterson |
| 5,260,345 A | 11/1993 | Desmarais et al. |
| 5,266,592 A | 11/1993 | Grub et al. |
| 5,266,928 A | 11/1993 | Johnson |
| 5,269,775 A | 12/1993 | Freeland et al. |
| 5,275,103 A | 1/1994 | Hahne |
| 5,306,266 A | 4/1994 | Freeland |
| 5,318,555 A | 6/1994 | Siebers et al. |
| 5,320,891 A | 6/1994 | Levy et al. |
| 5,330,458 A | 7/1994 | Buell et al. |
| 5,330,459 A | 7/1994 | Lavon et al. |
| 5,336,545 A | 8/1994 | Morman |
| 5,342,338 A | 8/1994 | Roe |
| 5,342,343 A | 8/1994 | Kitaoka et al. |
| 5,348,750 A | 9/1994 | Greenberg |
| 5,358,500 A | 10/1994 | Lavon et al. |
| 5,359,525 A | 10/1994 | Weyenberg |
| H1376 H | 11/1994 | Osborn |
| 5,380,313 A | 1/1995 | Goulait et al. |
| 5,387,207 A | 2/1995 | Dyer et al. |
| 5,397,316 A | 3/1995 | Lavon et al. |
| 5,397,318 A | 3/1995 | Dreier et al. |
| 5,407,439 A | 4/1995 | Goulait |
| 5,425,726 A | 6/1995 | Shimizu et al. |
| 5,428,076 A | 6/1995 | Roe |
| 5,435,010 A | 7/1995 | May |
| 5,456,176 A | 10/1995 | Strasser |
| 5,458,590 A | 10/1995 | Schleinz et al. |
| 5,460,622 A | 10/1995 | Dragoo et al. |
| 5,468,236 A | 11/1995 | Everhart |
| 5,470,639 A | 11/1995 | Gessner et al. |
| 5,503,076 A | 4/1996 | Yeo |
| 5,509,915 A | 4/1996 | Hanson et al. |
| 5,514,121 A | 5/1996 | Roe et al. |
| 5,518,801 A | 5/1996 | Chappell et al. |
| 5,540,671 A | 7/1996 | Dreier |
| 5,540,673 A | 7/1996 | Thomas et al. |
| 5,540,976 A | 7/1996 | Shawver et al. |
| 5,542,942 A | 8/1996 | Kline et al. |
| 5,554,142 A | 9/1996 | Dreier et al. |
| 5,554,143 A | 9/1996 | Roe et al. |
| 5,554,145 A | 9/1996 | Roe et al. |
| 5,561,858 A | 10/1996 | Poirier |
| 5,567,609 A | 10/1996 | Sarras, Jr. et al. |
| 5,569,233 A | 10/1996 | Goulait |
| 5,569,234 A | 10/1996 | Buell et al. |
| 5,570,082 A | 10/1996 | Mahgerefteh et al. |
| 5,571,096 A | 11/1996 | Dobrin et al. |
| 5,580,411 A | 12/1996 | Nease et al. |
| 5,597,642 A | 1/1997 | Schleinz et al. |
| D377,980 S | 2/1997 | Slingland |
| 5,607,760 A | 3/1997 | Roe |
| 5,608,119 A | 3/1997 | Amano et al. |
| 5,609,587 A | 3/1997 | Roe |
| 5,612,118 A | 3/1997 | Schleinz et al. |
| 5,625,222 A | 4/1997 | Yoneda et al. |
| D379,226 S | 5/1997 | Kaczmarzyk et al. |
| 5,634,588 A | 6/1997 | Jørgensen-Beck et al. |
| 5,635,191 A | 6/1997 | Roe et al. |
| 5,635,290 A | 6/1997 | Stopper et al. |
| 5,643,588 A | 7/1997 | Roe et al. |
| 5,649,914 A | 7/1997 | Glaug et al. |
| 5,653,703 A | 8/1997 | Roe et al. |
| 5,658,268 A | 8/1997 | Johns et al. |
| 5,659,538 A | 8/1997 | Stuebe et al. |
| 5,662,637 A | 9/1997 | Kitaoka et al. |
| 5,667,609 A | 9/1997 | Liu |
| 5,669,900 A | 9/1997 | Bullwinkel et al. |
| 5,681,298 A | 10/1997 | Brunner et al. |
| 5,690,624 A | 11/1997 | Sasaki et al. |
| 5,702,376 A | 12/1997 | Glaug et al. |
| H1732 H | 6/1998 | Johnson |
| 5,766,212 A | 6/1998 | Jitoe |
| 5,766,389 A | 6/1998 | Brandon et al. |
| 5,779,831 A | 7/1998 | Schmitz |
| 5,790,035 A | 8/1998 | Ho |
| 5,797,892 A | 8/1998 | Glaug et al. |
| 5,800,416 A | 9/1998 | Seger et al. |
| 5,818,719 A | 10/1998 | Brandon et al. |
| 5,851,204 A | 12/1998 | Mizutani et al. |
| 5,865,823 A | 2/1999 | Curro |
| 5,883,028 A | 3/1999 | Morman et al. |
| 5,885,264 A | 3/1999 | Matsushita |
| 5,891,124 A | 4/1999 | Nomura et al. |
| 5,897,541 A | 4/1999 | Uitenbroek et al. |
| 5,897,545 A | 4/1999 | Kline et al. |
| 5,938,648 A | 8/1999 | Lavon et al. |
| 5,941,864 A | 8/1999 | Roe |
| D414,262 S | 9/1999 | Ashton et al. |
| 5,947,947 A | 9/1999 | Tanzer et al. |
| 5,957,908 A | 9/1999 | Kline et al. |
| 5,959,535 A | 9/1999 | Remsburg |
| 5,968,025 A | 10/1999 | Roe et al. |
| 5,977,430 A | 11/1999 | Roe et al. |
| 5,980,087 A | 11/1999 | Brandon et al. |
| 5,989,380 A | 11/1999 | Frischer |
| 5,997,520 A | 12/1999 | Ahr et al. |
| 5,997,989 A | 12/1999 | Gessner et al. |
| 6,001,460 A | 12/1999 | Morman et al. |
| 6,004,306 A | 12/1999 | Robles et al. |
| 6,010,490 A | 1/2000 | Freeland et al. |
| 6,013,063 A | 1/2000 | Roe et al. |
| 6,015,764 A | 1/2000 | Mccormack et al. |
| 6,017,537 A | 1/2000 | Alexander et al. |
| 6,033,502 A | 3/2000 | Coenen et al. |
| 6,045,543 A | 4/2000 | Pozniak et al. |
| 6,075,178 A | 6/2000 | La Wilhelm |
| 6,092,002 A | 7/2000 | Kastman et al. |
| 6,096,668 A | 8/2000 | Abuto et al. |
| 6,103,647 A | 8/2000 | Shultz et al. |
| 6,107,535 A | 8/2000 | Rossini et al. |
| 6,107,537 A | 8/2000 | Elder et al. |
| 6,113,717 A | 9/2000 | Vogt et al. |
| 6,114,597 A | 9/2000 | Romare |
| 6,118,041 A | 9/2000 | Roe et al. |
| 6,120,487 A | 9/2000 | Ashton |
| 6,120,488 A | 9/2000 | VanRijswijck et al. |
| 6,120,489 A | 9/2000 | Johnson et al. |
| 6,120,783 A | 9/2000 | Roe et al. |
| 6,123,694 A | 9/2000 | Pieniak et al. |
| 6,146,367 A | 11/2000 | Otsubo et al. |
| 6,153,209 A | 11/2000 | Vega et al. |
| 6,156,024 A | 12/2000 | Schulte et al. |
| 6,156,424 A | 12/2000 | Taylor |
| 6,166,285 A | 12/2000 | Schulte et al. |
| 6,168,584 B1 | 1/2001 | Allen et al. |
| 6,169,225 B1 | 1/2001 | Otsubo |
| 6,186,991 B1 | 2/2001 | Roe et al. |
| 6,214,788 B1 | 4/2001 | Velazco et al. |
| 6,224,699 B1 | 5/2001 | Bett et al. |
| 6,225,243 B1 | 5/2001 | Austin |
| 6,229,063 B1 | 5/2001 | Shimoe et al. |
| 6,245,168 B1 | 6/2001 | Coenen et al. |
| 6,253,159 B1 | 6/2001 | Bett et al. |
| 6,264,641 B1 | 7/2001 | Van Gompel et al. |
| 6,264,643 B1 | 7/2001 | Toyoda |
| 6,266,436 B1 | 7/2001 | Bett et al. |
| 6,267,974 B1 | 7/2001 | Suares et al. |
| 6,280,428 B1 | 8/2001 | Lash et al. |
| 6,297,424 B1 | 10/2001 | Olson |
| 6,297,434 B1 | 10/2001 | Martello |

(56) References Cited

U.S. PATENT DOCUMENTS

| | | |
|---|---|---|
| 6,307,119 B1 | 10/2001 | Cammarota |
| 6,313,372 B1 | 11/2001 | Suzuki |
| 6,320,096 B1 | 11/2001 | Inoue et al. |
| 6,328,982 B1 | 12/2001 | Shiroyama et al. |
| 6,348,253 B1 | 2/2002 | Daley et al. |
| 6,352,528 B1 | 3/2002 | Weber et al. |
| 6,359,168 B1 | 3/2002 | Frerot et al. |
| 6,384,728 B1 | 5/2002 | Kanor et al. |
| 6,428,526 B1 | 8/2002 | Heindel et al. |
| 6,429,526 B1 | 8/2002 | Blalock et al. |
| 6,432,098 B1 | 8/2002 | Kline et al. |
| 6,443,940 B1 | 9/2002 | Ashton et al. |
| 6,444,064 B1 | 9/2002 | Henry et al. |
| 6,448,467 B1 | 9/2002 | Herrlein et al. |
| 6,465,073 B1 | 10/2002 | Morman et al. |
| 6,478,786 B1 | 11/2002 | Glaug et al. |
| 6,479,154 B1 | 11/2002 | Walton et al. |
| 6,482,191 B1 | 11/2002 | Roe et al. |
| 6,497,032 B2 | 12/2002 | Maxton et al. |
| 6,503,236 B1 | 1/2003 | Uitenbroek et al. |
| 6,548,431 B1 | 4/2003 | Bansal et al. |
| 6,548,432 B1 | 4/2003 | Bansal et al. |
| 6,569,136 B1 | 5/2003 | Tao et al. |
| 6,576,810 B1 | 6/2003 | Underhill et al. |
| 6,579,274 B1 | 6/2003 | Morman et al. |
| 6,583,722 B2 | 6/2003 | Jeutter et al. |
| 6,590,136 B1 | 7/2003 | Young et al. |
| 6,592,884 B2 | 7/2003 | Hofmann et al. |
| 6,596,918 B1 | 7/2003 | Wehrle |
| 6,617,016 B2 | 9/2003 | Zhang et al. |
| 6,623,465 B1 | 9/2003 | Roe et al. |
| 6,623,837 B2 | 9/2003 | Morman et al. |
| 6,626,879 B1 | 9/2003 | Ashton et al. |
| 6,627,564 B1 | 9/2003 | Morman et al. |
| 6,627,786 B2 | 9/2003 | Roe et al. |
| 6,635,797 B2 | 10/2003 | Olson et al. |
| 6,642,427 B2 | 11/2003 | Roe et al. |
| 6,648,869 B1 | 11/2003 | Gillies et al. |
| 6,649,808 B1 | 11/2003 | Tao et al. |
| 6,657,100 B1 | 12/2003 | Underhill et al. |
| 6,676,646 B2 | 1/2004 | Bast et al. |
| 6,680,265 B1 | 1/2004 | Smith et al. |
| 6,680,422 B2 | 1/2004 | Roe |
| 6,692,475 B2 | 2/2004 | Mishima |
| 6,702,795 B2 | 3/2004 | Klemp |
| 6,710,221 B1 | 3/2004 | Pierce |
| 6,716,441 B1 | 4/2004 | Osborne et al. |
| 6,719,742 B1 | 4/2004 | Mccormack et al. |
| 6,726,668 B2 | 4/2004 | Underhill et al. |
| 6,727,404 B2 | 4/2004 | Ruman et al. |
| 6,733,483 B2 | 5/2004 | Raufman et al. |
| 6,743,314 B2 | 6/2004 | Henry et al. |
| 6,766,817 B2 | 7/2004 | Da Silva |
| 6,770,064 B1 | 8/2004 | Ruscher |
| 6,772,708 B2 | 8/2004 | Klofta |
| 6,811,865 B2 | 11/2004 | Morman et al. |
| 6,849,324 B2 | 2/2005 | Meece et al. |
| 6,870,479 B2 | 3/2005 | Gabriel |
| 6,875,710 B2 | 4/2005 | Eaton et al. |
| 6,881,206 B2 | 4/2005 | Underhill et al. |
| 6,884,906 B2 | 4/2005 | Dewis et al. |
| 6,904,865 B2 | 6/2005 | Klofta et al. |
| 6,905,488 B2 | 6/2005 | Olson |
| 6,909,028 B1 | 6/2005 | Shawver et al. |
| 6,918,404 B2 | 7/2005 | Da Silva |
| 6,929,819 B2 | 8/2005 | Underhill et al. |
| 6,942,894 B2 | 9/2005 | Alberg et al. |
| 6,943,894 B2 | 9/2005 | Kitahara |
| 6,949,689 B2 | 9/2005 | Noda et al. |
| 6,955,733 B2 | 10/2005 | Miller et al. |
| 6,957,160 B2 | 10/2005 | Miller et al. |
| 6,958,432 B2 | 10/2005 | Underhill et al. |
| 6,960,834 B2 | 11/2005 | Nakamura et al. |
| 6,996,851 B2 | 2/2006 | Nordness et al. |
| 7,002,055 B2 | 2/2006 | Long et al. |
| 7,033,341 B2 | 4/2006 | Mishima |
| 7,056,411 B2 | 6/2006 | Desai et al. |
| 7,066,586 B2 | 6/2006 | Da Silva |
| 7,123,981 B2 | 10/2006 | Dollevoet et al. |
| 7,169,137 B2 | 1/2007 | Shimada |
| 7,195,729 B2 | 3/2007 | Jackson et al. |
| 7,205,041 B2 | 4/2007 | Nair et al. |
| 7,223,818 B2 | 5/2007 | Autran et al. |
| 7,285,255 B2 | 10/2007 | Kadlec et al. |
| 7,301,036 B2 | 11/2007 | Parmee et al. |
| D583,935 S | 12/2008 | Sasayama et al. |
| 7,520,873 B2 | 4/2009 | Sosalla et al. |
| 7,678,094 B1 | 3/2010 | Cannon et al. |
| 7,718,844 B2 | 5/2010 | Olson |
| 7,806,880 B2 | 10/2010 | Roe et al. |
| D629,890 S | 12/2010 | Hedbratt et al. |
| 7,887,522 B2 | 2/2011 | Roe et al. |
| 7,896,858 B2 | 3/2011 | Trennepohl et al. |
| 7,901,390 B1 | 3/2011 | Ashton et al. |
| 8,182,457 B2 | 5/2012 | Olson et al. |
| 8,231,590 B2 | 7/2012 | Zander et al. |
| 2001/0031954 A1 | 10/2001 | Jordan |
| 2002/0019616 A1 | 2/2002 | Thomas |
| 2002/0062117 A1 | 5/2002 | Raufman et al. |
| 2002/0072728 A1 | 6/2002 | Shinohara et al. |
| 2002/0111596 A1 | 8/2002 | Fletcher et al. |
| 2002/0138062 A1 | 9/2002 | Kuen et al. |
| 2003/0028165 A1 | 2/2003 | Curro et al. |
| 2003/0060794 A1 | 3/2003 | Olson |
| 2003/0065298 A1 | 4/2003 | Krishnaswamy et al. |
| 2003/0073966 A1 | 4/2003 | Sosalla |
| 2003/0077430 A1 | 4/2003 | Grimm et al. |
| 2003/0087059 A1 | 5/2003 | Jackson et al. |
| 2003/0088220 A1 | 5/2003 | Molander et al. |
| 2003/0091807 A1 | 5/2003 | Desai et al. |
| 2003/0114807 A1 | 6/2003 | Underhill et al. |
| 2003/0114821 A1 | 6/2003 | Underhill et al. |
| 2003/0120240 A1 | 6/2003 | Buell et al. |
| 2003/0120254 A1 | 6/2003 | Franke et al. |
| 2003/0125682 A1 | 7/2003 | Olson et al. |
| 2003/0125689 A1 | 7/2003 | Olson et al. |
| 2003/0145937 A1 | 8/2003 | Underhill et al. |
| 2003/0158532 A1 | 8/2003 | Magee |
| 2003/0158534 A1 | 8/2003 | Niki et al. |
| 2003/0162458 A1 | 8/2003 | Tsujiyama et al. |
| 2003/0167049 A1 | 9/2003 | Gibbs |
| 2003/0193113 A1 | 10/2003 | Glovatsky |
| 2003/0199845 A1 | 10/2003 | Roe et al. |
| 2003/0233082 A1 | 12/2003 | Kline et al. |
| 2004/0019343 A1 | 1/2004 | Olson et al. |
| 2004/0030310 A1 | 2/2004 | Roe et al. |
| 2004/0064113 A1 | 4/2004 | Erdman |
| 2004/0067970 A1 | 4/2004 | Foster et al. |
| 2004/0071780 A1 | 4/2004 | Lillard et al. |
| 2004/0081680 A1 | 4/2004 | Pesce et al. |
| 2004/0082654 A1 | 4/2004 | Pesce et al. |
| 2004/0092902 A1 | 5/2004 | Hoffman et al. |
| 2004/0097896 A1 | 5/2004 | Raufman et al. |
| 2004/0108043 A1 | 6/2004 | Otsubo |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0143231 A1 | 7/2004 | Nair et al. |
| 2004/0162536 A1 | 8/2004 | Becker et al. |
| 2004/0167486 A1 | 8/2004 | Busam et al. |
| 2004/0191118 A1 | 9/2004 | Mody |
| 2004/0191279 A1 | 9/2004 | Klofta |
| 2004/0193113 A1 | 9/2004 | Gillis et al. |
| 2004/0193133 A1 | 9/2004 | Desai et al. |
| 2004/0211696 A1 | 10/2004 | Underhill et al. |
| 2004/0220540 A1 | 11/2004 | Underhill et al. |
| 2004/0243083 A1 | 12/2004 | Matsuda et al. |
| 2004/0254549 A1 | 12/2004 | Olson et al. |
| 2004/0254550 A1 | 12/2004 | Huang et al. |
| 2005/0027274 A1 | 2/2005 | Suzuki et al. |
| 2005/0049553 A1 | 3/2005 | Triplett et al. |
| 2005/0049568 A1 | 3/2005 | Underhill et al. |
| 2005/0065489 A1 | 3/2005 | Driskell et al. |
| 2005/0070866 A1 | 3/2005 | Isele et al. |

(56) References Cited

U.S. PATENT DOCUMENTS

| | | | |
|---|---|---|---|
| 2005/0092427 A1 | 5/2005 | Vergona |
| 2005/0096612 A1 | 5/2005 | Davis et al. |
| 2005/0096618 A1 | 5/2005 | Magee et al. |
| 2005/0106980 A1 | 5/2005 | Abed et al. |
| 2005/0124952 A1 | 6/2005 | Zehner et al. |
| 2005/0125877 A1 | 6/2005 | Benjamin et al. |
| 2005/0125923 A1 | 6/2005 | Benjamin et al. |
| 2005/0129743 A1 | 6/2005 | Benjamin et al. |
| 2005/0139713 A1 | 6/2005 | Weber et al. |
| 2005/0147785 A1 | 7/2005 | Ahn et al. |
| 2005/0177123 A1 | 8/2005 | Catalan |
| 2005/0214461 A1 | 9/2005 | Desai et al. |
| 2005/0222546 A1 | 10/2005 | Vargo et al. |
| 2005/0228349 A1 | 10/2005 | Long et al. |
| 2005/0273071 A1 | 12/2005 | McKiernan et al. |
| 2006/0004333 A1 | 1/2006 | Olson |
| 2006/0020249 A1 | 1/2006 | Allen |
| 2006/0025737 A1 | 2/2006 | Song et al. |
| 2006/0068168 A1 | 3/2006 | Olson et al. |
| 2006/0069361 A1 | 3/2006 | Olson et al. |
| 2006/0069362 A1 | 3/2006 | Odorzynski et al. |
| 2006/0111686 A1 | 5/2006 | Schneider |
| 2006/0212010 A1 | 9/2006 | Roe et al. |
| 2006/0212018 A1 | 9/2006 | Roe et al. |
| 2006/0224132 A1 | 10/2006 | Roe et al. |
| 2006/0247594 A1 | 11/2006 | Nickel et al. |
| 2006/0247598 A1 | 11/2006 | Roehrl et al. |
| 2006/0264858 A1 | 11/2006 | Roe et al. |
| 2006/0293632 A1 | 12/2006 | Long et al. |
| 2007/0005035 A1 | 1/2007 | Snauwaert et al. |
| 2007/0032766 A1 | 2/2007 | Liu et al. |
| 2007/0049884 A1 | 3/2007 | Long et al. |
| 2007/0049889 A1 | 3/2007 | Larson et al. |
| 2007/0073261 A1 | 3/2007 | Ashton et al. |
| 2007/0083173 A1 | 4/2007 | Olson |
| 2007/0142800 A1 | 6/2007 | Liu |
| 2007/0191797 A1 | 8/2007 | Roe et al. |
| 2007/0233025 A1 | 10/2007 | Nishikawa et al. |
| 2007/0233026 A1 | 10/2007 | Roe et al. |
| 2007/0233027 A1 | 10/2007 | Roe et al. |
| 2007/0233028 A1 | 10/2007 | Roe et al. |
| 2007/0250023 A1 | 10/2007 | Strannemalm |
| 2007/0250406 A1 | 10/2007 | Mason et al. |
| 2007/0287348 A1 | 12/2007 | Autran et al. |
| 2007/0287971 A1 | 12/2007 | Roe et al. |
| 2007/0287982 A1 | 12/2007 | Lodge et al. |
| 2007/0287983 A1 | 12/2007 | Lodge et al. |
| 2008/0004585 A1 | 1/2008 | McCusker, III et al. |
| 2008/0087569 A1 | 4/2008 | Ponomarenko et al. |
| 2008/0091162 A1 | 4/2008 | Maldonado et al. |
| 2008/0108967 A1 | 5/2008 | Mizushima et al. |
| 2008/0167635 A1 | 7/2008 | Kline et al. |
| 2009/0030389 A1 | 1/2009 | Ashton et al. |
| 2009/0254058 A1 | 10/2009 | Shiriike et al. |
| 2010/0089264 A1 | 4/2010 | Warner |

FOREIGN PATENT DOCUMENTS

| | | |
|---|---|---|
| EP | 0 495 285 | 7/1992 |
| EP | 0 454 105 B1 | 11/1995 |
| EP | 0 547 497 B1 | 3/1997 |
| EP | 0 951 889 | 10/1999 |
| EP | 0 776 645 B1 | 3/2002 |
| EP | 1 216 673 A1 | 6/2002 |
| EP | 1 222 907 A2 | 7/2002 |
| EP | 1 287 799 A2 | 3/2003 |
| EP | 1 356 798 A1 | 10/2003 |
| EP | 0 937 446 B1 | 9/2004 |
| EP | 1 279 357 B1 | 9/2005 |
| EP | 1704842 | 9/2006 |
| GB | 177 977 | 2/1987 |
| JP | 56-043402 | 4/1981 |
| JP | 59-116317 | 7/1984 |
| JP | 02-140163 | 5/1990 |
| JP | 05-247701 | 9/1993 |
| JP | 11-104172 | 4/1999 |
| JP | 2003-070838 | 8/2001 |
| JP | 2003-070838 | 3/2003 |
| JP | 2003-111798 | 4/2003 |
| JP | 2005-296372 | 4/2004 |
| JP | 2004-141640 A | 5/2004 |
| JP | 2004-305761 | 11/2004 |
| WO | WO 94/13235 A1 | 6/1994 |
| WO | WO 94/14395 A1 | 7/1994 |
| WO | WO 95/16746 A1 | 6/1995 |
| WO | WO 96/10380 A2 | 4/1996 |
| WO | WO 99/20216 A1 | 4/1999 |
| WO | WO 99/22688 A1 | 5/1999 |
| WO | WO 00/00233 A1 | 1/2000 |
| WO | WO 00/15169 A1 | 3/2000 |
| WO | WO-00/27328 | 5/2000 |
| WO | WO 00/35401 A1 | 6/2000 |
| WO | WO 00/37006 A1 | 6/2000 |
| WO | WO 00/37009 | 6/2000 |
| WO | WO 00/76438 | 12/2000 |
| WO | WO 00/76439 | 12/2000 |
| WO | WO 00/76442 | 12/2000 |
| WO | WO 00/76443 | 12/2000 |
| WO | WO 01/21126 A1 | 3/2001 |
| WO | WO 01/41691 A1 | 6/2001 |
| WO | WO 01/95845 A1 | 12/2001 |
| WO | WO 02/49564 A1 | 6/2002 |
| WO | WO 02/091968 A2 | 11/2002 |
| WO | WO 03/034966 A1 | 5/2003 |
| WO | WO 2004/026206 A1 | 4/2004 |
| WO | WO 2004/028403 A2 | 4/2004 |
| WO | WO 2004/071780 A2 | 8/2004 |
| WO | WO 2005/037159 A | 4/2005 |
| WO | WO 2005/041834 A1 | 5/2005 |
| WO | WO 2005/102239 A1 | 11/2005 |
| WO | WO 2006/017518 A2 | 2/2006 |
| WO | WO 2006/017674 A1 | 2/2006 |
| WO | WO 2006/028911 A1 | 3/2006 |
| WO | WO 2006/127519 A2 | 11/2006 |
| WO | WO 2007/017817 A2 | 2/2007 |

OTHER PUBLICATIONS

Timothy R. Schum, MD, et al.—Sequential Acquisition of Toilet-Training Skills: A Descriptive Study of Gender and Age Differences in Normal Children, Pediatrics, Mar. 2002, 7 pages vol. 109, No. 3.
International Search Report, mailed Aug. 23, 2006, PCT/US2006/009302, 13 pages.
International Search Report, mailed Oct. 7, 2007, PCT/US2006/009303, 11 pages.
International Search Report, mailed Mar. 29, 2007, PCT/IB2006/052696, 10 pages.
International Search Report, mailed Sep. 10, 2008, PCT/US2007/007171, 7 pages.
International Search Report, mailed Oct. 30, 2007, PCT/US2007/007171, 11 pages.
International Search Report, mailed Jul. 30, 2008, PCT/US2007/024933, 22 pages.
International Search Report, mailed Jun. 11, 2006, PCT/US2006/019580, 17 pages.
PCT International Search Report, PCT/US2007/024933 dated Jun. 6, 2008.
Photos of Pampers Trainers pants and packages, Oct. 3, 1998.
U.S. Appl. No. 11/999,229, filed Dec. 4, 2007, All Office Actions and Responses begining May 20, 2010.
U.S. Appl. No. 11/372,449, filed Mar. 9, 2006, Reissue of U.S. 6,702,795.
All Office Actions, U.S. Appl. No. 11/999,229.
All Office Actions, U.S. Appl. No. 13/006,913.
All Office Actions, U.S. Appl. No. 13/089,690.
All Office Actions, U.S. Appl. No. 13/089,771.
All Office Actions, U.S. Appl. No. 13/101,568.
All Office Actions, U.S. Appl. No. 13/101,583.
All Office Actions, U.S. Appl. No. 13/101,588.
All Office Actions, U.S. Appl. No. 13/101,597.

(56) References Cited

OTHER PUBLICATIONS

All Office Actions, U.S. Appl. No. 13/101,621.
All Office Actions, U.S. Appl. No. 13/102,111.
All Office Actions, U.S. Appl. No. 13/102,115.
All Office Actions, U.S. Appl. No. 13/102,123.
All Office Actions, U.S. Appl. No. 13/102,127.
U.S. Appl. No. 13/101,621, filed May 5, 2011, Office Action dated Apr. 8, 2014.
U.S. Appl. No. 13/101,568, filed May 5, 2011, Office Action dated Mar. 10, 2014.
Non-Final Rejection for U.S. Appl. No. 13/006,913 dated Dec. 4, 2012.
Amendment for U.S. Appl. No. 13/006,913 dated Mar. 4, 2013.
Final Rejection for U.S. Appl. No. 13/006,913 dated Jun. 14, 2013.
RCE and Amendment for U.S. Appl. No. 13/006,913 dated Sep. 16, 2013.
Non-Final Rejection for U.S. Appl. No. 13/006,913 dated Sep. 30, 2013.
Amendment for U.S. Appl. No. 13/006,913 dated Dec. 19, 2013.
Final Rejection for U.S. Appl. No. 13/006,913 dated Jan. 15, 2014.
RCE and Amendment for U.S. Appl. No. 13/006,913 dated Jul. 14, 2014.
Non-Final rejection for U.S. Appl. No. 13/102,111 dated Nov. 20, 2012.
Amendment for U.S. Appl. No. 13/102,111 dated Feb. 20, 2013.
Final Rejection for U.S. Appl. No. 13/102,111 dated Jun. 13, 2013.
RCE and Amendment for U.S. Appl. No. 13/102,111 dated Oct. 10, 2013.
Non-Final Rejection for U.S. Appl. No. 13/102,111 dated Oct. 28, 2013.
Amendment for U.S. Appl. No. 13/102,111 dated Jan. 28, 2014.
Final Rejection for U.S. Appl. No. 13/102,111 dated Feb. 14, 2014.
RCE and Amendment for U.S. Appl. No. 13/102,111 dated Jul. 14, 2014.
Non-Final Rejection for U.S. Appl. No. 13/102,115 dated Nov. 21, 2012.
Amendment for U.S. Appl. No. 13/102,115 dated Feb. 21, 2013.
Final Rejection for U.S. Appl. No. 13/102,115 dated Jun. 18, 2013.
RCE and Amendment for U.S. Appl. No. 13/102,115 dated Sep. 16, 2013.
Non-Final Rejection for U.S. Appl. No. 13/102,115 dated Sep. 27, 2013.
Amendment for U.S. Appl. No. 13/102,115 dated Dec. 17, 2013.
Final Rejection for U.S. Appl. No. 13/102,115 dated Jan. 28, 2014.
RCE and Amendment for U.S. Appl. No. 13/102,115 dated Jun. 23, 2014.
Non-Final Rejection for U.S. Appl. No. 13/102,123 dated Nov. 21, 2012.
Amendment for U.S. Appl. No. 13/102,123 dated Feb. 21, 2013.
Final Rejection for U.S. Appl. No. 13/102,123 dated Jun. 13, 2013.
RCE and Amendment for U.S. Appl. No. 13/102,123 dated Oct. 10, 2013.
Non-Final Rejection for U.S. Appl. No. 13/102,123 dated Oct. 24, 2013.
Amendment for U.S. Appl. No. 13/102,123 dated Feb. 24, 2014.
Final Rejection for U.S. Appl. No. 13/102,123 dated Mar. 18, 2014.
RCE and Amendment for U.S. Appl. No. 13/102,123 dated Aug. 15, 2014.
U.S. Appl. No. 13/102,127, filed May 6, 2011, Applicant-Initiated Interview Summary dated Nov. 25, 2013.
U.S. Appl. No. 13/102,127, filed May 6, 2011, Office Action dated Oct. 1, 2013.
U.S. Appl. No. 13/102,127, filed May 6, 2011, RCE and Amendment dated Oct. 2, 2012.
U.S. Appl. No. 13/102,127, filed May 6, 2011, Office Action dated Mar. 30, 2012.
U.S. Appl. No. 13/102,127, filed May 6, 2011, Amendment dated Dec. 22, 2011.
U.S. Appl. No. 13/102,127, filed May 6, 2011, Office Action dated Sep. 23, 2011.
U.S. Appl. No. 13/101,621, filed May 5, 2011, Amendment dated Dec. 20, 2013.
U.S. Appl. No. 13/101,621, filed May 5, 2011, Applicant-Initiated Interview Summary dated Nov. 25, 2013.
U.S. Appl. No. 13/101,621, filed May 5, 2011, Office Action dated Sep. 30, 2013.
U.S. Appl. No. 13/101,621, filed May 5, 2011, RCE and Amendment dated Oct. 2, 2012.
U.S. Appl. No. 13/101,621, filed May 5, 2011, Office Action dated Mar. 30, 2012.
U.S. Appl. No. 13/101,621, filed May 5, 2011, Amendment dated Dec. 22, 2011.
U.S. Appl. No. 13/101,621, filed May 5, 2011, Office Action dated Sep. 23, 2011.
U.S. Appl. No. 13/101,568, filed May 5, 2011, RCE and Amendment dated Dec. 2, 2013.
U.S. Appl. No. 13/101,568, filed May 5, 2011, Applicant-Initiated Interview Summary dated Nov. 22, 2013.
U.S. Appl. No. 13/101,568, filed May 5, 2011, Office Action dated Jul. 31, 2013.
U.S. Appl. No. 13/101,568, filed May 5, 2011, Amendment dated Jul. 9, 2012.
U.S. Appl. No. 13/101,568, filed May 5, 2011, Office Action dated Mar. 8, 2012.
Non-Final Rejection for U.S. Appl. No. 13/006,913 dated Sep. 8, 2014.
Amendment for U.S. Appl. No. 13/006,913 dated Dec. 8, 2014.
Non-Final Rejection for U.S. Appl. No. 13/102,111 dated Sep. 3, 2014.
Amendment for U.S. Appl. No. 13/102,111 dated Dec. 3, 2014.
Non-Final Rejection for U.S. Appl. No. 13/102,115 dated Jul. 7, 2014.
Amendment for U.S. Appl. No. 13/102,115 dated Oct. 7, 2014.
Non-Final Rejection for U.S. Appl. No. 13/102,123 dated Aug. 27, 2014.
Amendment for U.S. Appl. No. 13/102,123 dated Dec. 11, 2014.
Final Rejection for U.S. Appl. No. 13/006,913 dated Jan. 12, 2015.
Notice of Appeal for U.S. Appl. No. 13/006,913 dated Mar. 19, 2015.
Final Rejection for U.S. Appl. No. 13/102,111 dated Dec. 23, 2014.
Notice of Appeal for U.S. Appl. No. 13/102,111 dated Mar. 19, 2015.
Final Rejection for U.S. Appl. No. 13/102,115 dated Jan. 8, 2015.
Notice of Appeal for U.S. Appl. No. 13/102,115 dated Mar. 19, 2015.
Final Rejection for U.S. Appl. No. 13/102,123 dated Jan. 8, 2015.
Notice of Appeal for U.S. Appl. No. 13/102,123 dated Mar. 19, 2015.
Non-Final Rejection for U.S. Appl. No. 13/006,913 dated Jul. 2, 2015.
RCE and Amendment for U.S. Appl. No. 13/006,913 dated Jun. 19, 2015.
Non-Final Rejection for U.S. Appl. No. 13/102,111 dated Jul. 6, 2015.
RCE and Amendment for U.S. Appl. No. 13/102,111 dated Jun. 19, 2015.
Non-Final Rejection for U.S. Appl. No. 13/102,123 dated Jul. 7, 2015.
RCE and Amendment for U.S. Appl. No. 13/102,123 dated Jun. 19, 2015.
Amendment for U.S. Appl. No. 13/006,913 dated Oct. 2, 2015.
Amendment for U.S. Appl. No. 13/102,111 dated Oct. 6, 2015.
Amendment for U.S. Appl. No. 13/102,123 dated Oct. 6, 2015.
RCE and Amendment for U.S. Appl. No. 13/006,913 dated Jan. 22, 2016.
Final Rejection for U.S. Appl. No. 13/006,913 dated Oct. 23, 2015.
RCE and Amendment for U.S. Appl. No. 13/102,111 dated Jan. 22, 2016.
Final Rejection for U.S. Appl. No. 13/102,111 dated Oct. 23, 2015.
Notice of Appeal for U.S. Appl. No. 13/102,123 dated Jan. 22, 2016.
Final Rejection for U.S. Appl. No. 13/102,123 dated Nov. 19, 2015.
Appeal Brief for U.S. Appl. No. 13/006,913 dated May 18, 2016.

(56) References Cited

OTHER PUBLICATIONS

Non-Final Rejection for U.S. Appl. No. 13/006,913 dated Feb. 2, 2016.
Non-Final Rejection for U.S. Appl. No. 13/102,111 dated Feb. 11, 2016.
Appeal Brief for U.S. Appl. No. 13/102,111 dated May 10, 2016.
Appeal Brief for U.S. Appl. No. 13/102,123 dated Apr. 22, 2016.
Examiner's Answer to Appeal Brief for U.S. Appl. No. 13/006,913 dated Aug. 9, 2016.
Examiner's Answer to Appeal Brief for U.S. Appl. No. 13/102,123 dated Sep. 29, 2016.
Express Abandonment Under 37 CFR 1.138 for U.S. Appl. No. 13/102,123 dated Oct. 7, 2016.
Express Abandonment Under 37 CFR 1.138 for U.S. Appl. No. 12/102,111 dated Oct. 7, 2016.
Express Abandonment Under 37 CFR 1.138 for U.S. Appl. No. 13/006,913 dated Oct. 7, 2016.

Fig. 3

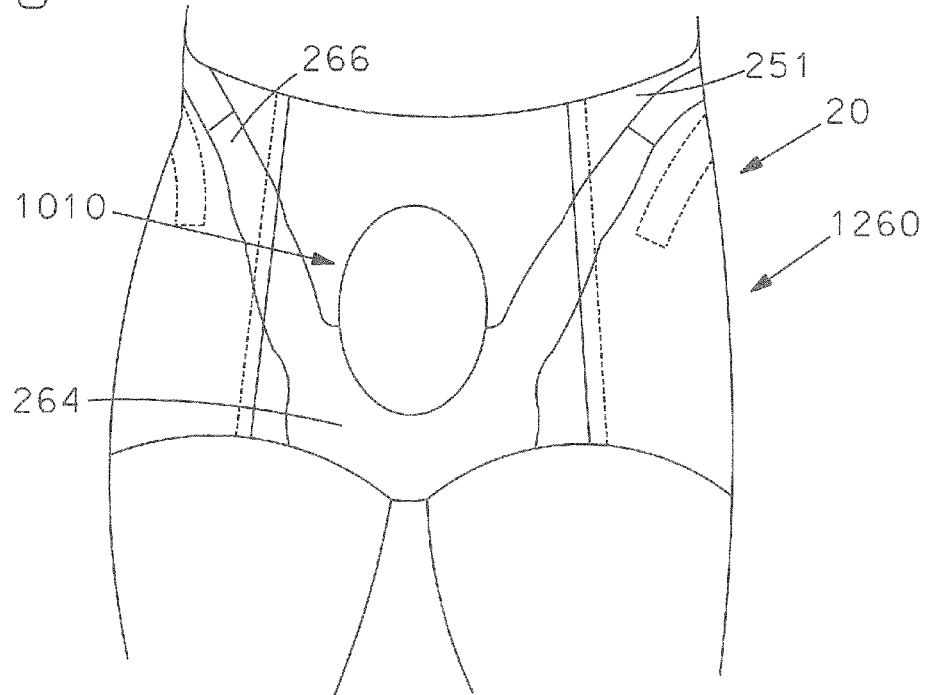
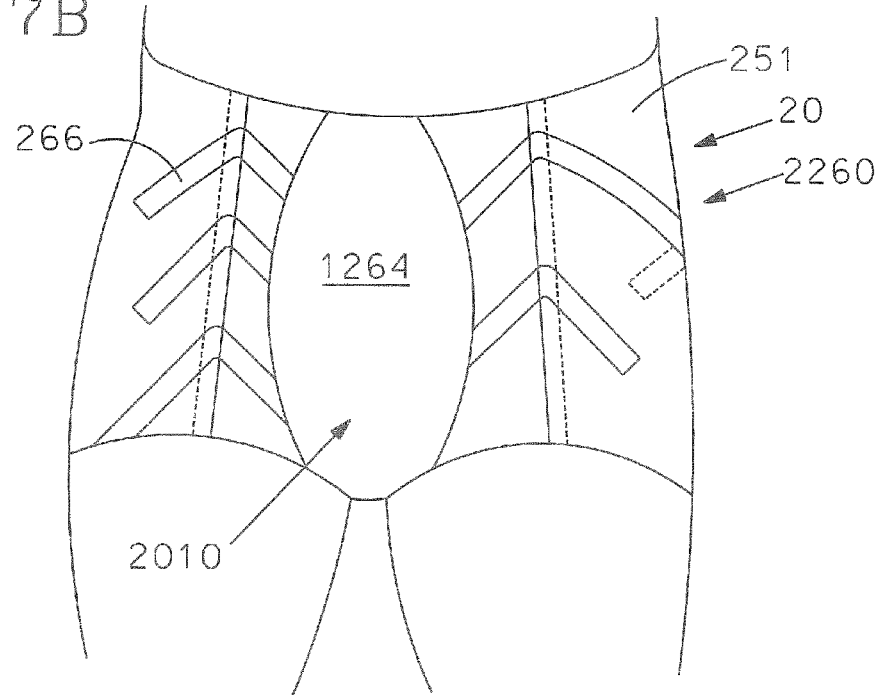

METHOD OF CONSTRUCTING ABSORBENT ARTICLES COMPRISING GRAPHICS

CROSS REFERENCE TO RELATED APPLICATIONS

This application is a continuation of U.S. application Ser. No. 13/006,913 (U.S. Pub. No. US 2011-0112499) filed on Jan. 14, 2011, still pending and which is a continuation of Ser. No. 11/999,229 (U.S. Pat. No. 7,896,858 B2) filed on Dec. 4, 2007, which claims the benefit of U.S. Provisional Application Nos. 60/872,697, filed Dec. 4, 2006, and 60/899,985, filed Feb. 6, 2007, the substances of which are incorporated herein by reference.

FIELD OF THE INVENTION

The present invention relates to the field of absorbent articles, and more particularly to the field of absorbent articles comprising graphics and/or color fields.

BACKGROUND OF THE INVENTION

There is a desire to make disposable absorbent articles look more like underwear. There are several factors that can affect whether an absorbent article is perceived as underwear-like. These factors include, but are not limited to, the noticeability of seams, the existence of graphics on a larger percentage of the viewable outer surfaces of the absorbent article, and graphics flowing from or over two or more absorbent article components.

There are, however, many obstacles to designing and executing an absorbent article that is underwear-like. One reason is that as new disposable absorbent article technologies are developed, they are incorporated as components. For example, seams are created to add stretchable elastomeric side panels or ears to the chassis and front or back regions of the absorbent article. Further, because of the manner in which absorbent article components are incorporated, even the viewable outer surfaces of the article have seams. Thus, it is challenging to place graphics on these individual components and to line them up such that the seams are not emphasized by process variations. Further, depending on the type of article construction, it is challenging to maintain the desired levels of breathability when adding graphics to each of the components having outer viewable surfaces. For these and other reasons, it is challenging to create an absorbent article that comprises mainstream technologies and also comprises graphics on multiple absorbent article components, such that the graphics flow from absorbent article component to component in a manner that deemphasizes seams and creates a holistic underwear-like appearance.

It is a desire of the present invention to provide absorbent articles that look like underwear, while, at the same time, incorporating absorbent article components that offer the benefits and functionality of the latest technologies (e.g., high stretch components integrated with low/no stretch components, highly breathable components, etc.). More specifically, it is a desire of the present invention to provide absorbent articles comprising graphics spanning the viewable absorbent article components, including absorbent articles comprising stretchable and breathable components. Further, it is a desire of the present invention to provide absorbent articles that have a Seam Noticeability Rating of less than about 7.

BRIEF DESCRIPTION OF THE DRAWINGS

While the specification concludes with claims particularly pointing out and distinctly claiming the invention, it is believed that the present invention will be better understood from the following description of embodiments which are taken in conjunction with the accompanying drawings and which like designations are used to designate substantially identical elements, and in which:

FIG. 3 is a partially cut-away plan view of the absorbent article of FIG. 1;

FIGS. 7A and B are perspective views (in use) of the absorbent article of FIG. 1 comprising alternate graphics;

DETAILED DESCRIPTION OF THE INVENTION

As used herein, "colored absorbent article component" refers to a component of an absorbent article which comprises color, but does not comprise a graphic (as defined herein). Colored absorbent article components may comprise gradations of color.

As used herein, "elastomer" refers to any material exhibiting elastic properties as described herein.

As used herein, "elastic" or "elastomeric" refers to any material which is able to extend to a strain of at least 50% without breaking or rupturing when subjected to a tensile force, and is able to recover substantially to its original dimensions after the force has been removed; where % strain=((extended length−unextended length)/unextended length)×100.

As used herein, "extensible" refers to any material that generally is able to extend to a strain of at least 50% without breaking or rupturing.

As used herein, "graphic" refers to formation of an object, which may or may not be colored. A graphic, however, does not include a field of color alone, wherein no formation of an object exists.

As used herein, "graphic absorbent article component" refers to a component of an absorbent article which comprises a graphic. Graphic absorbent article components may additionally comprise color, including color accents, or a field of color which does not form part of an object.

As used herein, "non-stretchable" refers to materials which cannot stretch to at least about 5% on the upcurve of the hysteresis test at a load of about 400 gm/cm. U.S. Prov. Pat. App. No. 60/811,580 describes the hysteresis test in greater detail.

Figure 13:
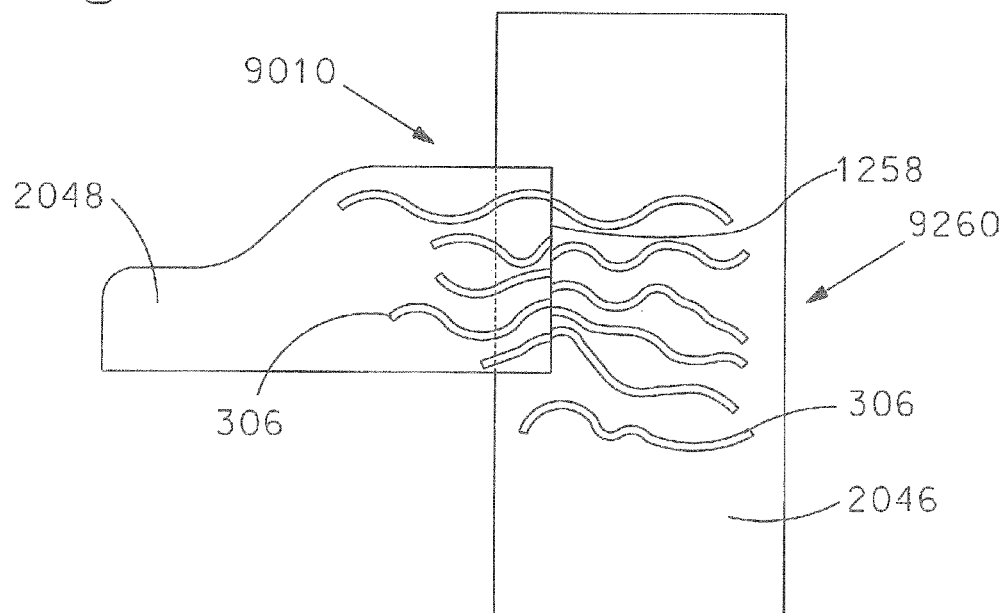
FIG. 13 is a partial side view of the absorbent article of FIG. 11, wherein the ear panels are shown overlapping, wherein the ear panels comprise alternate graphics.

As used herein, "seam margin" refers to the distance between a distal point of a graphic on a first graphic absorbent article component and an overlapping edge of a second graphic absorbent article component. Refer to FIG. 13.

As used herein, "set" or "percent set" refer to the percent deformation of an elastomeric material measured while the material is in a relaxed condition for a specified period of time after the material was released from a specified elongation without allowing the material to snap back completely. The percent set may be expressed as [(zero load extension after one cycle-initial sample gauge length of cycle 1)/(initial sample gauge length of cycle 1)]×100. Zero load extension refers to the distance between the jaws at the beginning of the second cycle before a load is registered by the tensile testing equipment. Further definition of "set" or "percent set" may be found in U.S. Pat. No. 6,617,016.

As used herein, "stretchable" refers to materials which can stretch to at least an elongated length of about 105% on the upcurve of the hysteresis test at a load of about 400 gm/cm. U.S. Prov. Pat. App. No. 60/811,580 describes the hysteresis test in greater detail.

As used herein, "viewable inner surface" refers to the viewable body-facing surface (e.g., topsheet 24. The viewable inner surface may comprise multiple layers).

As used herein, "viewable outer surface" refers to the outer facing surface of an absorbent article which is viewable when the absorbent article is worn (e.g., the garment facing side of the outer cover 22). The viewable outer surface may comprise multiple layers.

As used herein, "whole graphics" refers to a complete graphic, uninterrupted by absorbent article component finishing or one absorbent article component overlapping another. Refer to FIG. 15C which illustrates whole graphics, whereas FIG. 15B illustrates graphics which are interrupted or cut-off.

Reference will now be made in detail to embodiments and illustrations of the present invention(s). Except for FIGS. 21-22A-D, numerals with the same last three digits represent the same or similar elements throughout the figures (e.g., 122, 1122, 2122, or 20, 1020, 2020).

Figure 1:
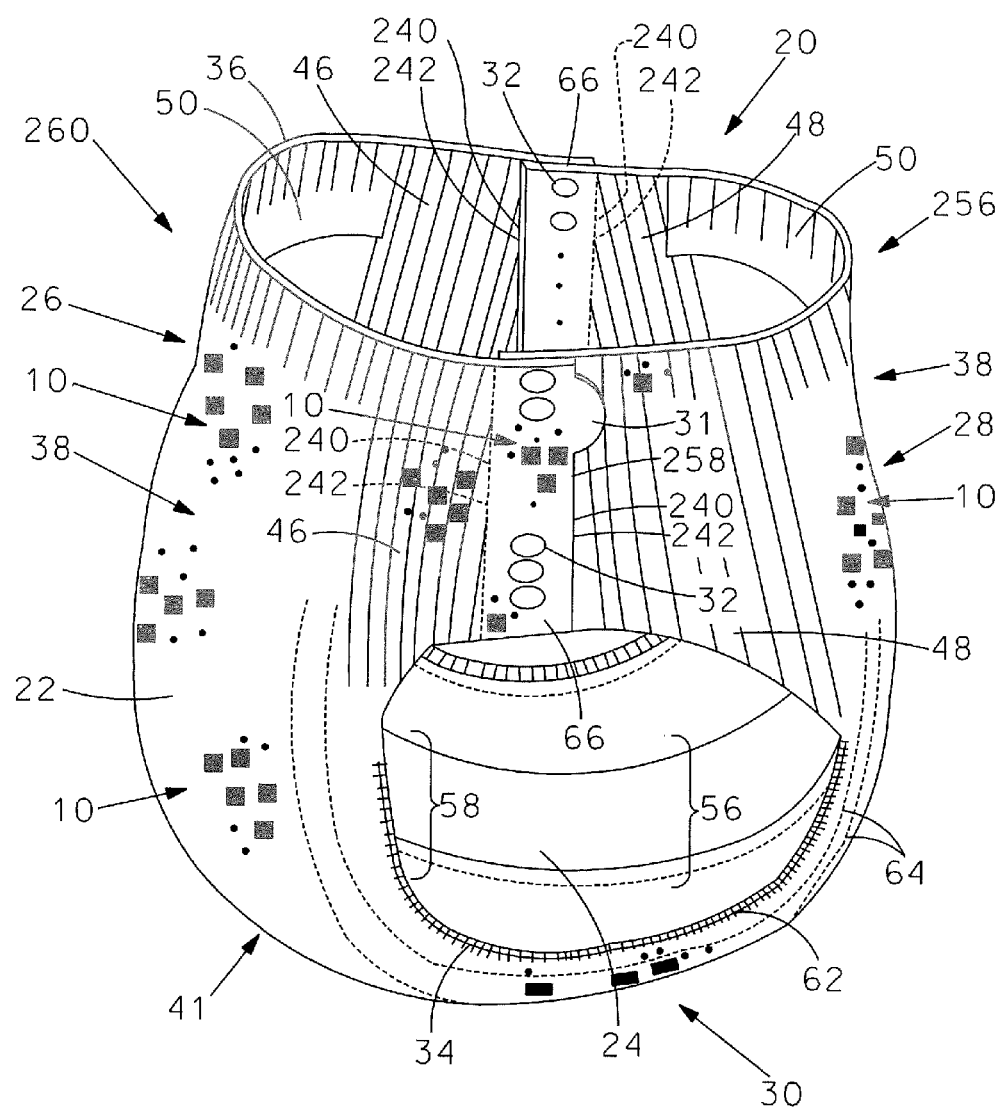
FIG. 1 is a perspective view of an embodiment of an absorbent article of the present invention.

Referring to FIG. 1, an absorbent article 20 of the present invention may have a front region 26; a back region 28 and a crotch region 30 between the front region 26 and the back region 28. A chassis 41 may be provided in the front, back and crotch regions 26, 28 and 30. The chassis 41 may include a liquid previous topsheet 24, a nonwoven outer cover (interchangeably referred to as a "backsheet") 22, a liquid impervious film 68 (see FIG. 3) associated with the topsheet 24, and an absorbent core 25 (see FIG. 3) disposed between the topsheet 24 and the film 68.

The absorbent article 20 may include a pair of extensible front ear panels 46, each extending laterally outward from the corresponding sides of the chassis 41 in the front region 26, and a pair of extensible back ear panels 48, each extending laterally outward from the corresponding sides of the chassis 41 in the back region 28 ("ear panels" and "side panels" may be used interchangeably). Each of the ear panels 46 and 48 may have an outermost edge 240 which forms an outermost edge line 242. At least one of the outermost edge lines 242 may have a nonuniform lateral distance LD from the longitudinal center line 100 (see FIG. 3) in an uncontracted state. The absorbent article 20 may further include bonds 32, each joining the front and back ear panels 46 and 48 along the corresponding edge lines 242 to form two leg openings 34 and a waist opening 36.

The pairs of the ear panels 46 and 48 may be elastically extensible in at least the lateral direction. In alternative embodiments, the ear panels 46 and 48 may be elastically extensible both in the lateral and longitudinal directions.

The ear panels 46 and 48 may be formed by unitary elements of the absorbent article 20 (wherein the ear panels 46 and 48 are not separately manipulative elements secured to the absorbent article 20, but are formed from and are extensions of one or more of the various layers of the absorbent article). Each of the ear panels 46 and 48 may be a projected member of the chassis 41 (more clearly shown in FIG. 3). The ear panels 46 and 48 may include at least one unitary element or a continuous sheet material (e.g., the nonwoven outer cover 22 in FIG. 4) that forms a part of the chassis 41 and continuously extends into the ear panels 46 and 48. Alternatively, the ear panels 46 and 48 may be discrete members which do not have any unitary element that forms a part of the chassis 41, and may be formed by joining the discrete members to the corresponding sides of the chassis 41 (see FIG. 11).

The absorbent article 20 may further include seam panels 66, each extending laterally outward from each of the ear panels 46 and 48; and tear open tabs 31 each, extending laterally outward from the seam panel 66. Each of the seam panels 66 may be an extension of the corresponding ear panels 46 and 48, or at least one of the component elements used therein, or any other combination of the elements. Each of the tear open tabs 31 may also be an extension of the corresponding seam panel 66 or at least one of its component elements used therein, or any other combination of its elements.

The tear open tab 31 can take any shape as long as it facilitates intentional tearing open at the bonds 32 after soiling of the absorbent articles 20. The lateral distance LD from the longitudinal center line 100 may increase towards the leg opening 34 (not shown).

Figure 2:
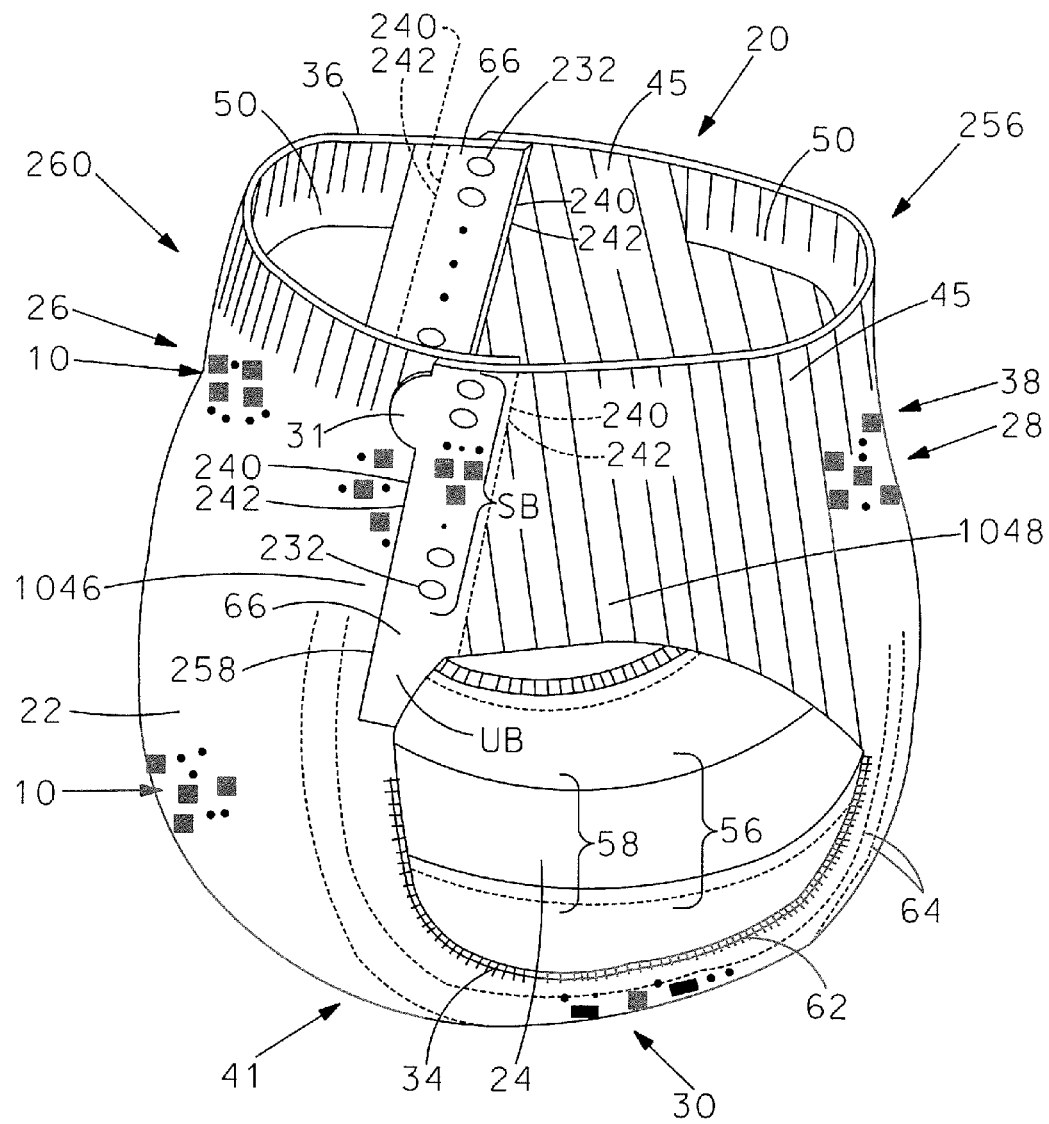
FIG. 2 is a perspective view of an alternate embodiment of the absorbent article of FIG. 1, wherein the shape and orientation of the ear panels are altered.

Corresponding edge portions of the chassis 41 and/or the ear panels 46 and 48 may he bonded directly or indirectly (e.g., through the seam panels 66), in an overlapping manner to form a seam 258. As shown in FIG. 2, the front ear panel 46 may overlap the back ear panel 48. Alternatively, as shown in FIG. 2, the back ear panel 1048 may overlap the front ear panel 1046. Alternatively, the front and ear panels 46 and 48 can be bonded in a butted manner (not shown in Figs.). The bonding of the bonds 32 can be performed by any suitable means known in the art appropriate for the specific materials employed in the chassis 41 and/or the ear panels 46 and 48. Thus, sonic sealing, heat sealing, pressure bonding, adhesive or cohesive bonding, sewing, autogeneous bonding, and the like may be appropriate techniques. The seam panels 66 may be joined by a predetermined pattern of heat/pressure or ultrasonic welds which withstands the forces and stresses generated on the absorbent article 20 during wear.

A continuous belt 38 may be formed by the ear panels 46 and 48, and a part of the chassis 41 about the waist opening 36 as shown in FIGS. 1 and 2, Elasticized waist bands 50 may be provided in both the front region 26 and the back region 28.

Figure 3:
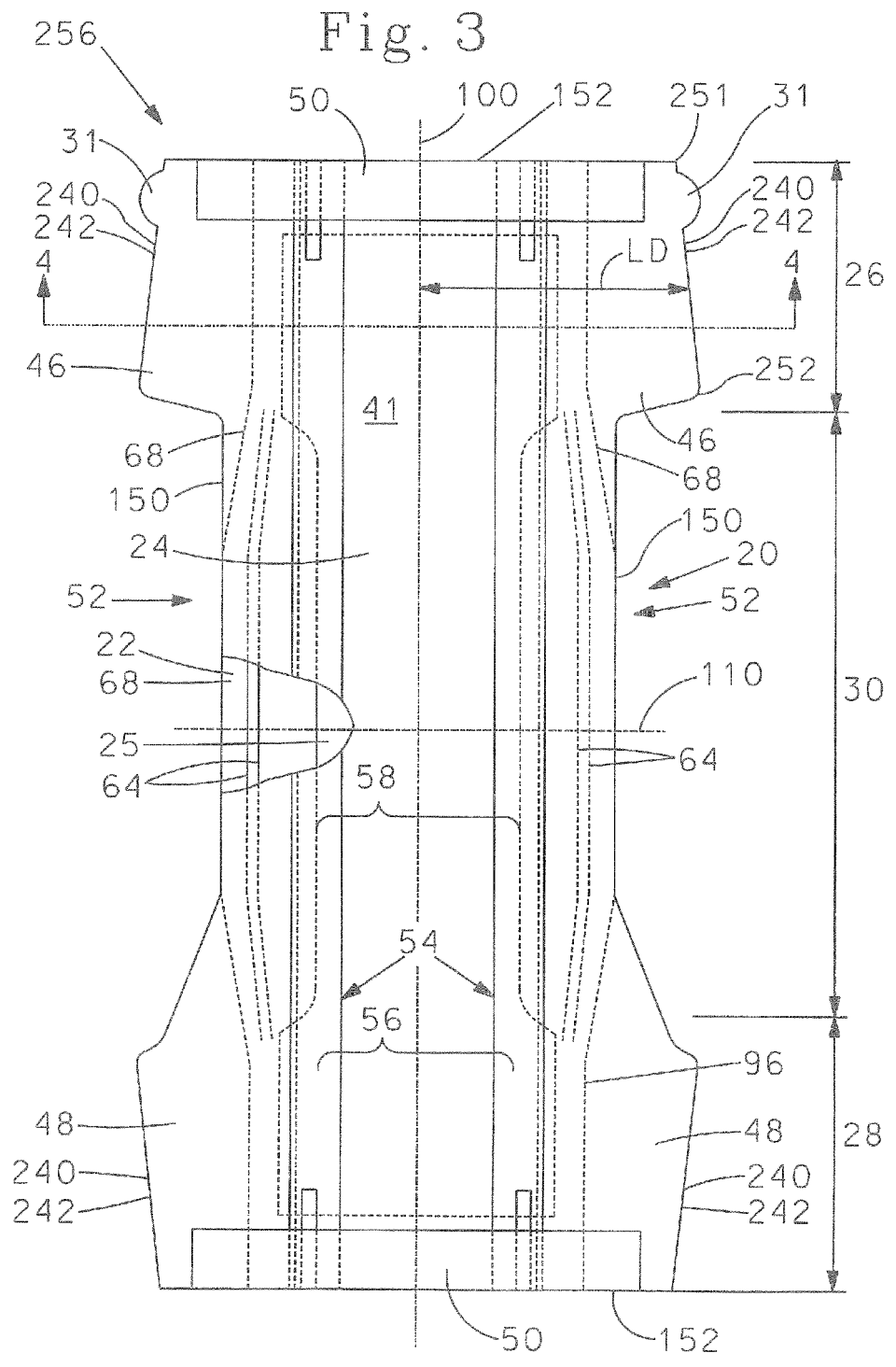

FIG. 3 is a partially cut-away plan view of the absorbent article 20 of FIG. 1 in its uncontracted state (except in the ear panels 46 and 48 which are left in their relaxed condition) with the topsheet 24 facing the viewer, prior to the ear panels 46 and 48 being joined together by the bonds 32. As illustrated, the absorbent article 20 may have the front region 26, the back region 28 opposed to the front region 26, the crotch region 30 positioned between the front region 26 and the back region 28, and a periphery which is defined by the outer perimeter or edges of the absorbent article 20 in which the side edges are designated 150 and 240, and the end edges or waist edges are designated 152. The topsheet 24 may be the body-facing surface of the absorbent article 20 which may be positioned adjacent to the wearer's body during use. The nonwoven outer cover 22 (also known as a backsheet) may have the outer-facing surface of the absorbent article 20 which may be positioned away from the wearer's body. Additionally, the outer cover 22 may comprise graphics 10 (described more below). The absorbent article 20 may include the chassis 41 including the liquid previous topsheet 24, the liquid impervious film 68 associated with the topsheet 24, a nonwoven outer cover 22, and the absorbent core 25 positioned between the topsheet 24 and the impervious film 68. In an alternate embodiment, there may be no impervious film 68, but rather, a nonwoven core forming layer (not shown), also known as a dusting layer, may serve the function of the liquid impermeable film 68. The absorbent article 20 may further include the front and back ear panels 46 and 48 extending laterally outward from the chassis 41, the elasticized leg cuffs 52, and the elasticized waistbands 50. The topsheet 24 and the nonwoven outer cover 22 may have length and width dimensions generally larger than those of the absorbent core 25. The topsheet 24 and the nonwoven outer cover 22 may extend beyond the edges of the absorbent core 25 to thereby form the side edges 150 and the waist edges 152 of the absorbent article 20.

The absorbent article 20 may also have two centerlines, a longitudinal centerline 100 and a transverse centerline 110. Herein, "longitudinal" refers to a line, axis, or direction in the plane of the absorbent article 20 that is generally aligned with (e.g., approximately parallel with) a vertical plane which bisects a standing wearer into left and right halves when the absorbent article 20 is worn. Herein, "transverse" and "lateral" are interchangeable and refer to a line, axis or direction which lies within the plane of the absorbent article that is generally perpendicular to the longitudinal direction (which divides the wearer into front and back body halves). The absorbent article 20 and component materials thereof may also have a body-facing surface which faces the skin of wearer in use and an outer-facing surface which is the opposite surface to the body-facing surface.

Each of the ear panels 46 and 48 of the present invention may have an outermost edge line 242. Herein, "edge line" refers to lines which define the outlines of the ear panels 46 and 48 or the chassis 41. Herein, "outermost" refers to portions which are farthest from the longitudinal centerline 100. At least one of the edge lines 242 may have a nonuniform lateral distance LD from the longitudinal center line 100 in the uncontracted state of the absorbent article 20.

The outermost edge line 242 may have a first point 251 at the closest portion to the waist opening 36 and a second point 252 at the closest portion to the leg opening 34, and the outermost edge line 242 is a straight line defined by connecting the first and second points 251 and 252. The outermost edge line 242 shows the direction of the outermost edge 240 of the ear panel. The edge line 242 may lean to the longitudinal center line 100 in the uncontracted state of the absorbent article 20. The outermost edge line 242 may have, in the uncontracted state of the absorbent article 20, a lateral distance LD from the longitudinal center line 100 which increases towards the leg opening 34 as shown in FIG. 3. Alternatively, the outermost edge line 242 may have, in the uncontracted state of the absorbent article 20, a lateral distance LD from the longitudinal center line 100 which decreases towards the leg opening 34 (not shown in Figs.).

While the topsheet 24, the nonwoven outer cover 22, and the absorbent core 25 may be assembled in a variety of well known configurations, exemplary chassis configurations are described generally in U.S. Pat. No. 3,860,003 (Buell); and U.S. Pat. No. 5,151,092 (Buell et al).

Figure 4:
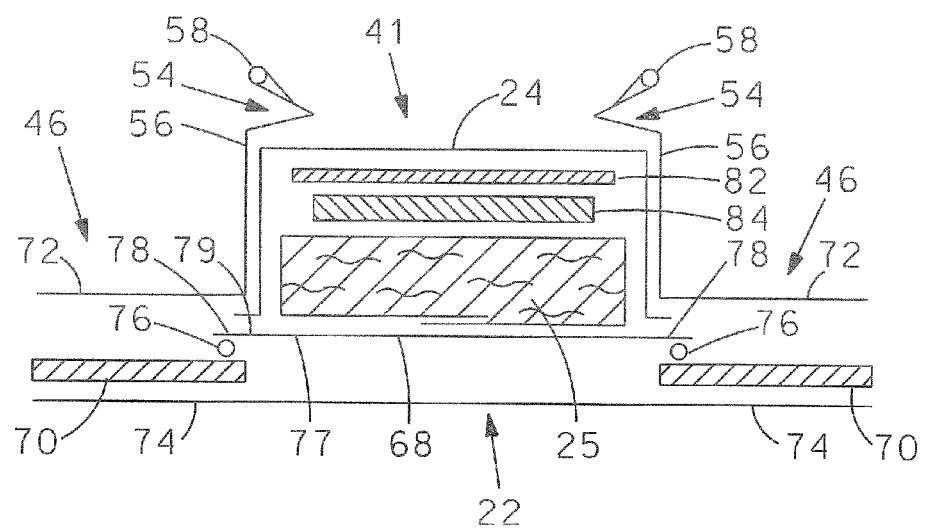
FIG. 4 is a cross-sectional view of the absorbent article of FIG. 3 taken along the section line 4-4.
Figure 5:
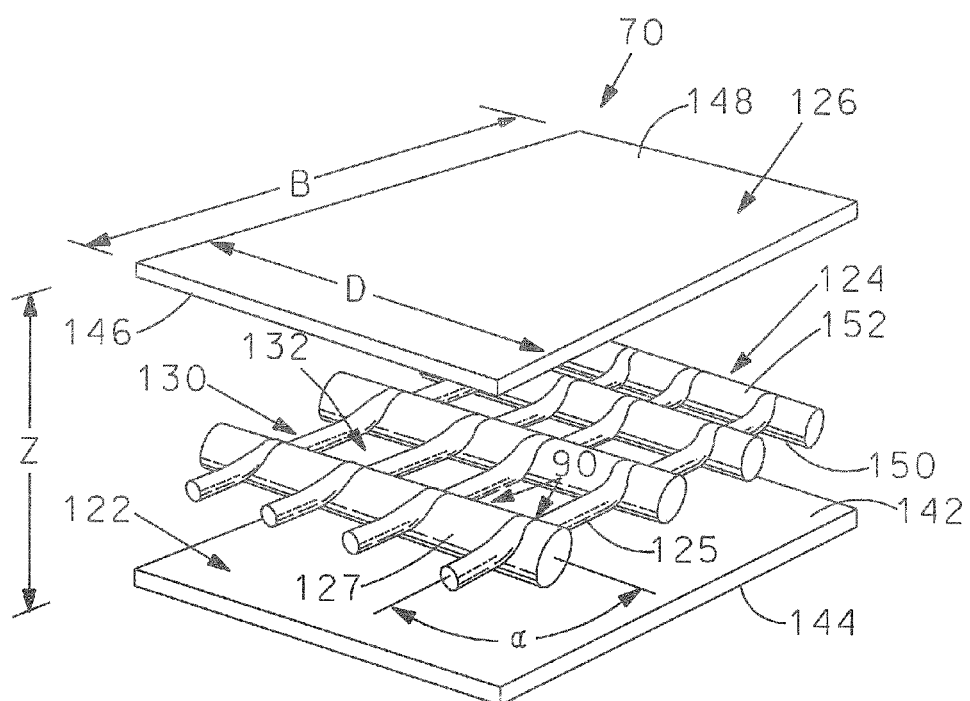
FIG. 5 is an exploded perspective view of an elastic member of an ear panel of the absorbent article of FIG. 1.

FIG. 4 is a cross-sectional view of an embodiment taken along the section line 4-4 of FIG. 3. The absorbent article 20 may include the chassis 41, including the liquid previous topsheet 24, the nonwoven outer cover 22 associated with the topsheet 24, and the absorbent core 25 positioned between the topsheet 24 and the nonwoven outer cover 22. The absorbent article 20 may further include the front ear panels 46, each extending laterally outward from the chassis 41, and inner barrier cuffs 54. Although FIG. 4 depicts only the structure of the front ear panel 46 and the chassis 41 in the front region 26, a similar structure may also be provided in the back region 28. Each of the front ear panels 46 may be formed by a lamination of an extended part 72 of the barrier flap 56, an elastic member 70 and the nonwoven outer cover 22. The elastic member 70 may include a plane elastomeric material 124 (see FIG. 5). Herein, "plane elastomeric material" refers to elastomeric materials which continuously extend in two dimensional directions. Plane elastomeric materials include a scrim, a perforated (or apertures formed) film, an elastomeric woven or nonwoven; and the like. The plane elastomeric material 124 may include at least a portion that has a nonuniform lateral width.

The absorbent core 25 can be any absorbent member which is generally conformable, non irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable absorbent articles and other absorbent articles such as comminuted wood pulp which is generally referred to as airfelt. Examples of other suitable absorbent materials include creped cellulose wadding; meltblown polymers including conform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

In an embodiment of the invention, the absorbent core 25 may have, in the uncontrasted state of the absorbent article 20, an area ratio of the core area to the garment area of greater than about 25% or greater than about 40%. The core area is defined as the total area of the body-facing surface of the absorbent core 25 in the uncontracted state of the absorbent article 20. The periphery of the body-facing surface of the absorbent core 25 is determined by the outline of aggregates of primary absorbent materials used in the absorbent core 25. Herein, "primary absorbent material" refers to absorbent materials which occupy more than about 80% in dry state volume of the absorbent core 25. Wood pulp (e.g., airfelt) may be considered a primary absorbent material of the absorbent core 25 and may define the periphery of the body-facing surface of the absorbent core 25, thus defining the core area of the absorbent core 25. The other primary absorbent materials may include creped cellulose wadding; meltblown polymers including conform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The garment area is defined as the total area of the body-facing surface of the absorbent article 20 in the uncontracted state. Therefore, the area ratio is calculated as follows:

$AR=CA/GA \times 100$ wherein, $AR$: the area ratio (%), $CA$: the core area (cm$^2$), $GA$: the total area (cm$^2$)

The absorbent core 25 may have a core area of less than about 450 cm$^2$ or less than about 425 cm$^2$. The absorbent core 25 may have a maximum core width of less than about 12 cm or less than about 11 cm. Herein, "core width" refers to the lateral distance from one side edge to the other side edge of the absorbent core 25.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may include one or more layers or structures) Further, the size and absorbent capacity of the absorbent core 25 may also be varied to accommodate wearers ranging from infants through adults. However, the total absorbent capacity of the absorbent core 25 should be compatible with the design loading and the intended use of the absorbent article 20.

The absorbent article 20 may have an asymmetric, modified hourglass-shaped absorbent core 25 having ears in the front and back waist regions 26 and 28. Other exemplary absorbent structures for use as the absorbent core 25 that have achieved wide acceptance and commercial success are described in U.S. Pat. Nos. 4,610,678, 4,673,402, 4,888,231, and 4,834,735.

The chassis 41 may further include an acquisition/distribution core 84 of chemically stiffened fibers positioned over the absorbent core 25, thereby forming a dual core system. The fibers may be hydrophilic chemically stiffened cellulosic fibers. Herein, "chemically stiffened fibers" means any fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

The nonwoven outer cover 22 may include the liquid impervious film 68 as shown in, for example, FIG. 4. The liquid impervious film 68 may longitudinally extend in the front, back and crotch regions 26, 28 and 30. The liquid impervious film 68 may not laterally extend into at least one of the ear panels 46 or 48. The liquid impervious film 68 may have a body-facing surface 79 and an outer-facing surface 77. The liquid impervious film 68 may be impervious to liquids (e.g., urine) and may be manufactured from a thin plastic film. However, the plastic film may permit vapors to escape from the absorbent article 20. In one embodiment, a microporous polyethylene film is used for the liquid impervious film 68. A suitable microporous polyethylene film is manufactured by Mitsui Toatsu Chemicals, Inc., Nagoya, Japan and marketed in the trade as PGP. A disposal tape (not shown in Figs.) may additionally be joined to the outer-facing surface of the nonwoven outer cover 22 to provide a convenient disposal after soiling.

The nonwoven outer cover 22 may be compatible with other materials (e.g., component materials in the topsheet 24) used in the absorbent article 20, in terms of its design/process, for forming ventilation holes along the waist edge 152 and/or for forming bonds 32 in the absorbent article 20.

In an alternative embodiment, the absorbent core 25 is not joined to the nonwoven outer cover 22, and/or the topsheet 24 in order to provide greater extensibility in the front region 26 and the back region 28.

The absorbent article 20 may further include an elasticized waistband 50 that provides improved fit and containment. The elasticized waistband 50 is that portion or zone of the absorbent article 20 which is intended to elastically expand and contract to dynamically fit the wearer's waist. The elasticized waistband 50 may extend longitudinally outwardly from the waist edge of the absorbent article 20 toward the waist edge of the absorbent core 25. The absorbent article 20 may have two elasticized waistbands 50, one positioned in the back region 28 and one positioned in the front region 26, although other pull-on diaper embodiments can be constructed with a single elasticized waistband. The elasticized waistband 50 may be constructed in a number of different configurations including those described in U.S. Pat. Nos. 4,515,595 and 5,151,092.

The waistbands 50 may include materials that have been "prestrained" or "mechanically prestrained" (i.e., subjected to some degree of localized pattern mechanical stretching to permanently elongate the material). The materials may be prestrained using deep embossing techniques as are known in the art. Alternatively, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189, 4,107;364, 4,209,563, 4,834,741 and 5,151,092.

At least one of the ear panels 46 and 48 may include the elastic member 70 as shown in FIG. 4. The elastic member 70 of the front ear panels 46 may include the elastomeric material 124 (see FIG. 5) which extends laterally outward from the chassis 41 to provide good fit by generating the optimal retention (or sustained) force at the waist and side areas of the wearer. The elastomeric material 124 may be extensible in at least one direction, including in the lateral direction, to generate a retention (or sustained) force that is optimal to prevent the absorbent article 20 from drooping, sagging, or sliding down from its position on the torso without causing the red marking on the skin of the wearer. In one embodiment, each of the ear panels 46 and 48 includes the elastomeric material 124. The elastic member 70 may be operatively joined to at least one of the nonwoven webs 72 and 74 in the ear panels 46 and 48 to allow the elastic member 70 to be elastically extensible in at least the lateral direction. In one embodiment, the elastic member 70 is operatively joined to the nonwoven webs 72 and 74 by securing them to at least one, and in some cases, both of the nonwoven webs 72 and 74 while in a substantially untensioned (zero strain) condition.

The elastic member 70 can he operatively joined to the nonwoven webs 72 and 74, by using either an intermittent bonding configuration or a substantially continuous bonding configuration. Herein, "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. The stretch laminate may be bonded over all or a significant portion of the stretch laminate so that the inelastic webs (i.e., the nonwoven webs 72 and 74) elongate or draw without causing rupture, and the layers of the stretch laminates may be bonded in a configuration that maintains all of the layers of the stretch laminate in relatively close adherence to one another after the incremental mechanical stretching operation. Consequently, the elastic panel members and the other plies of the stretch laminate may be substantially continuously bonded together using an adhesive. In one embodiment, the adhesive selected is applied with a control coat spray pattern at a basis weight of about 7.0 grams/square m. The adhesive pattern width may be about 6.0 cm. The adhesive may be available from Nitta Findley Co., Ltd., Osaka, Japan, under the designation H2085F. Alternatively, the elastic panel member and any other components of the stretch laminates may be intermittently or continuously bonded to one another using heat bonding, pressure bonding, ultrasonic bonding, dynamic mechanical bonding, or any other method as is known in the art.

After the elastic member 70 is operatively joined to at least one of the nonwoven webs 72 and 74, at least a portion of the resultant composite stretch laminate may then be subjected to mechanical stretching sufficient to permanently elongate the non-elastic components which are, for example, the nonwoven webs 72 and 74. The composite stretch laminate may then allowed to return to its substantially untensioned condition. At least one pair of both of the ear panels 45, 46 and 48 may thus be formed into "zero strain" stretch laminates. (Alternatively, the elastic member 70 could be operatively joined in a tensioned condition and then subjected to mechanical stretching) Herein, "zero strain" stretch laminate refers to a laminate included of at least two plies of material which are secured to one another along at least a portion of their coextensive surfaces while in a substantially untensioned ("zero strain") condition; one of the plies including a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Methods and apparatus used for making stretch laminates utilize meshing corrugated rolls to mechanically stretch the components. Apparatus and methods are disclosed in U.S. Pat. Nos. 5,167,897, 5,156,793 and 5,143,679.

Figure 6:
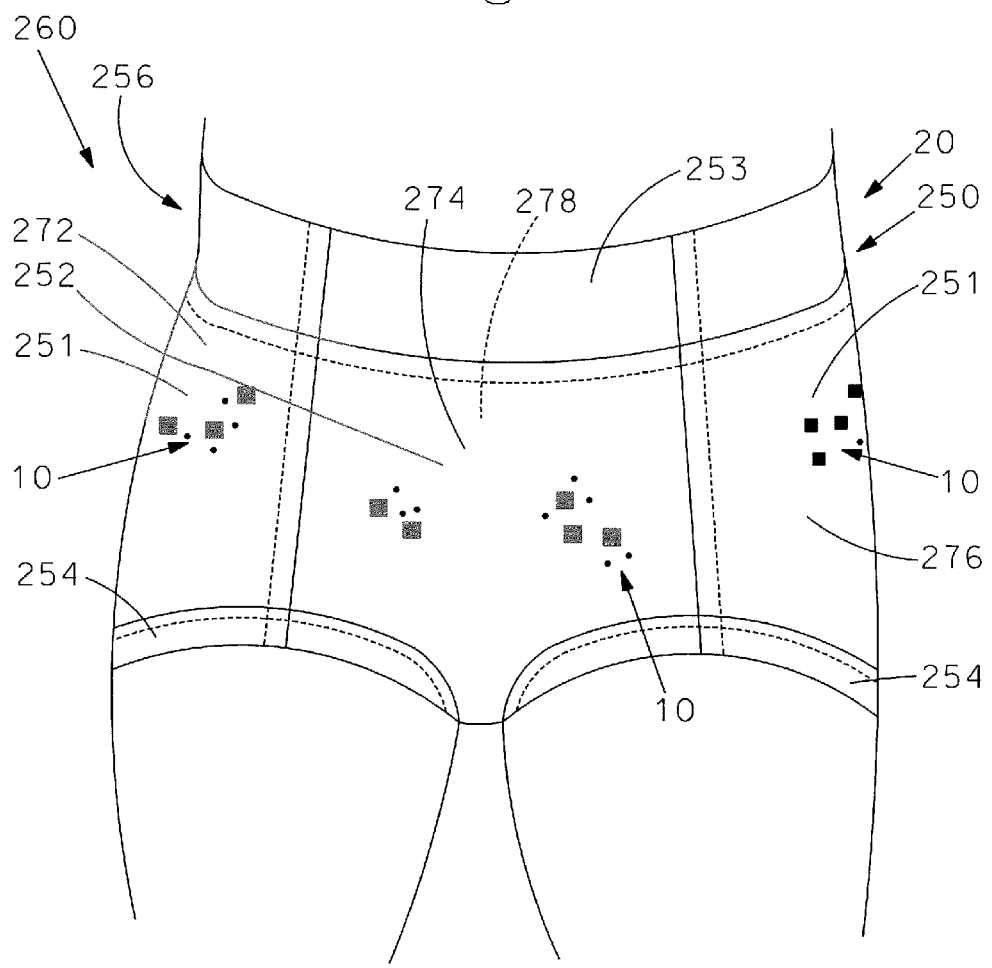
FIG. 6 is a perspective view in use) of the absorbent article of FIG. 1 illustrating various zones.

Referring to FIG. 6, the absorbent article may comprise multiple zones 250, including a side zone 251 (which may be further divided into right and left, and front and back), a central zone 252 (which may be further divided into front, middle, and back), a waist band zone 253, and leg band zones 254 (which may be further divided into left and right). Each of the expressed zones may be further divided into a viewable body-facing surface and a viewable outer-facing surface. Zones 250 may overlap. Further, a zone 250 may comprise one or more absorbent article components (not shown in FIG. 6).

An absorbent article (e.g., 20) may comprise multiple components (e.g., 256), many of which have been mentioned, described, and illustrated thus far, including, but not limited to, an absorbent core (e.g., 25), an ear panel (e.g., 46, 48), a landing zone, a topsheet (e.g., 24), an acquisition layer, a core cover, a fastener (e.g., 370), a dusting layer, a body side liner, an outer cover (e.g., 22), a core outer layer, waist members (e.g., 50), leg cuffs (e.g., 52), wetness sensation liners, a waist pocket member, a sensor or indicator (including wetness and fit), a sustained fit element, a stiffener, a removable absorbent member, an anchoring band, as well as, those absorbent article components mentioned, described, and illustrated in U.S. Pat. Nos. 5,569,234, 6,443,940, 4,892,536, 4,990,147, 5,037,416, 5,269,775, 4,515,595, 4,710,189, 5,151,092, 5,221,274, 3,848,594, 4,662,875, 4,846,815, 4,894,060, 4,946,527, 5,151,092, 5,221,274, 6,432,098, 4,699,622, 6,428,526, 3,860,003, 5,554,145, 5,569,234, 5,580,411, 6,004,306, 5,246,433, 6,120,487, 6,120,489, 4,940,464, 5,092,861, 5,897,545, 5,957,908, and U.S. patent application Ser. No. 10/222,438 (U.S. Pat. No. 6,905,488), 10/815,918, (U.S Pub. No. US 2005-0222546 (abandoned), 11/599,851 (U.S. Pat. No. 8,235,963), 11/541,325,(U.S. Pat. No. 8,066,687 and 11/599862 (U.S. Pub. No. US 2007-0287983 (abandoned). Absorbent article components (e.g., 256) may comprise multiple layers. Also, while the absorbent articles (e.g., 20) above are described as pants, the present invention may also be in the form of a taped absorbent article (not shown). Absorbent article zones (e.g., 250) or components (e.g., 256) may be attached to other zones (e.g., 250) or components (e.g., 256) using various bonding means (including, adhesive, fusion, ultrasonic, hot needle, wave, and other means described above). As described above, these bonds (e.g., 32) may be designed to fail upon a specific force (e.g., breaking the bond (e.g., 32) of two ear panels (e.g., 46 and 48) on a pant style absorbent article (versus tearing through the material of the ear panel (e.g., 46 and 48)). Alternatively, zones (e.g., 250) or components (e.g., 256) may be attached via fasteners (e.g., 370, FIG. 11) which are detachably reattachable (including, hooks/loops, adhesives, buttons, latches, snaps, etc.) For instance, a first ear panel (e.g., 46) may comprise hooks and a second ear panel (e.g., 48) may comprise loops such that the two side panels may be attached and detached several times. Without regard to the means, seams (e.g., 258) are formed when zones (e.g., 250) or components (e.g., 256) are attached to other zones (e.g., 250) or components (e.g., 256).

Absorbent article zones (e.g., 250), components (e.g., 256), or the materials (e.g., 124) comprised therein, may be stretchable, elastic, or extensible. For example, in one embodiment, an absorbent article (e.g., 20) may comprise stretchable, elastic, or extensible side zones 251, but its central zone (e.g., 252) may not be stretchable, elastic, or extensible. In another embodiment, an absorbent article (e.g., 20) may comprise central and side zones (e.g., 252 and 251), both of which are stretchable, elastic, or extensible.

In one embodiment, an absorbent article (e.g., 20) may comprise a stretchable, elastic, or extensible first component (e.g., an ear panel 46 and 48), but a second component (e.g., an outer cover 22) may not be stretchable, elastic, or extensible. This may include an absorbent article (e.g., 20) that has stretchable, elastic, or extensible ear panels (e.g., 46 and 48) or side zones (e.g., 251) and a non-stretchable, non-elastic, or non-extensible central zone (e.g., 252). This may also include an absorbent article (e.g., 20) that has a stretchable, elastic, or extensible central zone (e.g., 252) and non-stretchable, non-elastic, or non-extensible ear panels (e.g., 46 and 46). In another embodiment, an absorbent article (e.g., 20) may comprise multiple components (e.g., 256) which are stretchable, elastic, or extensible (e.g., both an ear panel 46 and 48, and an outer cover 22).

Absorbent article zones (e.g., 250) or components (e.g., 256) may comprise one or a combination of stretch-thermal laminates (STL), neck-bonded laminates (NBL), reversibly necked. laminates, and/or a stretch-bonded laminates (SBL), as well as elastomers described in U.S. Pat. Nos. 4,663,220 and 5,226,992, and European Pat. No. 0 217 032, Further, absorbent article components (e.g., 256) may comprise one or a combination of styrene-olefin-styrene block copolymers (including, styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-IB-S)), polypropylene, polyethylene, polybutadiene, polyisoprene, polystyrene-ethylene-butylene-polystyrene block copolymers, polystyrene-ethylene-ethylene/propylene-styrene (S-E-EP-S) block copolymers, styrenic-olefinic block copolymers, thermoplastic polymers (including, polyphenylene oxide and vinylarene resins derived from monomers including styrene, α-methyl styrene, other styrene derivatives, and vinyl toluene), as well as elastomers described in U.S. Pat. No. 6,617,016.

Absorbent article zones (e.g., 250), components (e.g., 256), or the materials (e.g., 124) comprised therein, may be able to stretch to an elongated length of at least about 110%, or about 125% of its relaxed, original length (i.e., can stretch to about 10 percent, or about 25% more than its original length), without rupture or breakage, and upon release of the applied force, may recover at least about 40% of its elongation, or at least 60% of its elongation, or about 80% of its elongation. For example, a material (e.g., 124) that has an initial length of 100 mm may extend to at least about 110 mm, and upon removal of the force would retract to a length of about 106 mm (40% recovery).

Absorbent article zones (e.g., 250), components (e.g., 256), or the materials (e.g., 124) comprised therein, may have a permanent set (i.e., percent set or % set) less than about 60%, less than about 50%, less than about 40%, less than about 30%, less than about 20%, less than about 15%, less than about 10%, less than about 5%, less than about 3%, less than about 2%, or less than about 1%. Absorbent article zones (e.g., 250), components (e.g., 256), or the materials (e.g., 124) comprised therein, or portions thereof, may be treated to be made stretchable, elastic, or extensible (or more stretchable, elastic, or extensible). Treatments may include ring-rolling and SELFing (as further described in U.S. Pat. Nos. 4,463,045 and 5,554,143, as well as electronic beam cross. linking.

Absorbent article components (e.g., 256) may comprise one or more graphics (e.g., 10), and may more particularly be referred to as "graphic absorbent article components" (e.g., 9260, see FIG. 13). Graphics (e.g., 10) may include, but not limited to, letters, numbers, symbols, icons, mammal representations, animal representations, insect representations, fish representations, vehicle representations, geometric shapes (e.g., circles, triangles, squares, rectangles, straight and wavy lines, etc.), animations, photographic images, plant representations, landscape representations, patterns (symmetrical or random), textile-like prints or patterns, foliage representations, anthropomorphic representations, as well as those graphics described in U.S. Pat. Pub. No. 2006/0247594 (abandoned).

Figure 19:
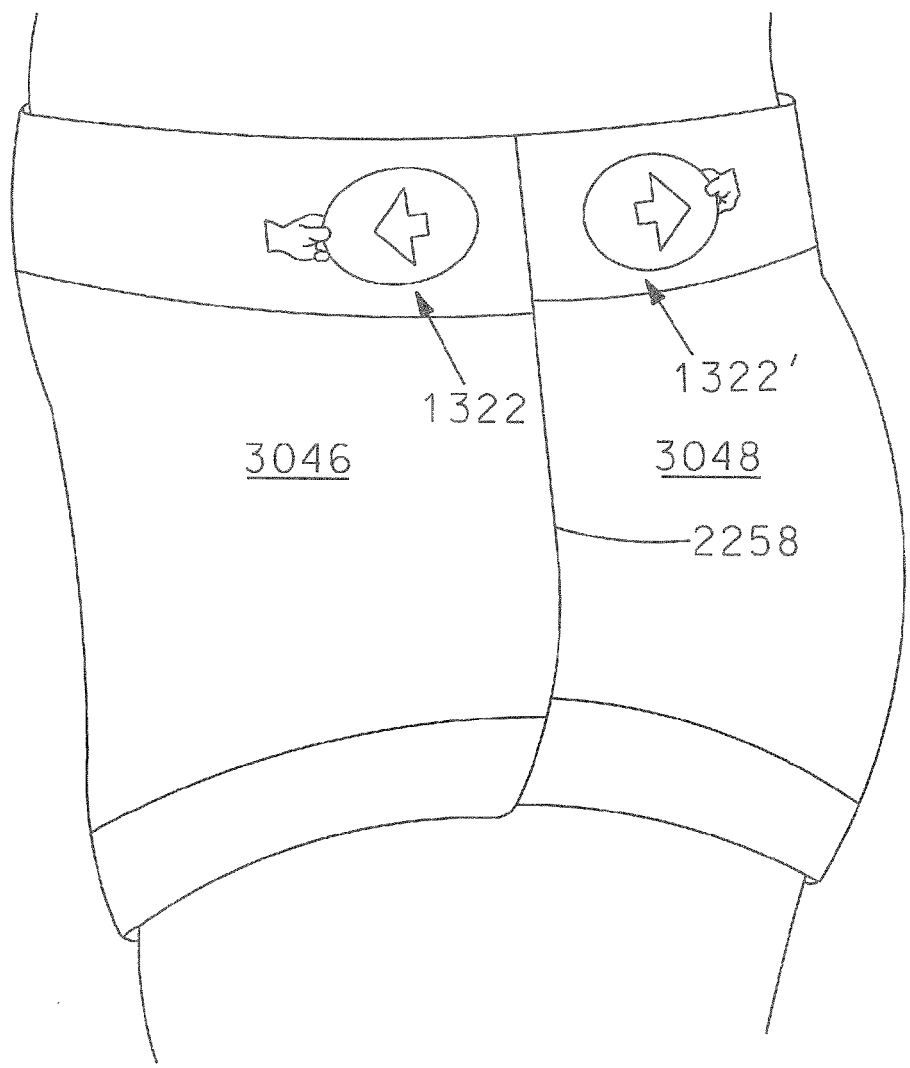
FIG. 19 is a side view of an embodiment of an absorbent article of the present invention in use.
Figure 20:
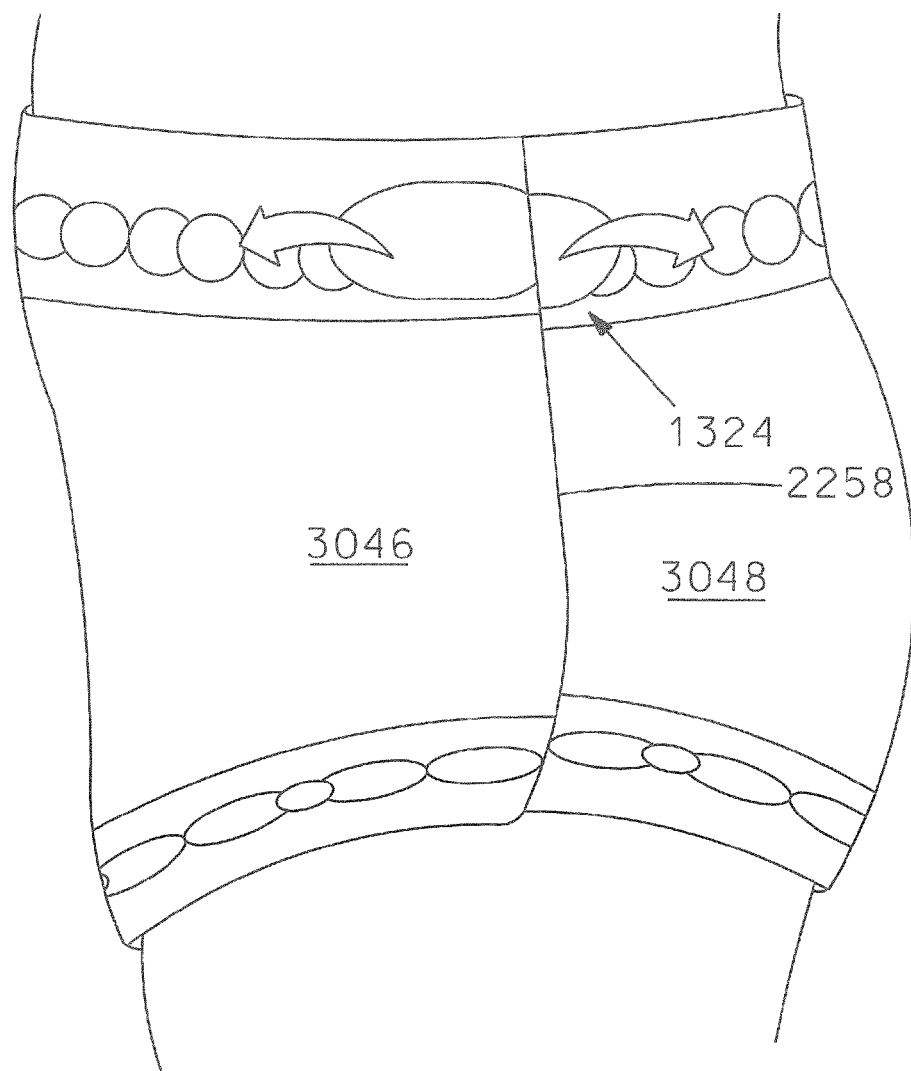
FIG. 20 is a side view of the absorbent article of FIG. 19 comprising alternate graphics.

Additionally, graphics (e.g., 10) may be instructional (see FIGS. 19 and 20). For instance, graphics (e.g., 10) may illustrate how to attach or detach absorbent article components (e.g., 256) to or from one another. Graphics (e.g., 10) which are instructional may include a hand representation 360, a zipper representation, etc. Additionally, referring to FIG. 19, whole graphics 1322 and 1322' which are instructional (providing either a common instruction or two different instructions) may be oriented on each of the ear panels 2146 and 2148, such that each of the whole graphics 1322 and 1322' are on each side of the seam 2258. In FIG. 19, graphics 1322 and 1322' are providing the common instruction of disengaging the side panels 3046 and 3048. Also, one or a plurality of whole graphics (e.g., 1322 and 1322') which are instructional, providing a common instruction, may be located on a single ear panel (e.g., 3046). Still further, referring to FIG. 20, an interrupted graphic 1324 which is instructional, providing a common instruction, may be oriented across the seam 2258 of two side panels 3046 and 3048. Other graphics (e.g., 10) which provide instructions may be found in U.S. patent application Ser. No. 11/541,325 (Ashton et al.) (U.S. Pat. No. 8,066,687), U.S. patent application Ser. No. 11/198,614 (Liu et al.)(U.S. Pub. No. US 2007-0032766, U.S. patent application Ser. No. 11/083,606 (Roe et al.) (U.S. Pat. No. 7,887,522), U.S. patent application Ser. No. 11/083,607 (Roe et al,)(U.S. Pat. No. 7,806,880), and U.S. Patent Publication No. 2005/0096618 (Magee et al.)(U.S. Pat. No. 7,833,212).

Graphics (e.g., 10) may be applied to absorbent article components (e.g., 256) using a number of printing techniques and processes, including, but not limited to, relief printing (including letterpress and flexography), planographic printing (including offset lithography, screenless lithography, collotype, and waterless printing), intaglio printing (including gravure, steel-die, and copper-plate engraving), stencil and screen printing, and electronic printing (including electrostatic, magnetographic, ion or electron deposition, and inkjet printing). Graphics (e.g., 10) may be applied to absorbent article components (e.g., 256) in the absorbent article component's (e.g., 256) relaxed or stretched state (in the case of stretchable, elastic, or extensible graphic absorbent article components (e.g., 260)), as further described in U.S. Pat. No, 5,612,118.

In flexography printing, graphics (e.g., 10) are formed via a raised surface on a printing plate. The raised surface is inked using a uniformly engraved/etched anilox roll. The anilox roll picks up ink from an ink fountain and transports it onto the printing plate. Printing is done by transferring the ink directly from the printing plate to the substrate (e.g., outer cover 22).

Gravure printing is accomplished by cutting, engraving, or etching various sizes and/or depths of minute cells (or wells) below a surface of a plate or cylinder. The cells are flooded and loaded with ink, the excess ink is scraped off the surface of the plate by a doctor blade, and the ink left in the cells is transferred to a substrate. The depth and size of each cell determines the amount of ink that is transferred to the surface of the plate. The nature of the process permits a heavy laydown of ink, which accounts for the rich, saturated colors typical of the gravure process.

The sequence of steps in both floxography and gravure is prepress, press or print, and postpress. The prepress and postpress operations are similar for floxography and gravure including the design, preparation, and assembly of graphics (e.g., 10) for reproduction, the finishing operations to give the final substrate, winding and transportation. The printing press unit has a print cylinder for mounting the plate, an inking system to feed ink to the plate, an impression cylinder to provide backing pressure and support for the substrate as the graphic is printed onto it from the printing plate. The press has a means for feeding the substrate (unwinding unit) into printing units, and a delivery device for collecting the printed substrate (the rewind). The press has as many printing units as the number of colors that it can print (e.g., a four-color press for example has four printing units).

The following graphic (e.g., 10) configurations may be of interest to highlight the dynamic nature of the graphics (e.g., 10):

Graphic Configuration 1

Referring to FIGS. 7A and B, a graphic 1010, 2010, and 3010 may comprise a character's main body 264 and 1264 oriented on the central zone 252 of the absorbent article 20 and the character's arms 266 and 1266 (or other extremities of the character, including legs and tails) extending from the character's main body 264 and 1264 to the side zones 251 of the absorbent article 20. The central zone 252 of the absorbent article 20 generally includes the area bounded by the width (transverse) of the absorbent article 20 in the crotch region 30 to the waist bands 50 in both the front region 26 and the back region 28 forms the waist opening 36. However, the central zone 252, may also be generally defined by a change in an elastic modulus of the zones 250. In this configuration, the side zones 251 may comprise a material (e.g., 124) which is stretchable, elastic, or extensible so that, in use, the character's arms 266 and 1266 may change shape, aspect ratio, or visual appearance as a result of the side zone's 251 elastic modulus during wear or application.

Graphic Configuration 2

Figure 8:
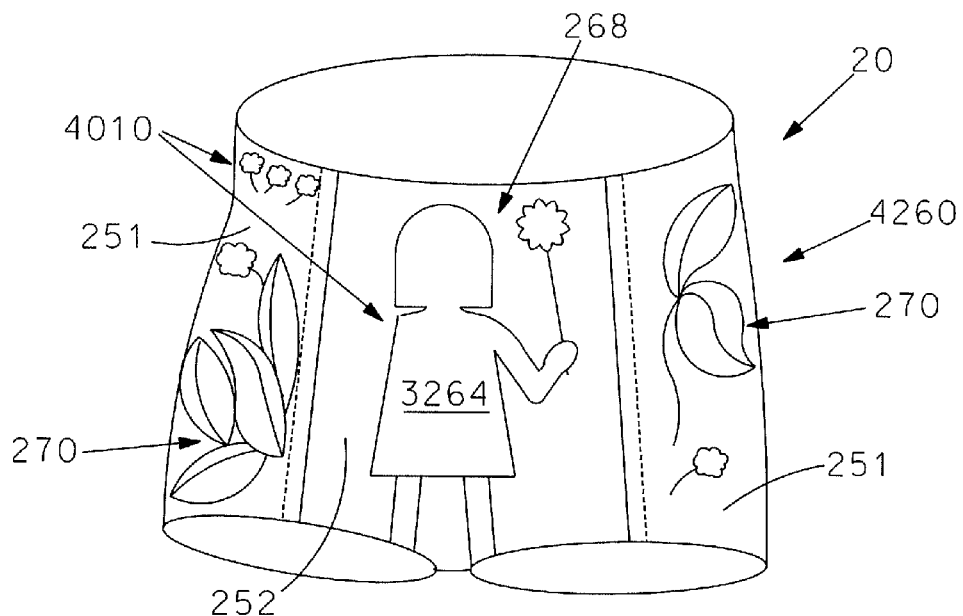
FIG. 8 is a perspective view of the absorbent article of FIG. 1 comprising alternate graphics.

Referring to FIG. 8, a graphic 4010 may comprise a character's main body 3264 oriented on the central zone 252 of the absorbent article 20 and separate, but complementary graphics 4010 may be oriented on the side zones 251 of the absorbent article 20. For instance, a cartoon of a little girl and plant representations 266 may be oriented on the central zone 252 of the absorbent article 20 and flower and plant representations 270 may be oriented on the side zones 251 of the absorbent article 20. This configuration may give the impression that separate zones 250 or components 256 of the absorbent article 20 do not exist.

Graphic Configuration 3

Frames of a story (not shown) may be placed on different zones (e.g., 250) or components (e.g., 256) of an absorbent article (e.g., 20). The story may evolve from frame to frame. For example, a story may start in a frame oriented on a right side zone (e.g., 272 (relative to the wearer)) and may progress (counterclockwise) to a front central zone (e.g., 274), to a left side zone (e.g., 276 (relative to the wearer)), to a back central zone (e.g., 278), and back to the right size zone (e.g., 272). Alternatively, a story may progress in the opposite direction (clockwise), Counterclockwise may be more easily understood by an observer of a wearer. Additionally, it should be understood that graphics (e.g., 10) may be oriented right-side-up (relative to the wearer) or upside-down (relative to the wearer).

Graphic Configuration 4

Figure 9:
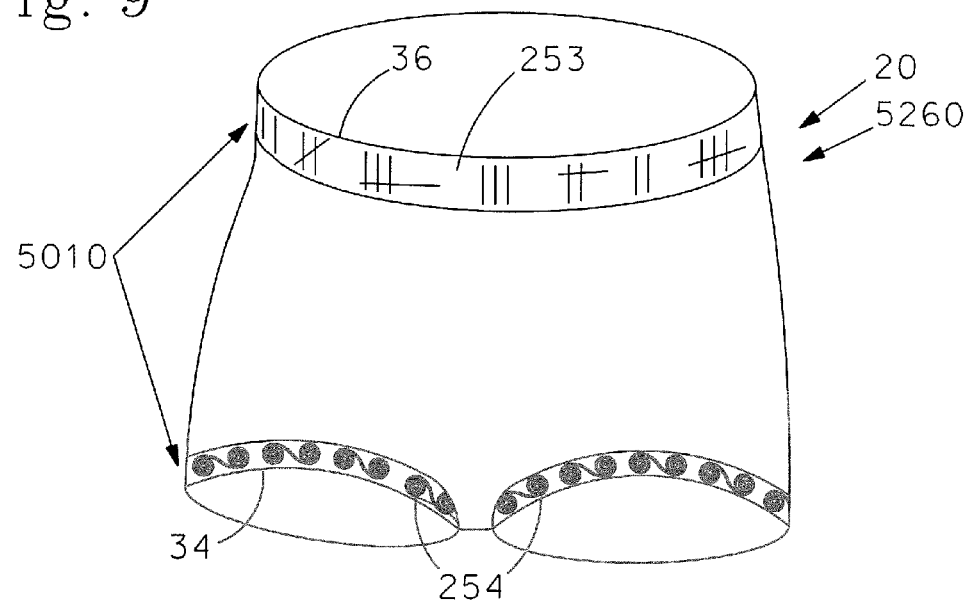
FIG. 9 is a perspective view of the absorbent article of FIG. 1 comprising alternate graphics.

Referring to FIG. 9, graphics 5010 may be oriented in one or both the leg band zones 254 and the waist band zone 253 such that, when the absorbent article 20 is being worn, an element appears to enclose the leg and/or waist openings 34 and 36 of the absorbent article 20. As illustrated FIG. 9, "representative of a leg band" means graphics 5010 that resemble the look of leg bands on male or female underwear boxers, trunks, briefs, or panties. Likewise, as illustrated FIG. 9, "representative of a waist band" means graphics 5010 that resemble the look of waist bands on male or female underwear boxers, briefs, briefs, or panties.

Alternatively, rather than using graphics 5010 to create the appearance of a leg band or a waist band (as they exist on underwear), separate absorbent article components (e.g., 256) may be bonded or fastened to the outer cover 22. Said separate components (e.g., 256) may be functional and/or aesthetic. Said separate components (e.g., 256) may comprise an elastomer and may be stretchable, elastic, or extensible. Said separate components (e.g., 256) may be actual leg and waist bands.

Graphic Configuration 5

Figure 10A:
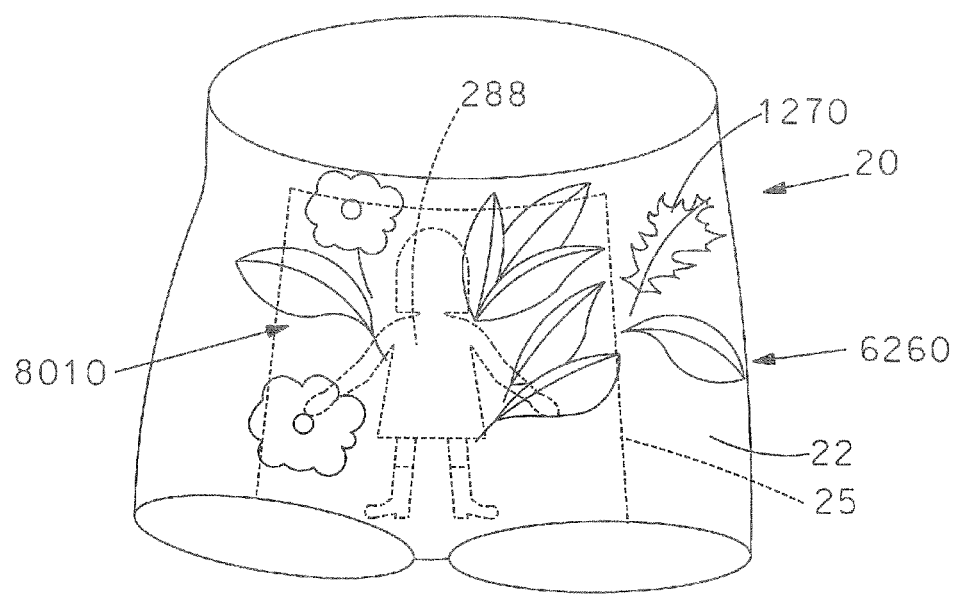
FIGS. 10A-C are perspective views of the absorbent article of FIG. 1 comprising alternate graphics.
Figure 10B:
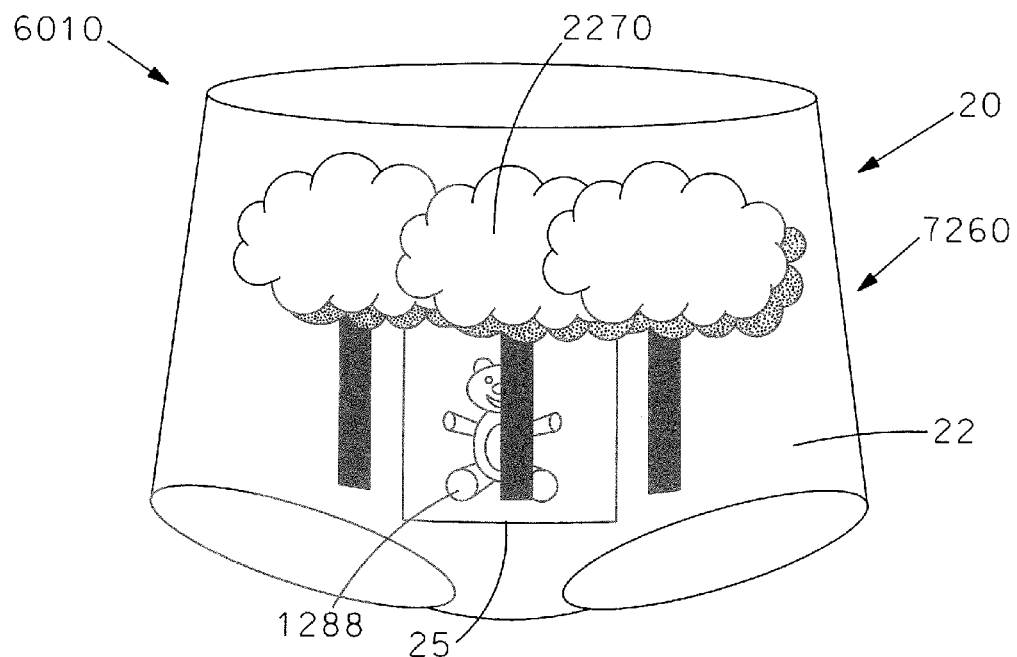
Figure 10C:
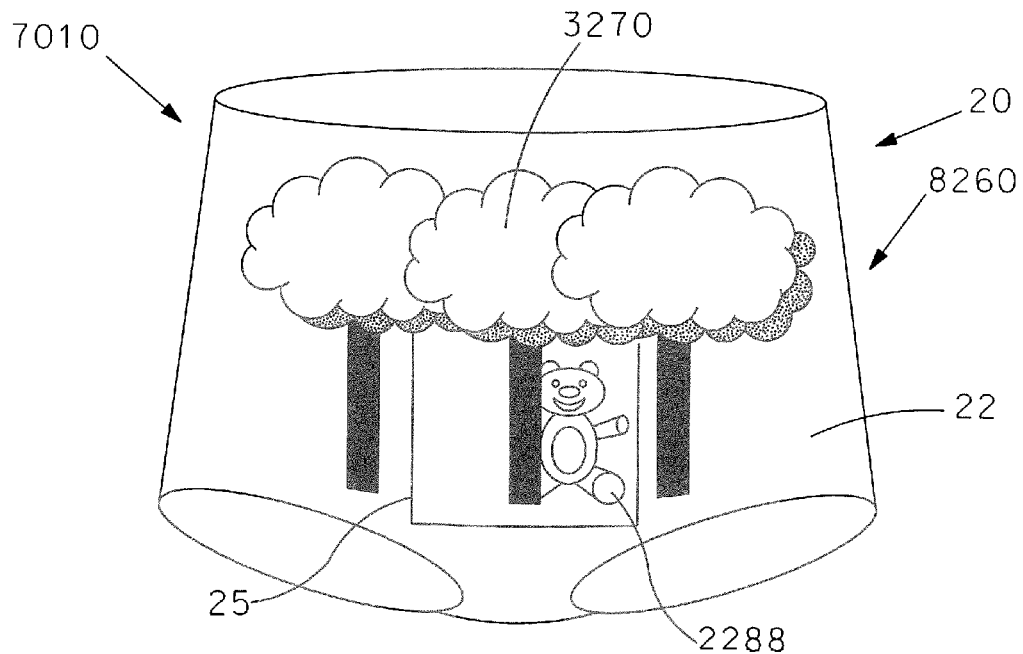

Referring to FIGS. 10A-C, multiple graphic absorbent article components 6260, 7260, and 8260 may be oriented in an overlapping manner such that at least portions of graphics 6010, 7010, and 8010 of overlapped component 6260, 7260, and 8260 can be seen through the overlapping component 6260, 7260, and 8260. Further, portions of the graphic absorbent article components 6260, 7260, and 8260 may be connected to each other such that the graphic absorbent article components 6260, 7260, and 8260 are capable of moving relative to each other as the absorbent article 20 is being worn by a wearer. For example, a character graphic 288, 1288, and 2288 (or a portion thereof) may be oriented on the absorbent core 25 and flower and plant representations 1270, 2270, and 3270 may be oriented on the outer cover 22 such that when the absorbent article 20 is worn, the outer cover 22 moves relative to the absorbent core 20, and, because one is able to at least partially see the character graphic 288, 1288, and 2288 on the core 20 through the outer cover 22, it appears to that the character graphic 288, 1288, and 2288 is peeking out between the flower and plant representations 1270, 2270, and 3270.

In order to achieve a more underwear-like absorbent article (e.g., 20), graphic absorbent article components (e.g., 260) may be complemented by additional absorbent article (e.g., 20) features (not shown), including, but not limited to, a robust leg band or waist band feature (see U.S. Pat. No. 5,064,421), a narrow crotch dimension (from about 7 cm to about 16 cm, or from about 10 cm to about 12 cm), an outer cover that comprises an elastomeric material, such that it conforms to the shape of the wearer, a fixed side seam (see U.S. Pat. No. 5,779,831), a visual or physical tag on the article (including, garment care instruction tags, garment composition tags), and an absorbent article shape that is created to closely follow the anatomical dimensions of the wearer.

An absorbent article (e.g., 20) may comprise graphics (e.g., 10) on a substantial portion of the surface area of the inner and/or outer-facing surface (e.g., 24 and 22) of the absorbent article (e.g., 20). The surface area of the absorbent article (e.g., 20) would be defined as the area which is visible to the eye when the article is stretched out on a flat surface. This would apply for both the inner and/or outer-facing surface (e.g., 24 and 22) of the absorbent article (e.g., 20).

For example, an absorbent article (e.g., 20) may comprise graphics (e.g., 10) on at least about 50%, about 75%, about 85%. about 90%, about 95%, or about 100% of its viewable outer surface. An absorbent article (e.g., 20) may comprise graphics (e.g., 10) on at least about 50%, about 75%, about 85%, about 90%, about 95%, or about 100% of its viewable inner surface. An absorbent article (e.g., 20) may comprise graphics (e.g., 10) on at least about 50%, about 75%, about 85%, about 90%, about 95%, or about 100% of its combined viewable inner and outer surfaces.

Alternatively an absorbent article (e.g., 20) may not comprise graphics (e.g., 10) on a substantial portion of the surface area of the inner and/or outer-facing surface (e.g., 24 and 22) of the absorbent article 20, but may comprise graphics (e.g., 10) on several absorbent article components and/or zones (e.g., 256 and/or 250) over the surface area of the viewable inner and/or outer-facing surfaces in a format which gives the impression that graphics (e.g., 10) are on a substantial. portion of the surface area of the inner and/or outer-facing surface (e.g., 24 and 22) of the absorbent article 20.

For example, an absorbent article (e.g., 20) may comprise graphics (e.g., 10) on at least about 25%, about 50%, 75%, about 85%, about 90%, about 95%, or about 100% of its viewable outer absorbent article components. For instance, as illustrated in FIG. 10-A, the graphics 8010 on the absorbent core 25, as well as the graphics 8010 on the outer cover 22 are viewable, and should be considered viewable outer absorbent article components comprising graphics. An absorbent article (e.g., 20) may comprise graphics (e.g., 10) on at least about 25%, about 50%, about 75%, about 85%, about 90%, about 95%, or about 100% of its viewable inner absorbent article components. An absorbent article (e.g., 20) may comprise graphics (e.g., 10) on at least about 25%, about 50%, about 75%, about 85%, about 90%, about 95%, or about 100% of its combined viewable inner and outer absorbent article components.

For example, an absorbent article (e.g., 20) may comprise graphics (e.g., 10) on at least about 25%, about 50%, 75%, about 85%, about 90%, about 95%, or about 100% of its viewable outer absorbent article zones. An absorbent article (e.g., 20) may comprise graphics (e.g., 10) on at least about 25%, about 50%, about 75%, about 85%, about 90%, about or about 100% of its viewable inner absorbent article zones. An absorbent article (e.g., 20) may comprise graphics (e.g., 10) on at least about 25%, about 50%, about 75%, about 85%, about 90%, about 95%, or about 100% of its combined viewable inner and outer absorbent article zones.

Absorbent articles (e.g., 20) of the present invention may comprise a continuous or substantially continuous outer cover (e.g., 22) to which graphics (e.g., 10) are applied. The outer cover (e.g., 22) may then be cut for shape purposes in a final finishing process before it is formed as part of the finished absorbent article (e.g., 20). In order to preserve the design integrity of the graphics (e.g., 10) on a finished absorbent article (e.g., 20), the outer cover (e.g., 22) may be cut in the final finishing process at a precise point of the outer cover (e.g., 22). Methods and equipment for constructing such absorbent articles (e.g., 20) may be found in U.S. Pat. Nos. 5,569,234 and 5,659,538. An advantage to constructing the absorbent article (e.g., 20) with a continuous graphic absorbent article component (e.g., 260) is a lower number of visible seams (e.g., 258).

Figure 11:
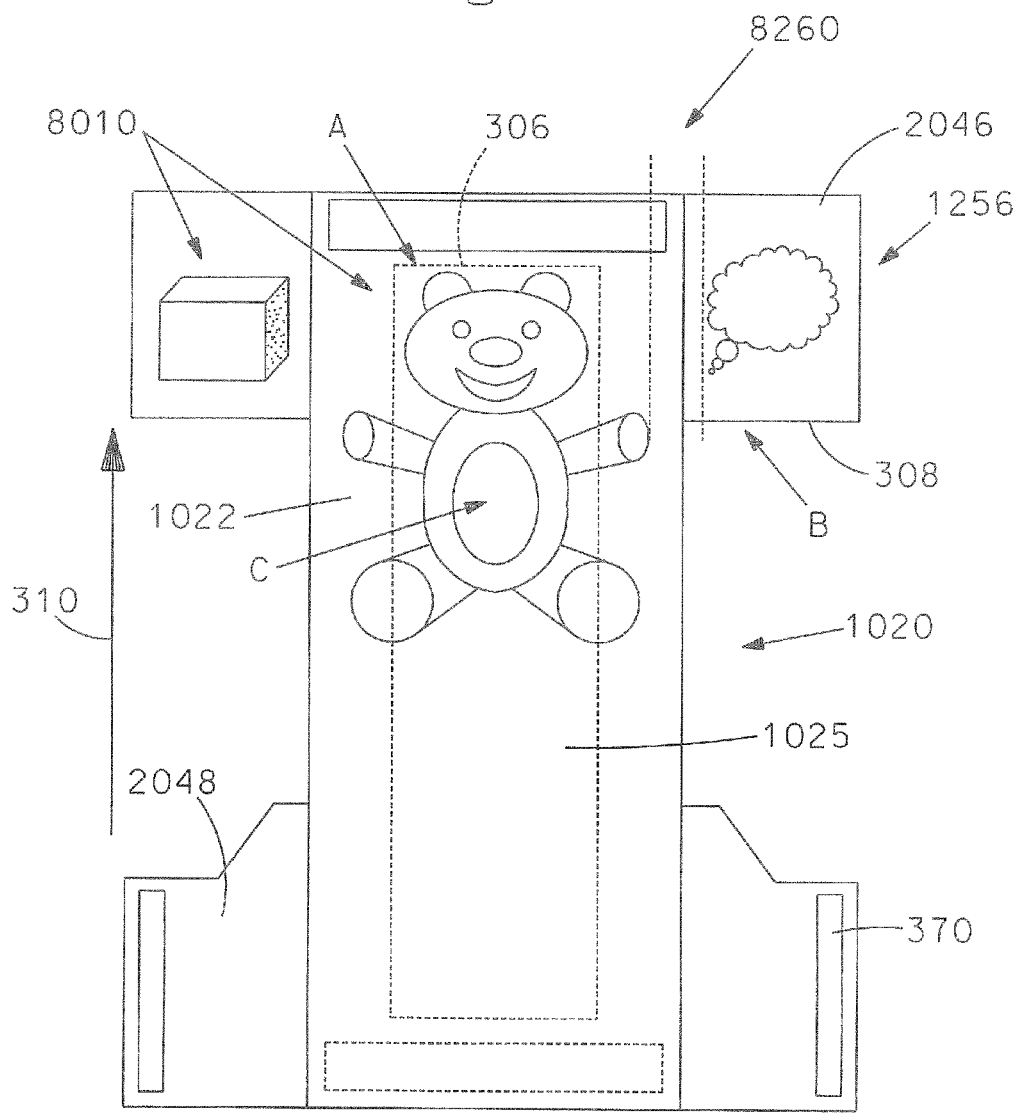
FIG. 11 is a plan view of an embodiment of an absorbent article of the present invention.

Absorbent articles (e.g., 20) of the present invention may utilize one or more components located in a central zone (e.g., 252) for attaching graphic absorbent article components (e.g., 260) to (see FIG. 11). Graphic absorbent article components (e.g., 260) may be attached such that the graphic absorbent article components (e.g., 260) are entirely contained within the area of a central zone (e.g., 252) or such that one or more edges of a graphic absorbent article components (e.g., 260) are attached to one or more components located in a central zone (e.g., 252). Methods and equipment for constructing such absorbent articles are described in U.S. Pat. Nos. 4,940,464 and 5,224,405. Particularly, a method of constructing an absorbent article may comprise the step of attaching first, second, third, fourth, and fifth absorbent article components, such that at least four seams are formed (the absorbent article may comprise six seams). The method may also comprise applying a printing technique to the first, second, third, fourth, and fifth absorbent article components, such that graphics are applied to each of the first, second, third, fourth, and fifth absorbent article components. Further regarding the method of constructing the absorbent article, graphics may be applied to different absorbent article components utilizing different printing techniques selected from printing, plano graphic printing, intaglio printing, stencil and screen printing, and electronic printing. A first printing technique may be applied to the absorbent article component in a relaxed state and a second printing technique may be applied to a second absorbent article component in a stretched state. In one embodiment, a first printing technique is used on at least one of a first, second, third, and fourth graphic absorbent article components, and a second printing technique is used on a fifth graphic absorbent article component. In another embodiment, the appearance of a waistband is printed in a waistband zone and the appearance of a legband is printed in a legband zone.

In order to ensure that absorbent article components (e.g., 256 (including graphic absorbent article components (e.g., 260)) are properly oriented when attached to other absorbent article components (e.g., 256), registration may be used. Registration may include using a system (e.g., 298, see FIG. 12) to detect a location (e.g., A, B, and C, see FIG. 11) on an absorbent article component (e.g., 256) and to compare the location (e.g., A, B, and C) against a set point (which may be an operator desired or machine set location). The system (e.g., 298) may adjust placement of the absorbent article component (e.g., 256) in accordance with said comparison. For example, the location (e.g., A, B, and C) of a series of graphics (e.g., 10) on an outer cover (e.g., 22) may be detected and a repeat length of the graphics (e.g., 10) may be altered via a length control system (not shown, but described in U.S. Pat. Nos. 6,444,064 and 6,955,733). Alternatively, a system (e.g., 298) may be used to detect and control the longitudinal or machine direction position of a component (e.g., 256) relative to a desired position on the absorbent article (e.g., 20) wherein the position at which subsequent occurrences of a first component (e.g., 256) is attached to a second component (e.g., 256) is altered to ensure the first component (e.g., 256) is in the desired location. Such can be performed based on multiple detections and the use of an average position, deviation from the desired position, or by detecting less frequently than every occurrence.

Additionally, a system (e.g., 298) may detect a first location (e.g., A) on a first absorbent article component (e.g., 256) and a second location (e.g., B), on a second absorbent article component (e.g., 256). The first and second locations may be compared relative to each other and against a set point or desired offset position. The system (e.g., 298) may adjust placement of the first and/or second absorbent article components in accordance with said comparison. For example, a through beam vision system may take an image of the absorbent article (e.g., 20), determine a first location (e.g., A) of a leading edge (e.g., 306, see FIG. 11) of an absorbent core (e.g., 1025), and a second location (e.g., B) of a trailing edge (e.g., 308) at ear panel (e.g., 2046). Said system (e.g., 298) may then determine the difference in position between the two absorbent article components in the machine direction (e.g., 310) and compare the difference against a set point or desired offset. Based on the difference between the comparison and the set point, the system (e.g., 298) may determine that a corrective action is required and initiate that corrective action to change the relative position of the ear panel (e.g., 2046) on subsequent absorbent articles (e.g., 20).

It may be desirable to use a combination of detection methods. For example, a photographic image system (e.g., 302) may be used to detect one or more locations (e.g., A, B, and C) on an outer-facing absorbent article component (e.g., 256), such as an outer cover (e.g., 1022) and a through beam radiation system (e.g., 300) may be used to detect one or more locations (e.g., A, B, and C) on an inner absorbent article component (e.g., 256), such as a topsheet (e.g., 24). Additionally, it may be possible to detect graphics (e.g., 8010) with a photo eye or photo optic. For example, a photographic image system (e.g., 302) may be used to detect a graphic (e.g., 8010) location (e.g., C) on an outer cover (e.g., 1022), and a graphic (e.g., 8010) on an ear panel (e.g., 2046), while a through beam system (e.g., 300) could detect the position of an absorbent core (e.g., 25).

Figure 12:
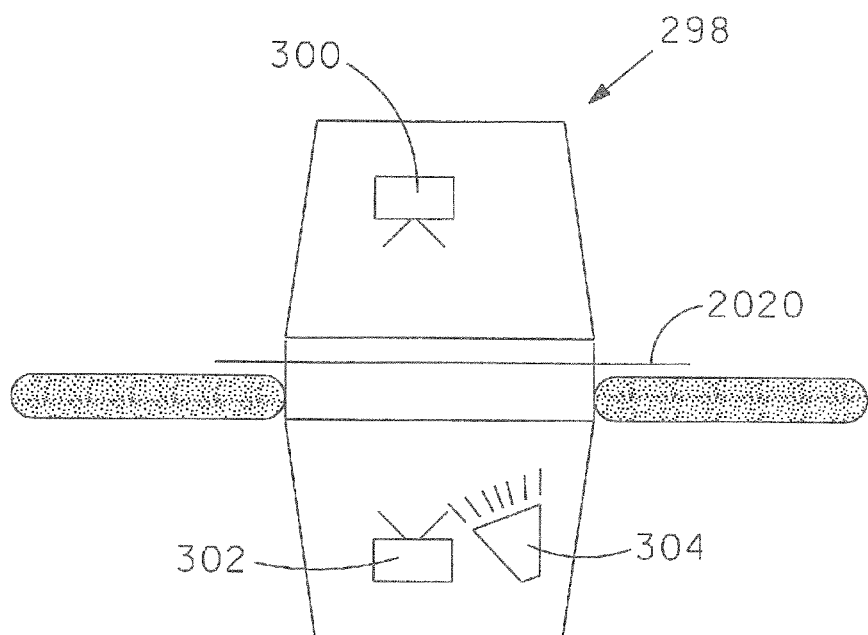
FIG. 12 is a cross-sectional side view of a machine vision system comprising the absorbent article of FIG. 11.

Referring to FIGS. 11 and 12, a system 298 may detect a location A, B, and C on each of three or more absorbent article components 1256. The detected locations A, B, and C may be compared against one or more set points. The detected locations A, B, and C may also be compared relative to each other and then against one or more set points. The system 298 may adjust placement of two or more of the detected absorbent article components 1256 in accordance with said comparison. For example, as illustrated in FIG. 12, a machine vision system 298 comprising two vision capture devices 300 and 302 may be used. One vision capture device 300 may be located on the opposite side of a light emitting device 304, and one capture device 302 may be located on the same side as the light emitting device 304. In this example, the vision capture device 300 on the opposite side of the light emitting device may generate a through beam image to determine the location of, for example, an edge 306 of an absorbent core 1025 and an edge 308 of an ear panel 2046. The vision capture device 302 on the same side as the light emitting device 304 may generate a reflected image to determine the location of graphics 8010 on an outer cover 1022 of the absorbent article 1020. The resulting images may be processed to determine the absolute and relative positions of the three locations A, B, and C and the positions could be compared to each other and against a set point or desired offset. From the comparison of the relative component 1256 positions and the set points or desired offsets, the system 298 would determine if a corrective action is required. If a corrective action is required, the system may initiate the corrective action for one or more of the components 1256 to ensure the absolute or relative positions of the components 1256 on subsequent absorbent articles 1020 is within the set point or desired offset tolerances.

Examples of components 1256 on which one or more locations A, B, and C could be detected and processed using such a system 298 may include, but not be limited to, an absorbent core (e.g., 1025), an ear panel (e.g., 2046, 2048), a landing zone, a topsheet (e.g., 24), an acquisition layer, a core cover, a fastener (e.g., 370), a dusting layer, a body side liner, an outer cover (e.g., 1022), a core outer layer, waist members (e.g., 50), leg cuffs (e.g., 52), wetness sensation liners, a waist pocket member, a sensor or indicator (including wetness and fit), a sustained fit element, a stiffener, a removable absorbent member, an anchoring band, or other components (e.g., 1256) that may be detected using through beam, photo eye, or reflected image vision systems. Possible combinations of components could include, but not be limited to, the following component combination sets: (1) an absorbent core (e.g., 1025), an ear panel (e.g., 2046 and 2048), a graphic (e.g., 8010) on an outer cover (e.g., 1022); (2) an ear panel (e.g., 2046 and 2048), a graphic (e.g., 8010) on an outer cover (e.g., 1022), a waist member (e.g., 50); (3) an absorbent core (e.g., 1025), an ear panel (e.g., 2046 and 2048), a waist member (e.g., 50); (4) a graphic (e.g., 8010) on an outer cover (e.g., 1022), an ear panel (e.g., 2046 and 2048), a graphic (e.g., 8010) on a waist member (e.g., 50); (5) combinations of "(1)" through "(4)" within this paragraph, as well as those combinations readily apparent to those skilled in the art.

Beyond using the above registration systems (e.g., 298), it may be desirable to control the inline position of graphics (e.g., 8010 (see U.S. Pat. No. 6,444,064)) into a discrete absorbent article component placement device (see U.S. Pat. No. 5,224,405) to ensure the placement device does not cut through, disturb, or otherwise negatively impact the graphics (e.g., 8010) on the absorbent article component (e.g., 1256) being applied by the placement device. This method may be combined with a system (e.g., 298) which ensures the proper placement of the absorbent article components (e.g., 1256) described above or with similar systems (e.g., 298). Said combination may be used to produce an absorbent article (e.g., 1020) comprising graphics (e.g., 8010) aligned relative to each other such that the absorbent article (e.g., 1020) appears more holistic and garment-like.

It may be further (or alternatively,) desirable to combine the above registration systems (e.g., 298) and methods with the methods described in U.S. Pat. Nos. 5,659,538, 7,123, 981, 5,359,525, 6,743,314, 5659538, 6,957,160, 5,980,087, 6,253,159, 6,266,436 and 6,224,699.

Beyond considerations related to the physical construction of absorbent article components (e.g., 256), such as choice of absorbent article construction, registration, etc., there are several design considerations for overcoming the negative impact seams (e.g., 1258) may create for an absorbent article (e.g., 20) designed to appear more holistic and garment-like.

Referring to FIG. 13, a graphic 9010 may comprise wavy lines 306 (including undulating or irregular lines) on the back ear panel 2048 which overlaps the front ear panel 2046 comprising wavy lines 306 to form a seam 1258. Wavy lines 306 on each of the ear panels 2048 and 2046 may be used to disguise any misalignment of the first and second graphic absorbent article components 9260.

Figure 14A:
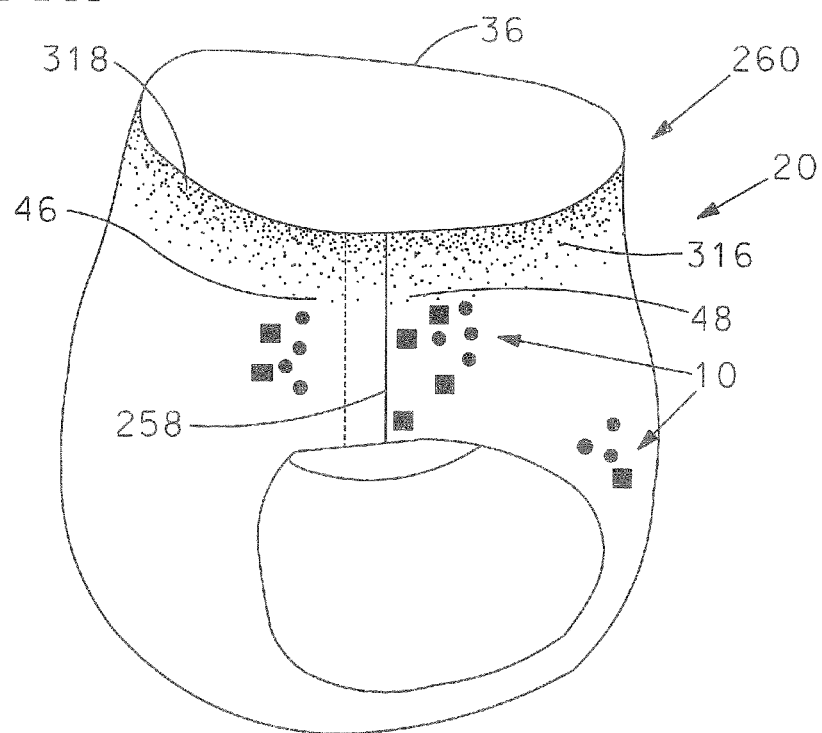
FIGS. 14A-C are perspective views of the absorbent article of FIG. 1 illustrating various color gradations.
Figure 14B:
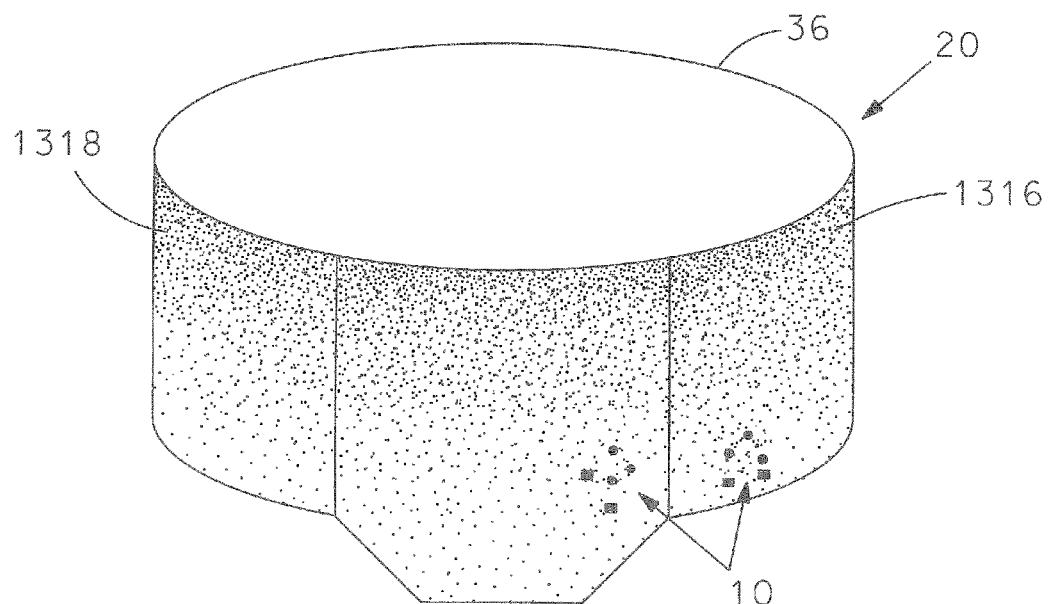
Figure 14C:
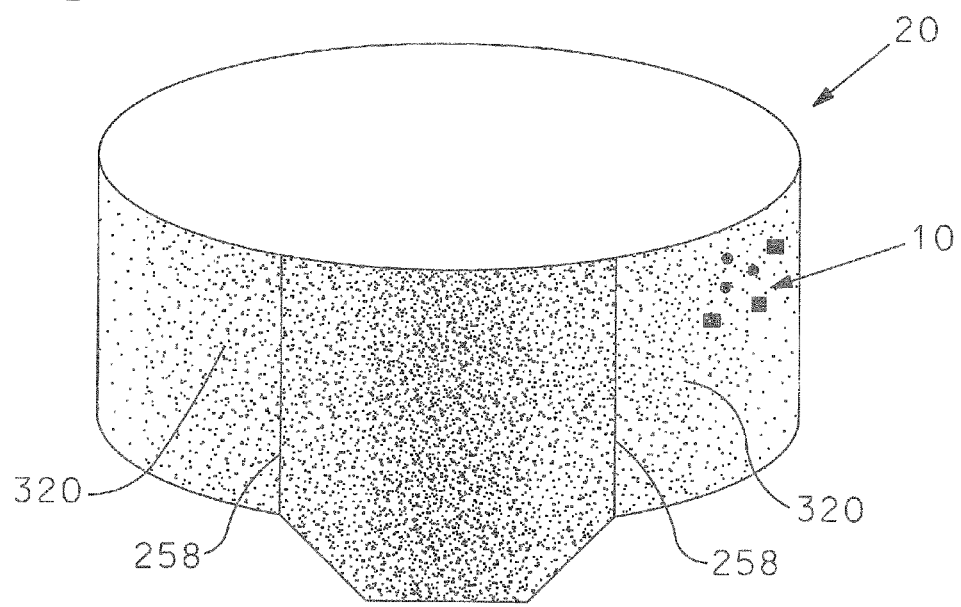

Referring to FIG. 14-A, graphic absorbent article components 260 may comprise color fields 316 and 318 which is not part of the graphic 10. More specifically, the front ear 46 may comprise the color field 316 which gradates and which may overlap the back ear 48 comprising the color field 318 which gradates. Further, the color fields 316 and 318 on the ear panels 48 and 46 may be similar for the purpose of disguising any misalignment of the ear panels 48 and 46. Further, as illustrated in FIGS. 14A and B, color fields 316, 1316, 318, and 1318 may run along the waist opening 36, in the waist band zone 253, and graduate in the transverse direction away from the waist opening 36. FIG. 14-C illustrates a color field 320 which runs in the longitudinal direction along the seams 258, and which gradates in the transverse direction away from the seam 258. Similarly gradating color fields (e.g., 316, 318, 1316, 1318, and 320) may help to disguise any misalignment of the graphic absorbent article components 260.

Figure 15A:
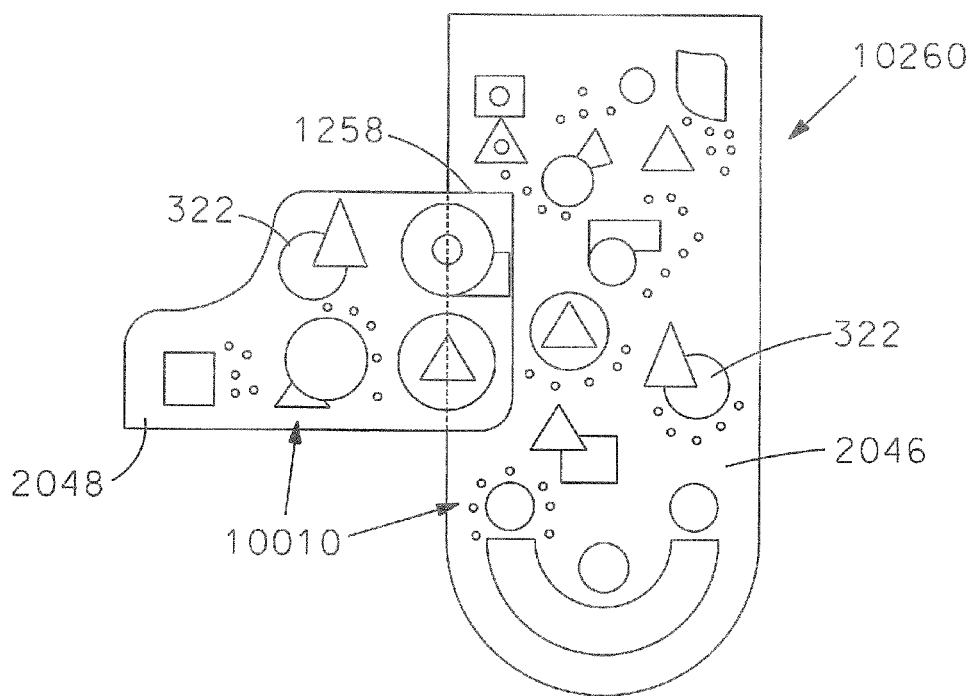
FIG. 15A is a partial side view of the absorbent article of FIG. 11, wherein the ear panels are shown overlapping, wherein the ear panels comprise alternate graphics.
Figure 15B:
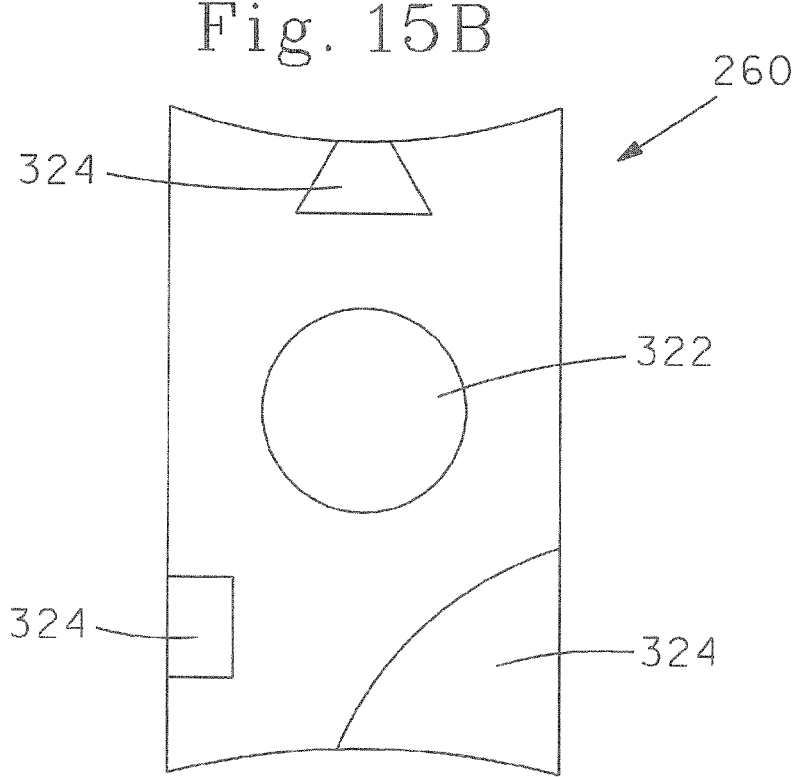
FIGS. 15B-C are plan views of an ear panel of the absorbent article of FIG. 11.
Figure 15C:
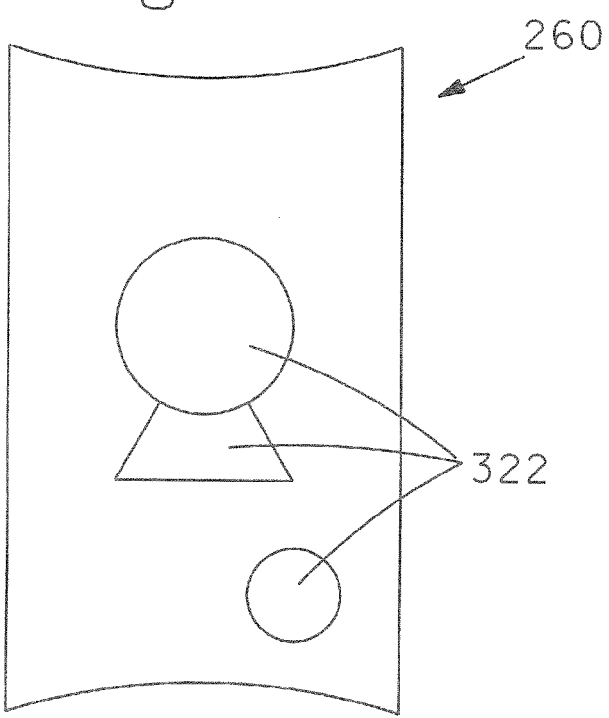

Referring to FIGS. 15A and 15B, a graphic 10010 may comprise whole graphics 322 on the back ear panel 2048 which overlaps the front ear panel 2046 comprising whole graphics 322 to form a seam 1258. This alone will enhance the garment like appearance of the final absorbent article (e.g., 1020). Further, each of the whole graphics 322 may be oriented on each of the respective graphic absorbent article components 10260 such that no whole graphics 322 are interrupted (cut-off like as graphics 324 are, as illustrated by FIG. 15C) by the overlapping of the first and second graphic absorbent article components 10260.

Figure 16A:
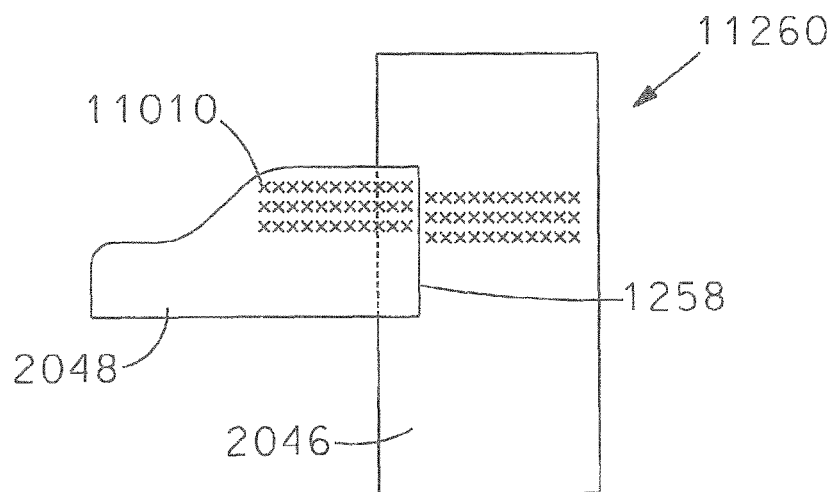
FIGS. 16A-B are partial side views of the absorbent article of FIG. 11, wherein the ear panels are shown overlapping, wherein the ear panels comprise alternate graphics.
Figure 16B:
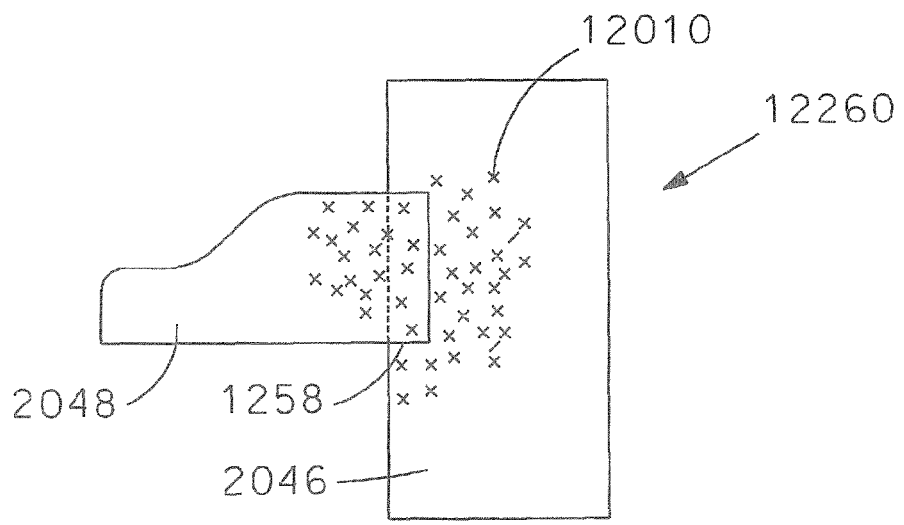

Referring to FIGS. 16A and B, graphics 11010 and 12010 may be oriented on graphic absorbent article components 11260 and 12260 in an organized (uniform and symmetrical) or random fashion. Random orientation of graphics 12010 on the back ear panel 2048 which overlaps the front ear panel 2046 which comprises randomly oriented graphics 12010 may disguise any misalignment of graphics 12010 which are interrupted by finishing processes and/or by seams 1258 (versus organized graphics 11010). Random orientation of graphics 12010 on graphic absorbent article components 12260 may appear more garment like and may be offer synergy with graphic absorbent article components (e.g., 10260) comprising only whole graphics (e.g., 322).

Figure 17:
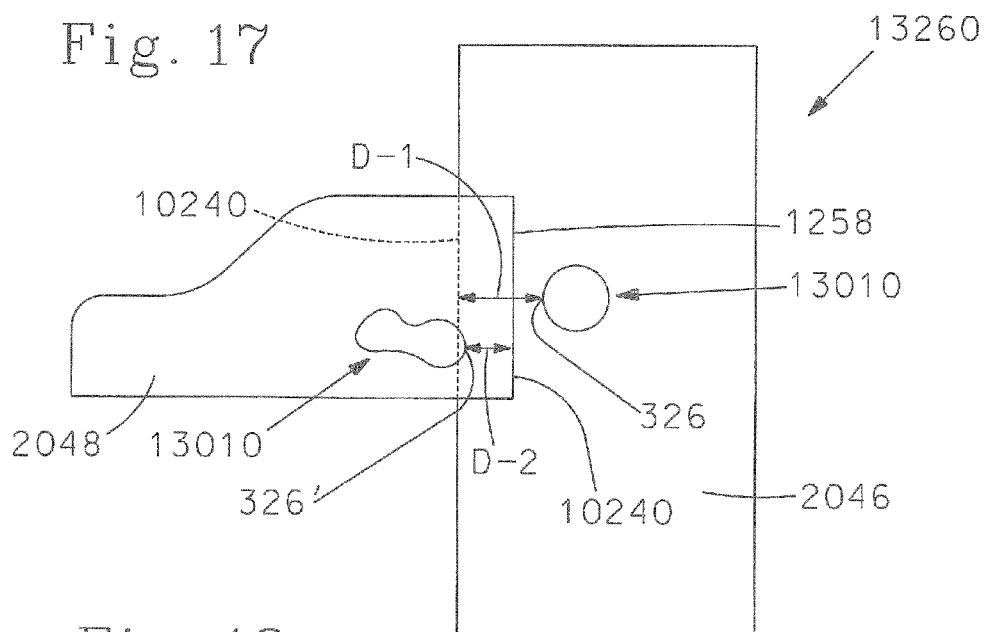
FIG. 17 is a partial side view of the absorbent article of FIG. 11, wherein the ear panels are shown overlapping, wherein the ear panels comprise alternate graphics, and wherein a seam margin is illustrated.

Referring to FIG. 17, the impact of the seam 1258 may also be lessened by keeping the distance between a graphic 13010 and the seam 1258 small. More specifically, it may be desirable to (1) keep a distal point 326 on the graphic 13010 close (between about 2 cm and about 0.2 cm, between about 1.7 cm and about 0.5 cm, between about 1.5 cm to about 0.7 cm, between about 1.2 cm and about 1 cm) to an overlapped edge 10240 of the front ear panel 2046, Distance D-1, and/or (2) keep a distal point 326' on the graphic 13010 (between about 2 cm and about 0.2 cm, between about 1.7 cm and about 0.5 cm, between about 1.5 cm to about 0.7 cm, between about 1.2 cm and about 1 cm) to an overlapping edge 10240 of the back ear panel 2048, Distance. D-2. Because of standard deviations in the manufacturing process, particularly as a first graphic absorbent article component (e.g., 13260) is attached to a second graphic absorbent article component (e.g., 13260), getting a graphic too close to the seam margin may result in a cut-off graphic (e.g., 324).

A color of a first graphic absorbent article component (e.g., 13260), whether part of the graphic (e.g., 13010) or a color field (e.g., 318), may be matched to a color of a second graphic absorbent article component (e.g., 13260), whether part of the graphic (e.g., 13010) or a color field (e.g., 318). Said color match may be based on a CMC ΔE (ASTM D2244-05), such that no difference is readily discernible to the eye across a seam (e.g., 1258). U.S. Pat. Pub. No. 2006/0025737 describes color matching in greater detail.

The appearance of a waistband (e.g., graphic 5010 in the waist band zone 253) may take attention away from seams (e.g., 1258) of an absorbent article (e.g., 1020). The visual appearance of a waistband (e.g., graphic 5010 in the waist band zone 253) on an absorbent article (e.g., 1020) may be created or highlighted by a color field (e.g., 318) or graphic (e.g., 5010) generally in the waist band zone (e.g., 253). This may be accomplished multiple ways, including coloring elastic strands or a film in the waist band zone (e.g., 25), printing a colored band or graphic (e.g., 5010) in the waist band zone (e.g., 253), printing a color gradation (e.g., 318) in the waist band zone (e.g., 253), tinting a base substrate (e.g., a nonwoven) in the waist band zone (e.g., 253), or placing a single colored component (e.g., 1256) all the way around the absorbent article (e.g., 20) in the waist had zone (e.g., 253).

One or more seams (e.g., 1258) of an absorbent article (e.g., 1020) may be hidden by printing or coloring the plurality of absorbent article components (e.g., 1256) after some or all of them have been assembled. Such may be accomplished using a contact printing method (e.g., gravure, flexography, dyeing, etc.) or with a non-contact method (e.g., ink jet printing). The benefit of a non-contact method is that the printing or coloring would be less sensitive to the surface texture of the absorbent article components (e.g., 1256) being printed on. The seam (e.g., 1258) would be directly printed across, eliminating or significantly minimizing the presence of any discontinuity between the connected absorbent article components (e.g., 1256).

Figure 18:
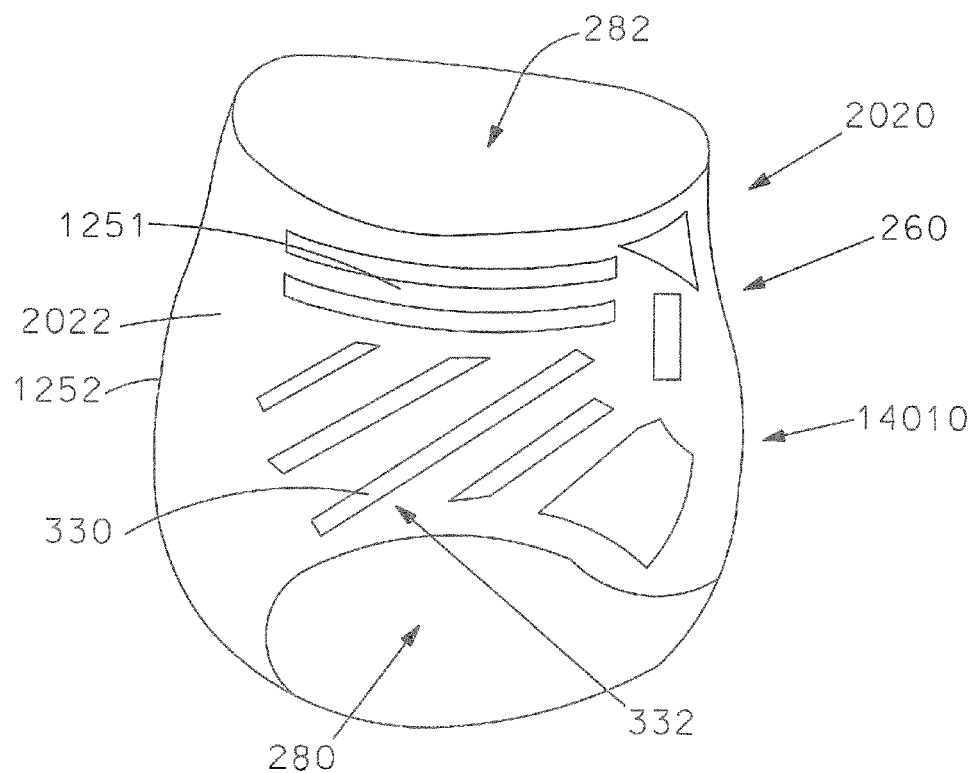
FIG. 18 is a perspective view of an embodiment of an absorbent article of the present invention.

In some instances, as illustrated in FIG. 18, an absorbent article 2020 construction may decrease or eliminate seams (e.g., 1258). For instance, an outer cover 2022 may cover most or all of the seams (e.g., 1258) of the absorbent article 2020. Additionally, instead of having ear panels (e.g., 2048 and 2046) which meet each other to form a seam (e.g., 1258) in the middle of a side zone 1251, a single piece ear panel may be used such that seams (e.g., 1258) border the transition from the side zone 1251 to the central zone 1252. These seams (e.g., 1258) may be reattachable detachable.

It may, in such cases, be desirable to design graphics 14010 which highlight the lack of a seam (e.g., 1258), it may desirable to implement designs in seamless areas that would be impractical to implement across a seam ((e.g., 1258) due to unacceptable appearance). The lack of a seam (e.g., 1258) may be highlighted by various design elements, including, but not limited to, transverse lines 330, diagonal patterns 332, and multi-color repeat patterns.

In cases where a seam is present, the above techniques may be used to lessen the appearance of the seam. One may desire to measure the effectiveness of the techniques. Described in more detail below is a consumer method to perform this evaluation. Particularly, the below consumer method may be used to determine a Seam Noticeability Rating (SNR).

An SNR measures the visual impact of a seam formed in a side zone or a seam formed between the side zone and a central zone. The visual impact of seams impacts the consumer perception of underwear-likeness. Several factors affect the SNR, including, but not limited to, pattern, scale, vertical spacing, horizontal spacing, vertical offset, horizontal overlap, contrast, and level of stretch. And, there may be interactions between two or more of the factors.

It may be desirable to have an SNR of less than about 7 for one or more seams, including a seam formed in a side zone, and including a seam formed between a zone and a central zone of the absorbent article. Further, it may be desirable for the SNR of a seam to be less than about 6, about 5, about 4, or about 3.

The outer cover (e.g., 22) may also be used to help create an absorbent article (e.g., 20) that is more underwear like. Outer covers (e.g., 22) of the present invention may be entirely or partially stretchable or elastic in one or more directions. The outer cover (e.g., 22) may be impervious to liquids (e.g., urine) and manufactured from a thin plastic film or a nonwoven web, although other flexible liquid impervious materials that are compliant and will readily conform to the general shape and contours of the human body can also be used. Additionally, in some embodiments, the outer cover (e.g., 22) may comprise a laminated structure.

The outer cover (e.g., 22) may be generally positioned such that it can be at least a portion of the garment-facing surface of the absorbent article (e.g., 20). The outer cover (e.g., 22) can prevent the exudates absorbed and contained within the absorbent article (e.g., 20) from soiling articles that can contact the absorbent article (e.g., 20), such as bed sheets and undergarments, in some embodiments. Suitable outer cover materials include films such as those manufactured by Tredegar Industries Inc. of Terre Haute, Ind. and sold under the trade names X15306, X10962, and X10964. In various embodiments, the outer cover (e.g., 22) can include an inelastic nonwoven. The outer cover (e.g., 22) can be a thermoplastic film having a thickness of from about 0.012 mm (0.5 mil) to about 0.051 mm (2.0 mils). Another example of a suitable film which can be utilized in the outer cover (e.g., 22) includes a 0.5-1.0 mil (0.0005"-0.001") thick Vistamaxx (elastomeric polypropylene from ExxonMobil). Example elastomeric polypropylene-based compositions are disclosed in PCT App. Nos. WO 2005/052052 and WO 2005/097031. The elastomeric composition may also include fillers like titanium dioxide for improving opacity and calcium carbonate for breathability. The elastomeric polypropylenes may also be blended with styrenic block copolymers, semicrystalline polyolefins or sub-micron inorganic particles.

In some embodiments, the outer cover (e.g., 22) may comprise an elastic nonwoven. In some embodiments, the outer cover (e.g., 22) may comprise a laminate including an elastic nonwoven and a plastic film, for example, polyethylene film. In some embodiments, the outer cover (e.g., 22) may comprise a laminate including an elastic film and a non-elastic nonwoven. Further, the outer cover (e.g., 22) may comprise a laminate including printed elastics. Still further, the outer cover (e.g., 22) may comprise a laminate including an elastic in the form of a scrim-like structure or a crosshatch pattern that is joined between two layers of a nonwoven or between a nonwoven and a breathable Elle (e.g., polyethylene film), etc.

The elastomeric film examples provided above can be laminated to at least one layer of non-elastomeric or extensible nonwoven using spiral glue. Additionally, this laminate can be incrementally stretched in a machine direction and then in a cross machine direction thereby forming a biaxially stretchable elastic laminate (i.e., an elastic laminate that is extensible in the orthogonal in-planar directions simultaneously, or sequentially). A suitable example of a nonwoven which can be utilized in the outer cover (e.g., 22) includes deeply activatable poly propylene (DAPP). A suitable DAPP nonwoven is sold under the designation Softspan 200 available from BBA Fiberweb, Brentwood Tenn. In some embodiments the DAPP can be joined to an elastic element, e.g., elastomeric scrim and joined to a polyethylene film. In some embodiments, the DAPP can be joined to an elastic element, e.g., elastomeric scrim and joined to another DAPP nonwoven.

Outer cover (e.g., 22) laminates, such as those described above, where the elastomeric component is combined with another web in a relaxed, unstretched state, are referred to in the art as "zero-strain laminates". While in some embodiments, the zero-strain laminate may be inherently stretchable in a virgin state, the stretch properties of these materials are usually released or improved by mechanical activation, or incremental stretching, such as ring rolling or SELFing. Alternatively, pre-stretched laminate materials may also be employed as outer cover (e.g., 22) materials in the present invention. Pre-stretched elastomeric outer covers (e.g., 22) are formed by applying an elastomeric material, e.g., strands or films, to a substrate while the elastomeric material is in a prestrained state, and subsequently allowing the laminate to relax and contract. Pre-stretched stretchable outer cover (e.g., 22) materials may be formed by applying pre-tensioned elastomeric elements in at least two different directions aligned with the longitudinal and lateral axes of the article. In certain embodiments, outer covers (e.g., 22) of the present invention may include both zero-strain and pre-stretched elastomers. For example, a pre-tensioned elastomeric element may be affixed to a zero-strain elastomeric laminate either parallel to the zero strain laminate's primary direction of stretch or at an angle thereto.

In some embodiments, the outer cover (e.g., 22) may comprise an elastomeric layer which includes an elastomeric adhesive, e.g., a hot melt pressure sensitive adhesive. In these embodiments, additional adhesive may not be needed to bond the layers of the laminate together. However, if the elastomeric material does not have good adhesive properties, additional adhesive may be utilized.

In some embodiments, the outer cover (e.g., 22) may have a low force at a specific elongation as measured by the. Hysteresis Test (50% Maximum Strain). Since the outer cover (e.g., 22) can have different stretch properties in different directions, stretch properties in the Hysteresis Test are measured in the longitudinal direction (machine direction), lateral direction (cross machine direction) and in a direction that is parallel to the length direction of the anchoring band (previously mentioned at pages 16 and 27). In some embodiments, at least a portion of the outer cover (e.g., 22) may have a first cycle force less than about 20 gm/cm at 15% strain, a first cycle force less than about 15 gm/cm at 15% strain, or a first cycle force less than about 10 gm/cm at 15% strain.

Additionally, in some embodiments, the outer cover (e.g., 22) may also have a percentage set (as measured by the Hysteresis Test) which is less than about 40%. In some embodiments, the outer cover (e.g., 22) may have a percentage set which is less than about 30% or in some embodiments, less than about 15%.

In some embodiments, the outer cover (e.g., 22) may be sufficiently breathable. For example, in some embodiments, the outer cover (e.g., 22) can be constructed to be permeable to at least water vapor and can have a moisture vapor transmission rate (MVTR) of at least about 1000 $g/m^2/24$ hr., at least about 1500 $g/m^2/24$ hr., at least about 2000 $g/m^2/24$ hr., or at least about 3000 $g/m^2/24$ hr. In other embodiments, the outer cover (e.g., 22) may have an MVTR of at least about 7000 $g/m^2/24$ hr. In some embodiments, the outer cover (e.g., 22) may have a MVTR of from about 1000 to about 8000 g/m²/24 hr. or any individual number within the range. Some breathable backsheet materials are described in greater detail in PCT App. No. WO 95/16746; and U.S. Pat. Nos. 5,938,648, 5,865,823 and 5,571,096. Other suitable exemplary materials and a suitable test method for measuring the MVTR are described in U.S. Pat. No. 6,448,467.

Additionally, in some embodiments, the outer cover (e.g., 22) may comprise underwear-like texture/aesthetics. One aspect of underwear like aesthetics is gloss (as measured according to ASTM D2457-97) to give a pleasing matte look (not plastic like). A gloss value of 7 gloss units or less has been found desirable. Embossing and/or matte finishing improves the outer cover's 22 gloss.

The outer cover (e.g., 22), in some embodiments, may have sufficient opacity such that exudates discharged into a core assembly cannot be readily perceived from a vantage point external to the absorbent article (e.g., 20). Also, the outer cover (e.g., 22) may have sufficient opacity to prevent the skin from being seen in the non-core areas of the absorbent article (e.g., 20). In order to increase the opacity of stretchable outer cover (e.g., 22) elastic nonwovens, in some embodiments, at least one meltblown may be incorporated into the spunbond web. The meltblown layer may consist of nano-fibers. The meltblown layer may have a basis weight of between about 1 gsm and about 20 gsm or any individual number within the range. In some embodiments the meltblown layer may have a basis weight of between about 4 gsm and about 15 gsm and may comprise various combinations of elastomeric and plastic polymeric resins. Higher elastomeric content may be preferred when higher depths of activation (incremental stretching) are required and/or when lower permanent set values in the outer cover (e.g., 22) are desired. Elastomeric and plastic polyolefin combinations may utilized in some embodiments to optimize the cost/performance balance. In some embodiments, the elastomeric component may comprise a very low crystallinity polypropylene grade such as those commercialized by ExxonMobil under the tradename Vistamaxx. Additionally, the elastic nonwoven structure may also include another spunbond layer that does not provide significant elastic recovery, yet possesses sufficient extensibility to survive the activation process. Some suitable examples of such extensible spunbond nonwoven layers are disclosed in PCT App. Nos. WO 2005/073308 and WO 2005/073309.

Other exemplary breathable materials can include materials such as woven webs, nonwoven webs, polymeric films such as thermoplastic films of polyethylene or polypropylene, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE, Suitable breathable composite materials comprising polymer blends are available from Clopay Corporation, Cincinnati, Ohio under the name HYTREL blend P18-3097. An exemplary, suitable outer cover (e.g., 22) is disclosed in U.S. Pat. No. 6,107,537.

The stretchable outer cover (e.g., 22) can also be made by elastomer printing, spraying, slot coating, meltblown or film lamination. Printing includes gravure, flexogaphic, letterpress, screen, digital, or the like. Some suitable examples of elastomer printing are described in U.S. Patent App, Pub, Nos. 2003/0088220A1 (Abandoned); 2003/0088228A1; (U.S. Pat. No. 7,056,411) 2003/0091807A1; 2004/0193133A1 (U.S. Pat. No. 7,862,549); 2004/0222553A1 (Abandoned); 2005/0214461A1; 2003/0084996A1 (U.S. Pat. No. 6,942,894); 2003/0084996A1 (U.S. Pat. No. 6,942,894); 2003/0087059A1 (Abandoned); 2003/0087098A1 (U.S. Pat. No. 6,875,710); and U.S. Pat. Nos. 6,875,710 and 6,942,894.

Spraying includes standard techniques for hot melt adhesive spraying, e.g., spiral, zig-zag pattern, ITW's Omega pattern, meltblown, etc. An elastomeric film can be bonded to a nonwoven by extrusion or adhesive lamination.

In accordance with certain aspects of the invention, various materials can be used to provide a stretchable outer cover (e.g., 22). When constructing the stretchable outer cover (e.g., 22), various desirable features include the following:

Mechanical properties (as expressed in terms as measured in a Hysteresis test) during multiple medium-strain stretch-recovery cycles, as well as the ability to survive high-strain-rate medium depth of engagement mechanical activation in both machine direction and cross direction without pinhole);

Durability (low Fuzz, high ultimate strength);

Visuals (white color, high opacity, cotton-ribbon-like texture, printable, gloss);

Liquid barrier properties in some embodiments (absence of pinholes or any other signs that could signal the possibility of outer cover (e.g., 22) leakage); and Low cost.

Variations in specific targets may be found depending upon whether the design is for a pant or a taped absorbent article (e.g., 20). For instance, as is described in more detail below, one embodiment of a taped absorbent article (e.g., 20) design has an integrated anchoring system built into the stretchable outer cover (e.g., 22) which is created by differential activation (an area of the stretchable outer cover (e.g., 22) is intentionally left un-activated). Therefore, the development of the outer cover (e.g., 22) material takes into account performance targets for both pre- and post-activation states. The pant design may have more stringent upper limits for the CD stretch load of the stretchable outer cover (e.g., 22) in order to maintain easy absorbent article (e.g., 20) application.

The stretchable outer cover (e.g., 22) may have mechanical and/or elastic properties as described herein, as well as the ability to survive high-strain-rate mechanical activation (i.e., incremental stretching) in both the longitudinal and lateral directions without pinhole formation. Laminates that exhibit reduced pinholes from activation are described in U.S. patent applications Ser. No. 11/361,918 (U.S. Pub. No. US 2007-0202767-Abandoned). Additionally, the outer covers (e.g., 22) of the present invention may have a low tendency to fuzz, have high opacity, and may be printable via printing processes common to the art.

In some embodiments of the present invention, the stretchable outer cover (e.g., 22) comprises only an elastic nonwoven. In these embodiments the total basis weight of the outer cover (e.g., 22) may be less than about 50 gsm, less than about 40 gsm, or less than about 35 gsm. The outer cover (e.g., 22) material may comprise a spunbond fabric and be produced under conditions that promote optimal bond strength in order to provide sufficient strength and durability to the outer cover (e.g., 22). Elastic nonwoven outer covers 22 may include at least one elastomeric material in a sufficient amount to provide a minimal desirable amount of recovery. Examples of suitable spunbond nonwovens are described in U.S. Pat. Nos. 5,470,639 and 5,997,989.

In some embodiments of the present invention, the elastic nonwoven comprises elastic/plastic bicomponent fibers, examples of which are described in U.S. Pat. No. 6,225,243 and PCT App. No. WO 2006/017674, to provide the outer cover (e.g., 22) material with better hand/feel properties and improved spinnability. The outer cover (e.g., 22) material may also comprise webs, as disclosed in PCT App. No. WO 2005/065680, formed of mixed elastic fibers (e.g., thermoplastic polyurethane elastomer) and plastic (e.g., polyolefins such as polypropylene) fibers, said nonwovens having good elastic recovery and tactile properties after being subjected to mechanical activation, such as Vistamax™ available from Exxon. Another suitable elastic component is very low crystallinity elastomeric polypropylene. Other suitable examples of spunbond elastic nonwovens are disclosed in PCT App. Nos. WO 2005/052052 and WO 2005/097031, In embodiments where the elastic nonwoven outer cover (e.g., 22) comprises mixtures or composites of both elastic and plastic materials, the ratio of the elastic to plastic components can be tailored to provide a desirable balance of both stretch/recovery characteristics and strength/toughness requirements. High toughness is desirable to maximize the ability of the web to survive mechanical activation in both the longitudinal and lateral directions.

Other exemplary materials suitable for the outer cover (e.g., 22) are disclosed in U.S. Pat. Nos. 6,896,843, 6,2.25, 243, 5,997,989, 5,952,252, 5,695,849, 5,470,639, 5,405,682, 6,811,871, 6,103,647, 5,635,290 and 5,540,976; U.S. Pat. App. Pub. Nos. 2004/0132374 (Abandoned), 2004/0110442 (Abandoned); and 2003/0162458 (U.S. Pat. No. 7,462,573); and PCT App. Nos. WO 2005/052052; WO 2004/065680 and WO 2006/017674.

In some embodiments of the present invention, the stretchable outer cover (e.g., 22) may comprise a laminate of elastic nonwovens, such as those described above, and an extensible film. In this embodiment, a thin extensible polyolefin film layer is laminated onto the elastic nonwoven described above. Although higher basis weights are contemplated in certain embodiments, the basis weight of the film may be no more than about 22 gsm, no more than about 20 gsm, and no more than about 18 gsm in order to minimize the cost of the laminate. The film may be combined with the elastomeric nonwoven via adhesive lamination, extrusion lamination, or any other suitable means of combining webs as known in the art. The film may be extensible in both longitudinal and lateral directions and able to survive a mechanical activation (i.e., incremental stretching) process without pinhole formation over a wide range of activation strains. The film may be breathable, as discussed previously, whether the breathability originates from activation-induced micro-porosity or virtually invisible pinholes. The film may be either extensible, i.e., plastic, or it may be plastoelastic and exhibit partial recovery, hence participating in the elastic recovery process. Examples of "plastic" films include films comprising standard filled polyethylene resins, e.g., those disclosed in PCT App. No. WO 2006/017518. Examples of the use of plastoelastic film formulations are disclosed in PCT App. No. WO 2005/097031. The presence of the film laminated onto the stretch NW contributes to the creation of highly desirable visuals, such as high opacity and high texture without the need for incorporating the type of melt-blown layer described above. Alternatively, the film may comprise high-performance elastomers such as Kraton-based elastomers. Further examples of elastic nonwoven/ extensible film laminates suitable for the present invention are disclosed in PCT App. No. WO 2005/017518; U.S. Pub. No. 2005/0124952 (Abandoned); and U.S. Pat. Nos. 6,811, 865, 6,623,837 and 6,096,668.

In some embodiments, the film can be the component that exhibits at least partial recovery upon stretching. The nonwoven may be an extensible spunbond or a necked/gathered spunbond. The basis weight of the film may be no more than about 22 gsm, no more than about 20 gsm, or no more than about 18 gsm in order to minimize the cost of the laminate, as well as minimize the force required to stretch the biaxially stretchable outer cover (BSOC) up to 50% strain, The film may be combined with the nonwoven either via adhesive lamination or via extrusion lamination. An example of a tilled elastic polyethylene blend film is disclosed in U.S. Pat. No. 6,909,028, Elastomeric polypropylene-based compositions are disclosed in PCT App, Nos, WO 2005/052052 and WO 2005/097031. Blends of elastomeric polypropylenes with either styrenic block-copolymers, semicrystalline polyolefins or sub-micron inorganic particles can be used to enhance the stress-strain and hysteresis properties of the laminate. For example, decreasing the force required to extend the BSOC and improving elastic recovery is achievable by adding styrenic block copolymers into a Vistamaxx polymer. Micro-porous breathable elastic films based on calcium carbonate-filled elastomeric polypropylene-based compositions are also contemplated. The film may additionally increase the opacity of the BSOC and potentially eliminate or reduce the need for the presence of a meltblown layer in the nonwoven.

Exemplary stretchable outer cover (e.g., 22) materials related to these embodiments are disclosed in U.S. Pat. Nos. 6,909,028; 6,680,265; 6,680,265; 6,015,764; 5,947,94; 6,627,564; 6,479,154; 6,465,073; 6,313,372; 6,001460; and 6,849,324; and PCT App. Nos. WO 2004/060669 and WO 2004/060652.

In some embodiments of the present invention, an elastomer may be printed onto a nonwoven, film, or laminate, including those described above, to form a BSOC. The elastomer may be printed as a film or in a pattern. If printed as a pattern, the pattern may be relatively homogeneous over the area of the outer cover (e.g., 22), e.g., in a net-like or dot pattern, or may comprise regions of relatively higher or lower basis weight where the elastomeric component has been applied onto at least one region of an extensible fibrous substrate to provide stretch properties to a targeted region of the substrate after selective incremental stretching). The elastomer may be transferred onto the fibrous substrate through a process such as gravure printing which provides a great deal of flexibility relative to the amount of elastomer deposited, as well as the type of patterns that can be achieved. Details on these embodiments, and further examples of suitable materials and patterns, are disclosed in U.S. Pub. No, 2005/0214461 and PCT App. Nos. WO 2005/097358 and WO 2005/097512. Polyolefin blends and polyolefins/styrenic block copolymers, such as those disclosed above, may be tailored to possess the desired rheological characteristics for adequate deposition via gravure printing. Other exemplary materials and processes are disclosed in U.S. Pub. No. 2005/0106980 (Abandoned) and U.S. Pat. Nos. 6,579,274, 6,503,236 and 6,264,641.

Regardless of the composition of the stretchable outer cover (e.g., 22), it can be mechanically activated in both the longitudinal and lateral directions via any of the processes described herein.

Said activation may be used to increase the strain range over which the web exhibits stretch/recovery properties, impart the desirable tactile/aesthetic properties to the material (e.g., a cotton-like texture), and in some embodiments, may be used to create the higher modulus components of the anchoring system, including linkages or anchoring bands. Mechanical activation may be achieved via ring-rolling, SELFing, and other means of incrementally stretching webs as known in the art. In some embodiments it may be desirable to over-bond the outer cover (e.g., 22) to further increase the mechanical strength of the outer cover (e.g., 22).

As described in greater detail herein, the outer covers (e.g., 22) of the present invention may additionally comprise graphics 10 printed on the outside or inside surface of one of the outer cover or waist/leg band components or printed on an underlying component of the absorbent article (e.g., 20). The graphics 10 may be decorative, educational, entertaining, or instructional. The graphics 10 may be most clear or legible when the printed substrate is in a relaxed condition, while others are most clear/legible when the printed substrate is in an extended condition. In certain embodiments, the graphics 10 comprise active graphics, i.e., graphics which change based on environmental conditions such as elapsed time, humidity, temperature, wetness, etc. Active graphics may be topically related to each other so as to portray and event or action (e.g., a fish appears or disappears from a character's fishing line).

Tests/Methods

Hysteresis Test for Elastomers/Elastomeric Composites

A commercial tensile tester from Instron Engineering Corp., Canton, Mass. or SINTECH-MTS Systems Corporation, Eden Prairie, Minn. (or a comparable tensile tester) is used for this test. The instrument is interfaced with a computer for controlling the test speed and other test parameters, and for collecting, calculating and reporting the data. The hysteresis is measured under typical laboratory conditions (i.e., room temperature of about 20° C. and relative humidity of about 50%).

A sample of material is made by cutting the material to be tested 1" wide by 3" long. The procedure for determining hysteresis involves the following steps:
1. Choose the appropriate jaws and load cell for the test; the jaws are wide enough to fit the sample, typically 1" wide jaws are used; the load cell is chosen so that the tensile response from the sample tested will be between 25% and 75% of the capacity of the load cells or the load range used, typically a 50 lb load cell is used;
2. Calibrate the tester according to the manufacturer's instructions;
3. Set the gauge length at 25 mm;
4. Place the sample in the flat surface of the jaws such that the longitudinal axis of the sample is substantially parallel to the gauge length direction;
5. The hysteresis test involves the following steps:
    a) pull the sample to 50% strain at a cross head speed of 10 in./min (254 mm/min)—first cycle loading
    b) hold at that strain for 30 seconds and return to 0% strain at the same crosshead speed—first cycle unloading
    c) allow the sample to remain at this strain for 1 minute; and
    d) pull to 50% strain at a constant rate of 10"/min (254 mm/min)—second cycle load
    e) hold at that strain for 30 seconds and return to 0% strain at the same crosshead speed—second cycle unloading
From the data collected in step 5, the following two measurements are used:
    a) first cycle force at 15% strain
    b) % set, which is defined as the strain at 0.05N in the second loading cycle. The 0.05N force is deemed sufficient to remove the slack but low enough to impart, at most, insubstantial stretch to the sample.
6. Record data for first cycle load at 15% strain
7. Record data for % set.

Method for Generating Seam Noticeability Test Images

Disposable absorbent articles to be tested for seam noticeability are converted into digital stimuli (test images) by the following process. If the disposable absorbent article is manufactured in a closed form (e.g., a pant-type diaper), it is re-opened such that a seam resulting from a right front side zone (i.e., looking at the front garment-facing surface of the article, as it is correctly worn) connected to a central zone (i.e., the seam of interest) and surrounding area remain intact and undisrupted. The article is to he opened by cutting or opening a seam that connects the front side panel to a back side panel. The closed form disposable absorbent article is opened on both sides in the same manner, such that the article can be laid substantially flat. The article is taped with double sided clear tape (such as 3M ½ inch double sided tape) to a rectangular sheet of ¼ inch thick black polyacrylate (such as Lexan) larger in both lateral and longitudinal dimensions than the article's largest lateral or longitudinal dimension. The article is centered on the polyacrylate sheet, and a front waist of the article, including front portions of side stretch regions, is aligned with a tape line parallel to a waist edge. The article is pressed onto the tape line such that any pre-contraction in a waistband is removed, and the side stretch regions are unstretched, but lie flat on the polyacrylate sheet. The article is then pulled along a longitudinal axis until any pre-contraction is removed. A back waist of the article, including back portions of the side stretch regions, is aligned and pressed on to a second tape line parallel to a back waist edge. The article is taped with a body-facing surface against the polyacrylate sheet so that a completed assembly presents a substantially unwrinkled and flat garment-facing surface on a black background. Pantone uncoated solid chips 420U, 421U, 422U, 423U, 424U, 425U, 426U, and Pantone coated process chips Yellow C, Magenta C, Cyan C, and Black C are affixed to the polyacrylate sheet with tape such that the Pantone chips nor the tape touch the article, and the tape does not cover color regions of the Pantone chips. The polyacrylate sheet is then scanned into Adobe Photoshop CS3 (or equivalent image editing software) at 200 dots per inch (dpi) using an HP ScanJet 3500c or equivalent scanner of sufficient size to fit the entire polyacrylate sheet on a scanning surface.

The scanned image is converted from a raw 8 bit RG B image into an 8 bit CMYK image using Photoshop's built in converter. A new layer is created in the scanned image, and rectangles are drawn and filled with each of the scanned Pantone colors (420U, 421U, 422U, 424U, 425U, 426U, Yellow C, Magenta C, Cyan C, and Black C) from Photoshop's color library. The color curves of the scanned layer are adjusted until a 101 pixel by 101 pixel color sample taken with the color sampler tool in the center of the scanned Pantone chip exactly matches the color value from the Photoshop generated color swatch. The swatch layer is then deleted.

The image is then rotated so that the waist edge nearest the seam of interest is at a top of a Photoshop canvas and is aligned parallel to a horizontal axis of the canvas. A rectangular area is selected approximately ½ a lateral width of the article and ¼ a longitudinal length of the article and containing the entire seam of interest substantially centered in the area. This area is copied into a new 200 dpi CMYK image with a 50% grey background and same dimensions as the selected area. The polyacrylate sheet and any other part of the new image which is not part of the article is selected and deleted, leaving the selected area of the article on a 50% grey background. The resulting image is saved as a Photoshop PSD file using the embedded US. Web Coated (SWOP v2).

The Photoshop files resulting from this process are sent to a third party digital proof printer such as Precision Rubber Plate Company, Indianapolis, Ind.). The digital proof printer opens the CMYK Photoshop files using the embedded US. Web Coated (SWOP v2). The files are saved as Photoshop EPS tiles, keeping the embedded profile intact. The EPS files are placed into an Adobe Illustrator CS2 (or equivalent software) layout file measuring 24 inches wide by 20 inches high. Up to six EPS files are placed into each layout file, centering each EPS file in its own 8 inch by 10 inch rectangle such that no rectangles overlap. The EPS files are then scaled up or down without changing the aspect ratio such that either the horizontal or vertical edges are ¼ inch from the 8 inch by 10 inch rectangle, and no part of the image is closer than ¼ inch to an inner edge of the rectangle. Black identifying numbers are added to the bottom of each EPS file inside the file's rectangle, but outside of the image area. The resulting layout files are printed as PostScript Level 3 files using a Dupont Digital Proofer (or equivalent) as the PostScript Printer Description (PPD). Color Management in Illustrator is set as follows: Document Profile is set to US. Web Coated (SWOP) v2, Color Handling is set to Let Illustrator determine colors, Printer Profile is set to U.S. Web Coated (SWOP) v2, and Rendering Intent is set to Relative Colormetric (equivalent methods for creating color-matched proof prints from digital images are acceptable). PostScript files are ripped using Dupont Digital Proofer software with Precision Rubber Plate Company's matchprint$_{091505}$mdn setting for color matching (or equivalent(s)). Proofs are printed on Cromalin proofer using Dupont digital Cromalin Matte Paper (or equivalent(s)).

Control images are created from basic patterns in Adobe illustrator CS2 (or equivalent software). Referring to FIGS. 22A-D, four classes of patterns are used for this test: horizontal stripes 26000, zig-zags 26001, repeating clusters of circles 26002, and repeating bears 26003. All patterns are created on a background CMYK color of 67:22:0:0 and with a foreground color of Pantone 2736 C covering a CMYK document of 300 mm×600 mm. Four other pattern variables are included: scale, vertical spacing, horizontal spacing, and foreground/background contrast.

Scale is defined as the size of a foreground repeating unit 26008. For horizontal stripes 26000, scale is twice the vertical width a of a stripe 26004. For zig-zags 26001, scale is the vertical distance h from a downward-pointing peak 26005 of the pattern to an upward-pointing peak 26006 of the pattern, and also is twice the vertical width of a line segment. For clusters of circles 26002 and bears 260003 scale is an edge length of the smallest size square 26007 than can be circumscribed around the repeating unit 26008.

Vertical spacing is defined as the distance r of background space between the lowest edge of one horizontal pattern row 26004 and the highest edge of the next lower horizontal pattern row 26004.

Horizontal spacing is defined as the distance of background space between the horizontal neighbors of the pattern. This variable is undefined for stripes 26006. For zig-zags 26001, this variable is the distance d of horizontal span between an upward-pointing peak of the pattern and the neighboring downward-pointing peak of the pattern. For circle clusters 26002 and bears 26003, horizontal spacing is the distance e between the rightmost edge of the repeating unit 26008 and the leftmost edge of the right-hand neighbor. For circle clusters 26002 and bears 26003, horizontal rows 26004 of repeating units 26008 which are vertical neighbors are horizontally offset from each other by one half of the horizontal spacing.

Contrast is defined as the opacity of the foreground elements 26009 of the pattern (e.g., 26000, 26001, 26002, and 26003), with lower opacities resulting in lower contrast between the foreground elements 26009 and the background 26010 of the pattern.

To convert the patterns into the final files, they are opened in Adobe Photoshop CS3 and rendered at 200 dpi resolution. An 8 inch by 10 inch sample of a 27 gsm highly extensible carded (HEC) nonwoven from BBA (Material #2003-1711-02) is placed on an 8 inch by 14 inch sheet of black polyacrylate alongside Pantone uncoated solid chips 420U, 421U, 422U, 423U, 424U, 425U, and 426U and Pantone coated process chips Yellow C, Magenta C, Cyan C, and Black C. The assembly is scanned into Photoshop on an HP ScanJet 3500 c (or equivalent) at 200 dpi resolution. The scanned image is converted from a raw 8 hit RGB image into an 8 hit CMYK image using Photoshop's built in converter. A new layer is created in the scanned image, and rectangles are drawn and filled with each of the scanned Pantone colors (420U, 421U, 422U, 424U, 425U, 426U, Yellow C, Magenta C, Cyan C, and Black C) from Photoshop's color library. The color curves of the scanned layer are adjusted until a 101 pixel by 101 pixel color sample taken with the color sampler tool in the center of the scanned Pantone chip exactly matches the color value from the Photoshop generated color swatch.

An article outline from a size 4 unseamed disposable pant is used to draw a 2D master die shape to scale in Adobe Illustrator CS2. The upper right hand corner of the master die shape Illustrator page corresponds to the front waist where the side panel is on the right hand side of the outer cover. The master die shape Illustrator page is saved as an Illustrator AI file, is imported into Adobe Photoshop CS3 at 200 dpi, and is placed in its own layer of the scanned image. The die shape is filled with the background color from the pattern file (CMYK 68:22;0:0). The scanned image layer is then placed over the die shape layer and combined with a standard multiply at 25%. The layers are oriented such that the machine direction of the nonwoven fibers is perpendicular to a waist edge of the master die shape, the Pantone chips are outside the die lines, and an upper right hand corner of the die shape layer and an upper right hand corner of the scanned nonwoven layer are aligned (coincident). The scanned layer is then duplicated and combined with a standard screen at 100%, The seam between the right front side zone and the central zone is defined by duplicating the screen layer and deleting all of it except a 20 pixel wide stripe aligned with the master die line representing the seam between the right front side zone and the central zone. This area represents the seam of interest.

The right front side zone further comprises an additional layer comprised of 5 rectangular solid black stripes running perpendicular (longitudinally) to the front waist edge, measuring 26 pixels wide, and trimmed to exactly span the longitudinal length of the right front side zone. The stripes are evenly spaced in a direction parallel (laterally) to the front waist edge to exactly span the lateral width of the right front side zone. The layer is filtered with a Smart Motion Blur (angle 0 degrees, distance 12 pixels) and combined with a standard multiply at 20%.

The pattern image is then adjusted to account for two seam variables: vertical offset of the side seam and horizontal overlap of the seam. The master die shape is overlayed on the pattern image, and the central zone is selected in the master die layer. The die layer is then turned off, and the selected area in the pattern layer is copied into a central zone pattern layer. The original pattern layer is then shifted vertically and horizontally to simulate offset and overlap. The master die layer is turned back on, and the right front side zone is selected. The master die layer is turned back off, and the selected area in the pattern layer is copied into a right front side zone pattern layer.

The resulting central zone pattern layer and right front side zone pattern layer are copied into a new CMYK image with a 50% grey background. The size of the new image is defined as a rectangular area approximately ½ the width of the article in a direction parallel (laterally) to the front waist edge and ¼ the length of the article running perpendicular (longitudinally) to the front waist edge. The upper right hand corner of the central zone pattern layer and the upper right hand corner of the right front side zone pattern layer are aligned (coincident) with the upper right hand corner of the new image. The scanned image, which is also cropped to the master die shape as described above, is then copied into the image with the 50% grey background and placed over the pattern layers. The scanned image layer's upper right hand corner is aligned with the upper right hand corner of the 50% grey background image. The resulting control image Photoshop file is sent to a digital proofer for printing as above.

The variable combinations used to create the control images are listed in Table 1 below.

While this method is drawn to the right front side zone connected to a central zone as the seam of interest, one of ordinary skill in the art may make adjustments to measure and evaluate other seams of interest. For example, this method is readily able, with only minor adjustments, to measure a seam formed by the front side panel in the right side zone and the back side panel in the right side zone.

Method for Generating a Seam Noticeability Rating

Seam noticeability grading is performed by representative or perspective consumers of the disposable absorbent article of interest in a standardized grading room. Consumers are selected based on being the mother and primary care-giver of a child currently wearing a disposable absorbent article of similar form to the article of interest (e.g., pant-type diaper, tape-type diaper, etc.). The wearer of the article is within the appropriate target age range for the article (e.g., from 18 to 36 months of age for a typical pant diaper wearer in the US) and the consumer possesses normal visual acuity and perception as can be determined by the consumer possessing a valid and unrestricted US drivers license or by receiving a passing grade on the visual and perceptual portions of the US drivers license exam. Consumers requiring prescription corrective lenses to pass the exam will be admitted provided that they wear said lenses at the time of the seam noticeability grading.

Figure 21:
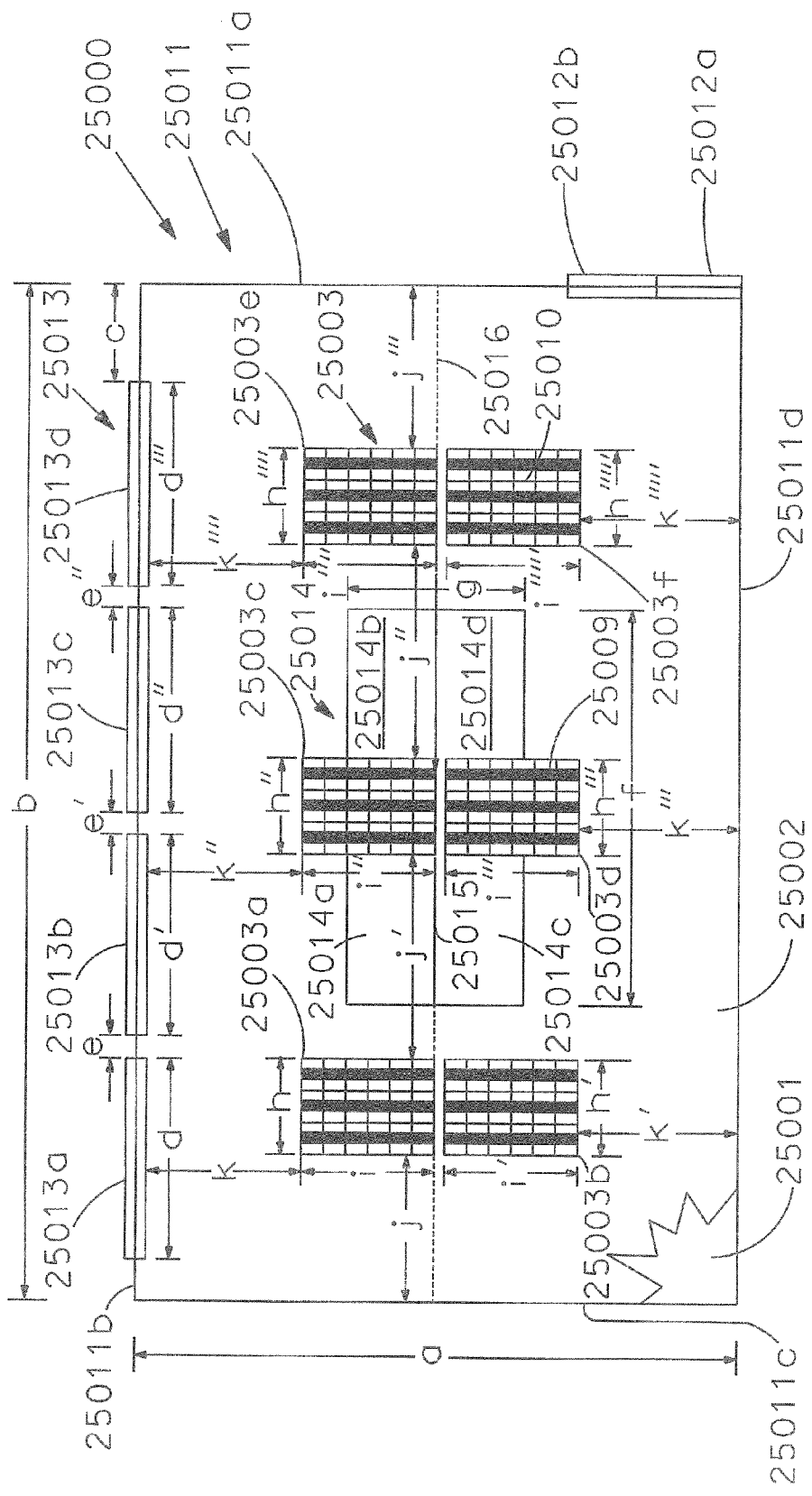
FIG. 21 is a top view representation of a standardized grading room for use in the Method for Generating a Seam Noticeability Rating.
Figure 22A:
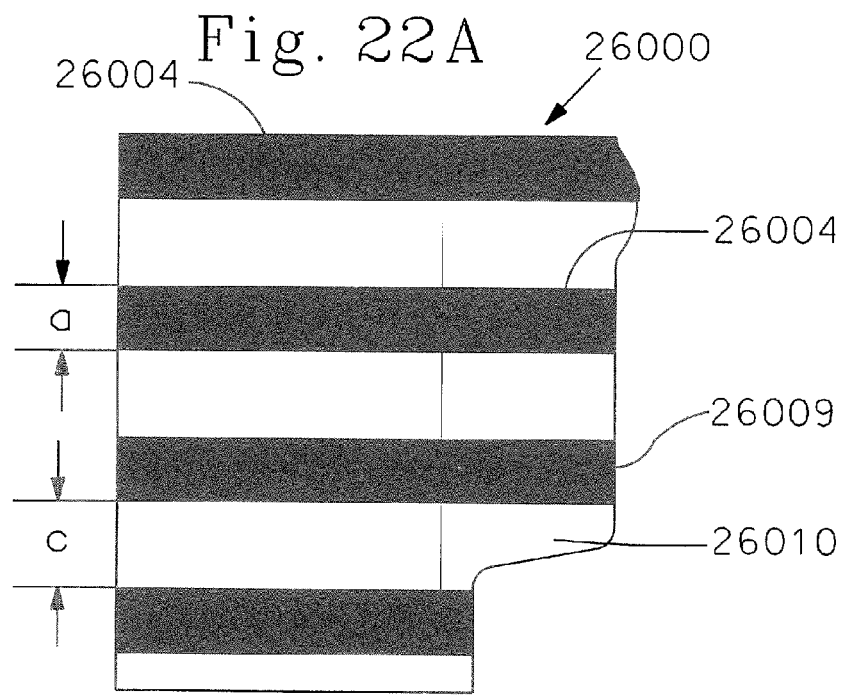
FIGS. 22A-D are side view representations of the four classes of patterns for use in the Method for Generating Seam Noticeability Test Images.
Figure 22B:
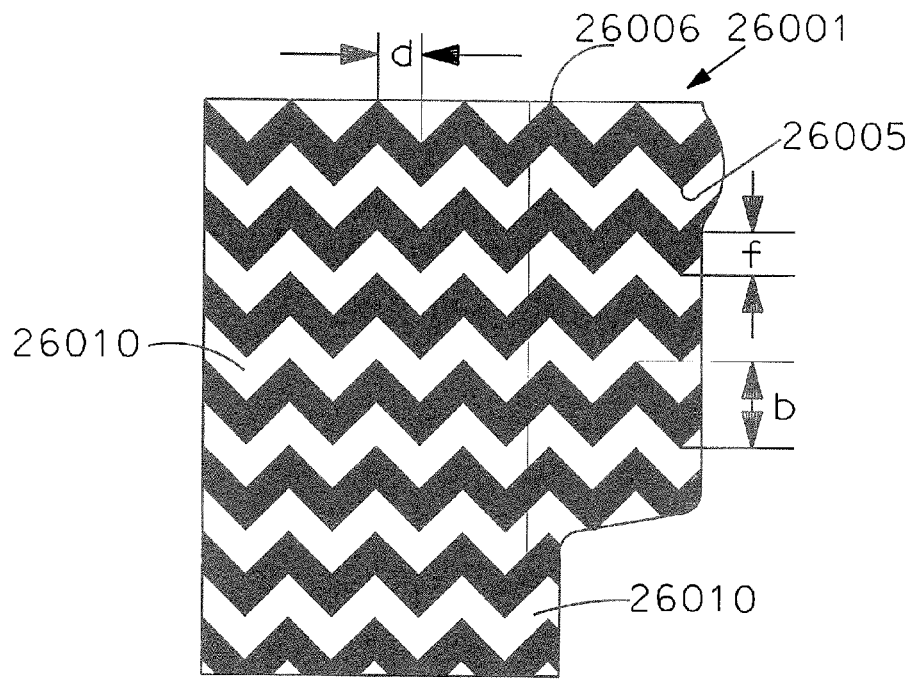
Figure 22C:
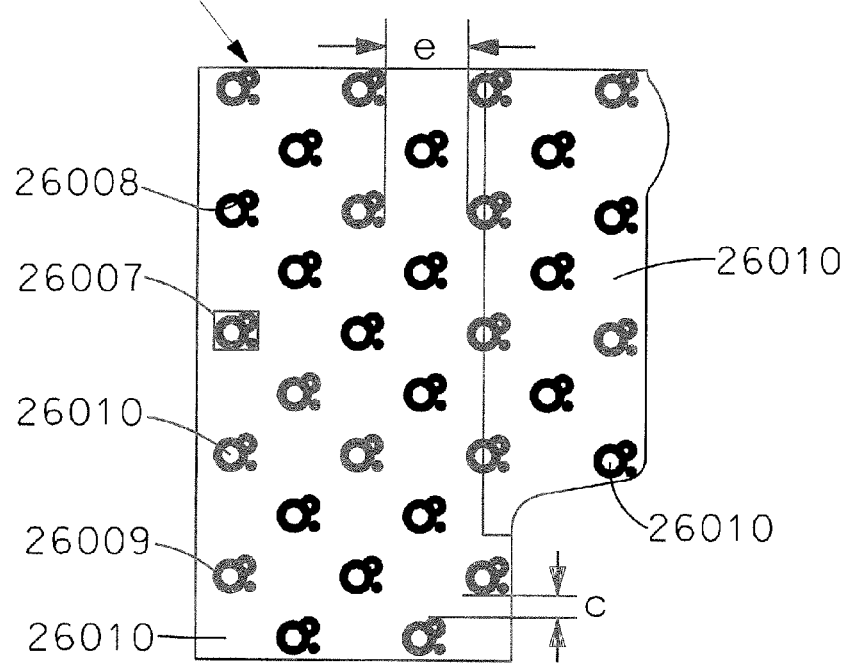
Figure 22D:
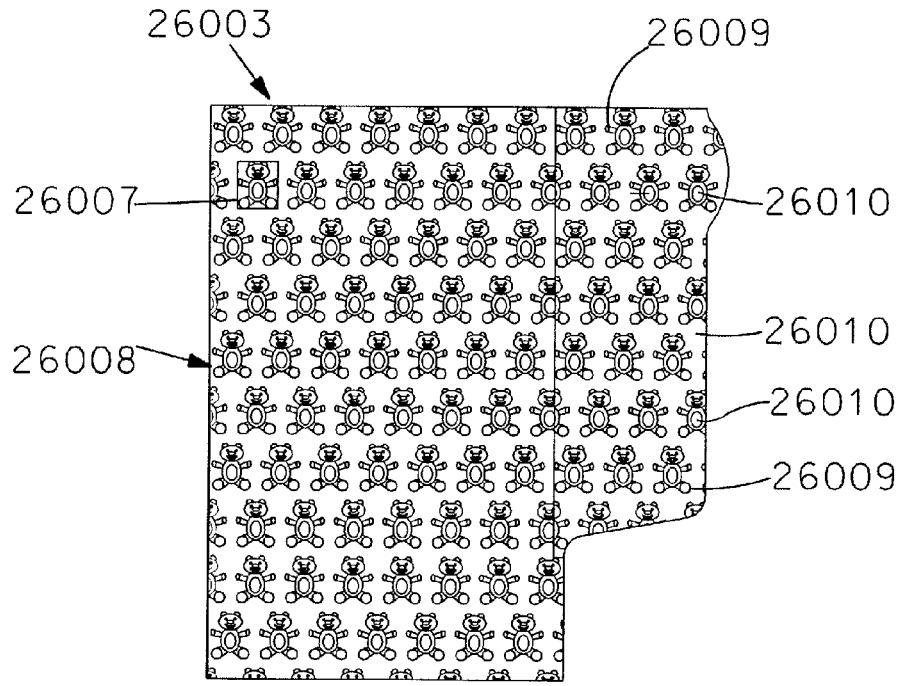
Figure 23:
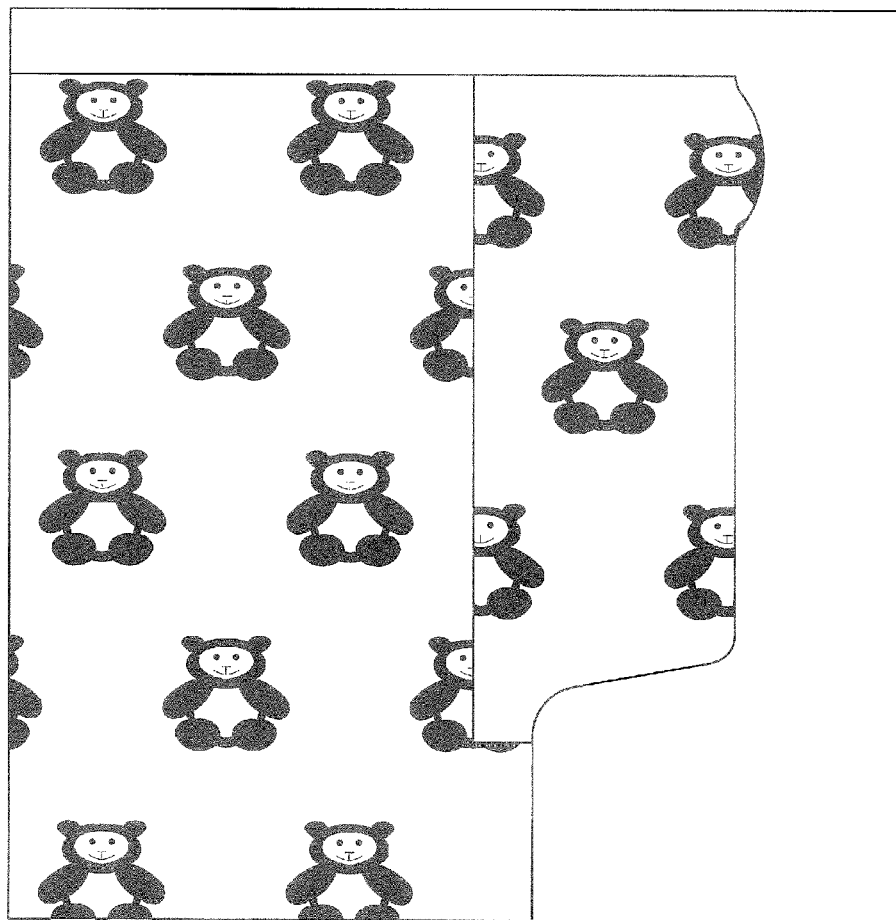
FIGS. 23-26 are representations of images tested according to the Method for Generating a Seam Noticeability Rating.
Figure 24:
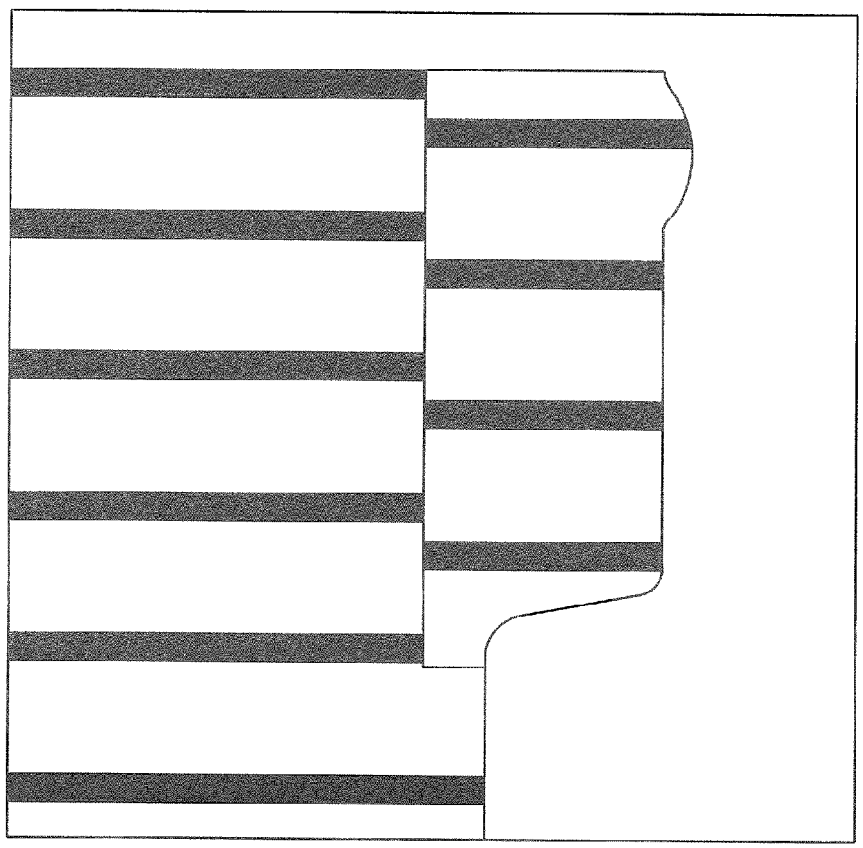
Figure 25:
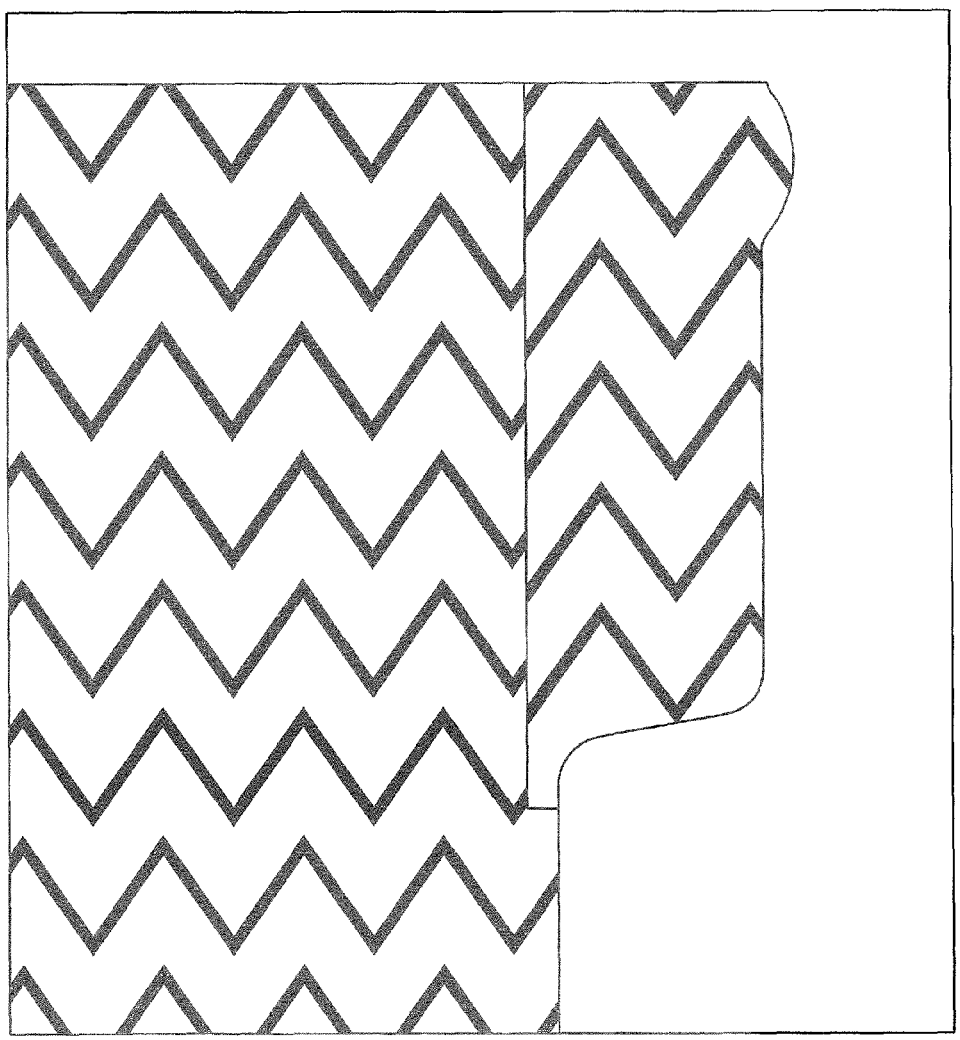
Figure 26:
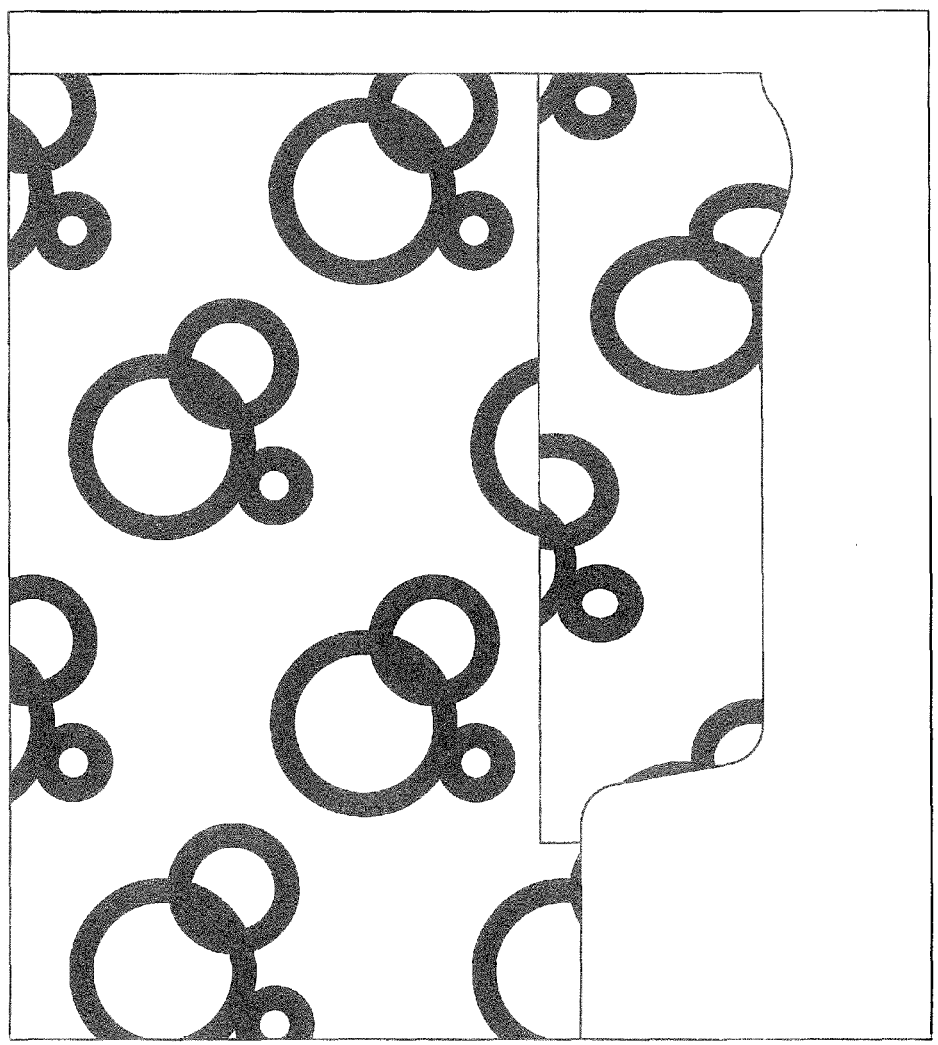

Referring to FIG. 21, the standardized grading room 25000 is rectangular having a width a of 14 feet by length b of 22 feet, the ceiling 25001 is a height of 8 feet above the

TABLE 1

| Control Image # | Pattern | Scale | Vertical Spacing | Horizontal Spacing | Vertical Offset | Horizontal Offset | Contrast |
|---|---|---|---|---|---|---|---|
| 1 | bears | 10 | 10 | 10 | 16 | 7 | 60 |
| 2 | bears | 20 | 10 | 20 | 7 | 15 | 100 |
| 3 | bears | 10 | 2 | 2 | 0 | 0 | 60 |
| 4 | bears | 30 | 2 | 10 | 0 | 0 | 100 |
| 5 | bears | 30 | 10 | 2 | 7 | 0 | 100 |
| 6 | circles | 10 | 20 | 20 | 0 | 0 | 100 |
| 7 | circles | 20 | 20 | 2 | 7 | 7 | 60 |
| 8 | circles | 10 | 2 | 2 | 15 | 0 | 25 |
| 9 | circles | 30 | 2 | 20 | 15 | 7 | 60 |
| 10 | circles | 30 | 20 | 10 | 0 | 15 | 60 |
| 11 | stripes | 10 | 10 | 2 | 15 | 15 | 100 |
| 12 | stripes | 30 | 2 | 20 | 0 | 7 | 25 |
| 13 | stripes | 10 | 20 | 20 | 7 | 15 | 60 |
| 14 | stripes | 20 | 2 | 20 | 7 | 0 | 25 |
| 15 | stripes | 20 | 10 | 10 | 0 | 7 | 100 |
| 16 | zig-zag | 10 | 2 | 10 | 7 | 0 | 60 |
| 17 | zig-zag | 30 | 10 | 10 | 15 | 0 | 25 |
| 18 | zig-zag | 20 | 20 | 20 | 15 | 15 | 60 |
| 19 | zig-zag | 30 | 2 | 20 | 7 | 15 | 60 |
| 20 | zig-zag | 30 | 10 | 20 | 7 | 7 | 100 |

Each digital proof image from both the control image set and the test image set is cut out along its 8 inch by 10 inch rectangle and placed in an optically clear sheet protector, such as an Avery Heavyweight Diamond Clear Presentation Sheet Protector. Images are randomized before presenting to consumers for grading in the grading room. Randomization is achieved by listing the image identifier for all images including test images and control images in one column in Microsoft Excel, and a random number in the adjacent column (formula "=rand( )"). The two columns are then selected and sorted in ascending order according to the random number. This is repeated a number of times equal to the number of panelists, making sure to recalculate the random number column in between sorts, and the unique randomly ordered image identifier list is recorded for each panelist.

floor 25002, and the room 25000 is lit by six rectangular inset lighting fixtures 25003a-f which measure widths h, h', h", h''', h'''', and h''''' of 2 feet and lengths i, i', i", i''', i'''', and i''''' of 4 feet. Each fixture 25003 has three fluorescent bulbs 25009 (such as Octron 4100K Ecologic Hg 32W fluorescent bulbs, available from Sylvania, Danvers, Mass.). The lighting fixtures 25003 are arranged so that each has a shorter dimension which follows a long axis 25016 of the room 25000. Fixture 25003a is positioned a distance j of 4 feet from wall 25011c and a distance k of 3 feet from wall 25011b. Fixture 25003b is positioned a distance j of 4 feet from wall 25011c and a distance k' of 4 feet from wall 25011d. Fixture 25003c is positioned a distance l of 4 feet from fixture 25003a and a distance k" of 3 feet from wall 25011b. Fixture 25003d is positioned a distance j' of 4 feet from fixture 25003b and a distance k''' of 3 feet from wall 25011*d*. Fixture 25003*e* is positioned a distance j" of 4 feet from fixture 25003*c*, a distance k" of 3 feet from wall 25011*b*, and a distance j" of 4 feet from wall 25011*a*. Fixture 25003*f* is positioned a distance j" of 4 feet from fixture 25003*d*, a distance k'''' of 3 feet from wall 25011*d*, and a distance j''' of 4 feet from wall 25011*a*. Each fixture 25003 is fitted with a four inch deep reflector grid 25010 which divides each fixture 25003 into 18 sections measuring 8 inches by 8 inches as shown in FIG. 21. The walls 25011*a-d* and doors 25012*a-b* are made of a material such that external light does not enter the room 25000 when the doors 25012*a-b* are closed. One wall 25011*b* of the room 25000 is fitted with four one-way mirror panels 25013*a-d* arranged such that the consumer in the grading room 25000 cannot see into the adjacent observation room (not shown). Each of the mirrors 25013 measure widths d, d', d", and d''' of 55 inches wide by 47 inches high (not shown) with the first mirror 25013*a* placed a distance c of 21 inches from the wall 25011*a* and each placed distances e, e', and e" of 3 inches of framing between each mirror panel 25013. A bottom edge (not shown) of the mirror 25013 is 33 inches from the floor 25002. There are four tables having top surfaces 25014*a-d*, each having a table surface length of 60 inches by a width of 30 inches and a height of 30 inches (not shown) from floor 25002, and arranged to form a table surface length f of 120 inch by a width g of 60 inch surface centered in the room with the long axis 25015 of the table surfaces 25014 aligned with the long axis 25016 of the room 25000. The table surfaces 25014 (as well as the legs, etc. (not shown)) are a neutral color, as well as the two chairs (such as "Drive" Work Chairs in neutral upholstery, available from Steelcase, Grand Rapids, Mich. (not shown)). The table surfaces 25014 are covered with clean and unmarred sheets of flip chart paper (such as Expo Flip Chart 2.7"×34" paper (not shown)) in a single layer with ¼ inch overlap between adjacent sheets, such that the grading surface in the non-overlapping regions has an L*a*b* color as measured by a handheld spectrophotometer (such as a SpectroEye available from X-Rite Inc, Grand Rapids, Mich.) in a random sampling pattern where L* values lie between 82 and 92, a* values lie between 1.5 and 2.5, and b* values lie between −6 and −4. Further, the sheets have no areas of visibly different color to a person of normal color vision that are not included in the measurement sampling. The sheets are affixed to the table with ½" masking tape around the perimeter of the grading surface, but no masking tape is used between sheets, such that the grading surface is of uniform and uninterrupted color (with the exception of the ¼" overlap areas). The floor 25002 is carpeted with neutral colors, such that the L*a*b* color of all colors in the carpet have L* values that lie between 25 and 48, a* values that lie between −10 and 5, and b* values that lie between −5 and 12, as measured by a handheld spectrophotometer. The walls 25011 are painted with a non-reflective and low gloss paint with an L*a*b* color as measured by a handheld spectrophotometer such that the L* values lie between 85 and 92, the a* values lie between −2 and 0, and the b* values lie between 3 and 5. The ceiling 25001 is constructed of standard white drop ceiling panels.

On the table surfaces 25014, printed on sheets of standard 8.5 inch by 11 inch white paper (such as Main Street Copy Paper, 84 Bright, 20 pound) are the numbers 0 through 10 printed in 96 point bold Arial typeface, centered horizontally and vertically with one number per sheet in a landscape orientation (not shown). The sheets are lined up side by side with the shorter side of each sheet aligned with the shorter side of its neighbor(s) in increasing numerical order left to right, with the row of sheets centered horizontally and vertically on top of the flip chart sheets covering the table surfaces 25014 along the longer axis of the table. The sheets overlap each other by 3 inches, and no numbers are covered by neighboring sheets. All numbers are to be visible and upright to a viewer facing the one way mirrors 25013 and looking down at the table surfaces 25014. The row of papers are taped to the flip chart paper along its two longest edges with a single strip of ½ inch masking tape on each edge.

The ambient lighting in the room is measured with a light meter (such as a Flashmate L-308S available from Sekonic USA, Elmsford, N.Y.) placed flat on the table surface with the lumisphere facing the ceiling. The measurement mode is set to ambient EV, and measurements are taken at each intersection of an imaginary 6 inch by 6 inch grid across the grading surface. The lighting configuration is replaced or adjusted if the illuminance at any point is outside the range of 750 Lux to 910 Lux.

The stimuli for the seam noticeability grading consists of up to 10 test images, and a standard set of 20 control images.

Test images are pre-stacked in the assigned order prior to the consumer arriving for the seam noticeability grading. Upon arriving in the standardized grading room, consumers are shown an actual physical article comprising the seam of interest which is also represented in the test images. For example, a Size 4 Pampers Easy-Up could be used as the real article. Consumers are told that they will be grading images on a 0 to 10 scale for how noticeable the seam of interest is, and are shown the seam of interest on the real article. Consumers are then shown the first image in their assigned randomization, and shown the comparable parts between the image and the real article. The test administrator confirms that the consumer understands the task before proceeding. The consumer is instructed to sort and rate the images in the stack on the 0 to 10 scale where 0 is a seam that is not noticeable at all, and 10 is a seam that is extremely noticeable. Consumers are told to place the images under the number on the scale representing that image's rating, and that they can place as many or as few images under each number as they like. Consumers are encouraged to look through the stack of images, spread them out, adjust their ratings as they see new images, or proceed however they are most comfortable, letting the test administrator know when they are satisfied with the ratings. During the grading, the test administrator removes him or her self from the direct line of site of the consumer, and makes no comments, noises, gestures, nor otherwise indicates agreement, disagreement, or other knowledge of the grading order or process. When the consumer indicates completion, she is then thanked and dismissed, and the rating value for each of the images is recorded.

The "Seam Noticeability Rating" is the average rating taken over all consumers for a given image.

EXAMPLES

Example 1 (FIG. 19)

The disposable absorbent article in FIG. 19 has a front region; a back region and a crotch region between the front region and the back region. The chassis includes a liquid previous topsheet, a nonwoven outer cover or backsheet, a liquid impervious film associated with the topsheet, and an absorbent core disposed between the topsheet and the film.

The disposable absorbent article includes a pair of extensible front ear panels each extending laterally outward from the corresponding sides of the chassis in the front region, and a pair of extensible back ear panels each extending laterally outward from the corresponding sides of the chassis in the back region. The absorbent article includes seams each joining the front and back ear panels along the corresponding edge lines to for the two leg openings and the waist opening. The pairs of the ear panels are elastically extensible in the lateral direction. The ear panels are formed as unitary elements of the absorbent article and are secured to the nonwoven outer cover.

The absorbent article includes seam panels each extending laterally outward from each of the ear panels; and tear open tabs each extending laterally outward from the seam panel. The seam panels are an extension of the corresponding ear panels. The tear open tabs are also an extension of the corresponding seam panel. The corresponding edge portions of the ear panels are seamed directly in an overlapping manner to make an overlapped seam structure.

A continuous belt is formed by the ear panels, and a part of the chassis about the waist opening. The elasticized waist bands are provided in both the front region and the back region.

The nonwoven outer cover extends across the entire transverse direction of the article, overlapping both the ear panels and the absorbent core. The nonwoven outer cover creates a continuous surface on the outside of the article. The nonwoven outer cover contains graphics across a portion of the visible surface of the absorbent article. The graphics overlap both the ear panels and the absorbent core to create the appearance of a more holistic and garment-like article.

The absorbent article has graphics located on the visible surface of the topsheet. The topsheet graphics will only be visible when the article is not in use. The topsheet is partially suspended above the absorbent core in the crotch region to facilitate the contact between the wetness liner and the wearer in use. The graphics elements on the visible surface of the topsheet are actually located on the wetness liner directly below and in contact with the topsheet.

The topsheet has the body-facing surface of the absorbent article which is positioned adjacent to the wearer's body during use. The nonwoven outer cover has the outer-facing surface of the absorbent article which is positioned away from the wearer's body. The absorbent article includes the chassis including the liquid previous topsheet, the liquid impervious film associated with the topsheet, a nonwoven outer cover, and the absorbent core positioned between the topsheet and the impervious film. A wetness liner is positioned directly below the topsheet but is narrower in width. Elastic members in the topsheet provide the motive force to lift the topsheet and wetness liner away from the absorbent core in use. The absorbent article includes the front and back ear panels extending laterally outward from the chassis, the elasticized leg cuffs, and the elasticized waistbands. The topsheet and the backsheet have length and width dimensions larger than those of the absorbent core. The topsheet and the nonwoven outer cover extend beyond the edges of the absorbent core to thereby form the side edges and the waist edges of the absorbent article.

Each of the front ear panels is formed by a lamination of an extended part of the barrier flap, an elastic member and the nonwoven outer cover. The absorbent article has an asymmetric, modified hourglass-shaped absorbent core having ears in the front and back waist regions. The chassis includes an acquisition/distribution core of chemically stiffened fibers positioned over the absorbent core, thereby forming a dual core system.

The absorbent article includes an elasticized waistband that extends longitudinally outwardly from the waist edge of the absorbent article toward the waist edge of the absorbent core. The absorbent article has two elasticized waistbands, one positioned in the back region and one positioned in the front region. The waistbands contain materials that have been "prestrained."

The elastic member joined to both of the nonwoven webs and in the ear panels while in a substantially untensioned (zero strain) condition to allow the elastic member 70 to be elastically extensible in the lateral direction. After the elastic member is joined to at least one of the nonwoven webs, a portion of the resultant composite stretch laminate is then subjected to mechanical stretching sufficient to permanently elongate the non-elastic components which are the nonwoven webs. The composite stretch laminate is then allowed to return to its substantially untensioned condition.

Example 2 (FIG. 20)

Examples 2-4 are identical to Example 1, except that the nonwoven outer cover contains different graphics on the outer cover of the absorbent article.

Example 3

Fifty images for seam noticeability evaluation are shown to consumers according to the above Method for Generating a Seam Noticeability Rating (FIGS. 23-26, for example) are black and white representations of four images). The four classes of patterns for this example are: horizontal stripes, zig-zags, repeating clusters of circles, and repeating bears. The range for scale is 10 mm to 30 mm. The range for longitudinal spacing is 2 mm to 20 mm. The range for lateral spacing is 2 mm to 20 mm. And, the range for opacity is 25% to 100%. Further, stretch is defined as lateral scaling of the pattern in a right front side zone. The range for stretch is 0% to 50%.

The variable combinations of the example are determined by entering the seven variables (pattern, longitudinal spacing, lateral spacing, scale, contrast, longitudinal seam offset, lateral seam overlap, and stretch) as factors in a custom design DOE in MP v 6.0.3 (available from SAS Institute, Inc, Cary, N.C.). The software (JMP) creates the test matrix of variables and the corresponding values to investigate the design variables' impact on the noticeability of the seam. Pattern is entered as a 4-value categorical factor, all other variables are entered as continuous factors with the corresponding range values above. An additional 2-value categorical factor is added to represent consumer group two balanced groups of consumers grade separate sets of images to reduce the total number of stimuli any single consumer has to grade, thus avoiding respondent fatigue. $2^{nd}$ order interactions are added for all variables except consumer group with an Estimability value of if possible. The number of runs is set to 50, and the resulting design assigns 25 variable combinations to each consumer group. A random set of 5 variable combinations including at least one combination for each of the patterns from the set assigned to the first consumer group is also added to the second consumer group. A random set of 5 variable combinations including at least one combination for each of the patterns from the original set assigned to the second consumer group is also added to the first consumer group. Thus, each consumer from group one sees a set of 30 images including 10 images that consumers from group two see, and each consumer from group two sees a set of 30 images including 10 images that consumers from group one see. 20 consumers per consumer group are used for this test. The random variable combinations that are crossed between groups are selected by randomly sorting the variable combinations assigned to each consumer group a single time according to the above method for randomly sorting image identifiers, and then selecting the first 5 combinations in the list satisfying the criteria of including at least one combination for each pattern.

These variable combinations are tested according to the Method for Generating a Seam Noticeability Rating. The list of the design of experiments conditions and the results of the grading method are shown in Table 2. The randomization pattern for one group of consumers is shown in Table 3.

TABLE 2

| Image # | Pattern | Scale | Vertical Spacing | Horizontal Spacing | Vectical Offset | Horizontal Overlap | Contrast | Stretch | Avg Rating |
|---|---|---|---|---|---|---|---|---|---|
| 1 | bears | 10 | 10 | 10 | 15 | 7 | 60 | 0 | 5.15 |
| 2 | bears | 20 | 2 | 2 | 7 | 15 | 25 | 0 | 4.5 |
| 3 | bears | 20 | 10 | 20 | 7 | 15 | 100 | 0 | 6.8 |
| 4 | bears | 20 | 20 | 20 | 15 | 7 | 100 | 25 | 6.4 |
| 5 | bears | 30 | 10 | 20 | 0 | 7 | 25 | 25 | 4.4 |
| 6 | bears | 30 | 20 | 2 | 0 | 7 | 60 | 50 | 6.35 |
| 7 | bears | 10 | 2 | 2 | 0 | 0 | 60 | 50 | 3.6 |
| 8 | bears | 10 | 2 | 10 | 15 | 7 | 100 | 25 | 4.35 |
| 9 | bears | 10 | 10 | 10 | 7 | 15 | 60 | 50 | 5.95 |
| 10 | bears | 20 | 20 | 10 | 15 | 15 | 25 | 50 | 4.725 |
| 11 | bears | 20 | 20 | 20 | 0 | 0 | 25 | 25 | 4.95 |
| 12 | bears | 30 | 2 | 10 | 0 | 0 | 100 | 0 | 3.15 |
| 13 | bears | 30 | 10 | 2 | 7 | 0 | 100 | 25 | 7.35 |
| 14 | circles | 10 | 2 | 20 | 0 | 15 | 100 | 0 | 6.1 |
| 15 | circles | 10 | 10 | 20 | 0 | 15 | 25 | 25 | 4.9 |
| 16 | circles | 10 | 20 | 20 | 0 | 0 | 100 | 50 | 4.45 |
| 17 | circles | 20 | 2 | 10 | 7 | 0 | 100 | 25 | 5.95 |
| 18 | circles | 20 | 2 | 10 | 7 | 7 | 60 | 50 | 6.15 |
| 19 | circles | 20 | 20 | 2 | 7 | 7 | 60 | 25 | 6.2 |
| 20 | circles | 30 | 10 | 2 | 15 | 0 | 60 | 0 | 5.9 |
| 21 | circles | 10 | 2 | 2 | 15 | 0 | 25 | 0 | 5.2 |
| 22 | circles | 10 | 10 | 10 | 7 | 7 | 25 | 50 | 5.45 |
| 23 | circles | 20 | 10 | 2 | 0 | 15 | 25 | 50 | 5.6 |
| 24 | circles | 30 | 2 | 20 | 15 | 7 | 60 | 25 | 7.95 |
| 25 | circles | 30 | 20 | 10 | 0 | 15 | 60 | 0 | 7.25 |
| 26 | circles | 30 | 20 | 10 | 15 | 15 | 100 | 50 | 6.6 |
| 27 | stripes | 10 | 10 | 2 | 15 | 15 | 100 | 25 | 5.7 |
| 28 | stripes | 10 | 10 | 20 | 15 | 0 | 60 | 50 | 6.65 |
| 29 | stripes | 20 | 20 | 10 | 15 | 0 | 25 | 25 | 6.4 |
| 30 | stripes | 30 | 2 | 10 | 0 | 15 | 60 | 50 | 4.45 |
| 31 | stripes | 30 | 2 | 20 | 0 | 7 | 25 | 0 | 4.2 |
| 32 | stripes | 30 | 20 | 20 | 7 | 0 | 100 | 50 | 6.15 |
| 33 | stripes | 10 | 20 | 2 | 7 | 7 | 100 | 0 | 6.725 |
| 34 | stripes | 10 | 20 | 20 | 7 | 15 | 60 | 0 | 7.4 |
| 35 | stripes | 20 | 2 | 20 | 7 | 0 | 25 | 50 | 5.95 |
| 36 | stripes | 20 | 10 | 2 | 0 | 7 | 60 | 25 | 4.2 |
| 37 | stripes | 20 | 10 | 10 | 0 | 7 | 100 | 0 | 3.85 |
| 38 | stripes | 30 | 2 | 2 | 15 | 15 | 25 | 25 | 5.75 |
| 39 | zig-zag | 10 | 2 | 10 | 7 | 0 | 60 | 25 | 2.5 |
| 40 | zig-zag | 10 | 20 | 10 | 0 | 15 | 25 | 25 | 4.1 |
| 41 | zig-zag | 20 | 2 | 4 | 0 | 7 | 100 | 50 | 3.325 |
| 42 | zig-zag | 20 | 10 | 4 | 15 | 15 | 100 | 50 | 4.2 |
| 43 | zig-zag | 30 | 10 | 10 | 15 | 0 | 25 | 0 | 3.15 |
| 44 | zig-zag | 30 | 20 | 4 | 7 | 7 | 25 | 0 | 3.35 |
| 45 | zig-zag | 10 | 2 | 20 | 15 | 7 | 25 | 50 | 5.3 |
| 46 | zig-zag | 10 | 20 | 4 | 0 | 0 | 100 | 25 | 3.625 |
| 47 | zig-zag | 20 | 10 | 20 | 0 | 0 | 60 | 0 | 4.75 |
| 48 | zig-zag | 20 | 20 | 20 | 15 | 15 | 60 | 0 | 7.35 |
| 49 | zig-zag | 30 | 2 | 20 | 7 | 15 | 60 | 25 | 6.95 |
| 50 | zig-zag | 30 | 10 | 20 | 7 | 7 | 100 | 50 | 5.35 |

TABLE 3

| Panelist # | | | | | | | | | | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |
| 41 | 14 | 30 | 19 | 9 | 42 | 31 | 5 | 16 | 29 | 31 | 10 | 29 | 28 | 29 | 5 | 18 | 44 | 5 | 43 |
| 42 | 10 | 32 | 3 | 44 | 20 | 1 | 41 | 28 | 39 | 5 | 32 | 6 | 33 | 43 | 15 | 15 | 5 | 29 | 15 |
| 33 | 5 | 44 | 41 | 28 | 3 | 20 | 40 | 5 | 31 | 29 | 19 | 5 | 6 | 41 | 33 | 28 | 42 | 18 | 42 |
| 46 | 33 | 16 | 20 | 5 | 28 | 44 | 10 | 42 | 18 | 43 | 16 | 10 | 9 | 5 | 1 | 44 | 27 | 15 | 29 |
| 16 | 3 | 46 | 44 | 40 | 27 | 33 | 31 | 31 | 1 | 39 | 46 | 32 | 29 | 17 | 21 | 17 | 18 | 27 | 4 |
| 40 | 20 | 28 | 27 | 21 | 14 | 6 | 17 | 27 | 20 | 18 | 29 | 44 | 4 | 15 | 41 | 31 | 41 | 30 | 31 |
| 31 | 6 | 21 | 18 | 18 | 33 | 10 | 42 | 40 | 4 | 15 | 15 | 18 | 19 | 31 | 40 | 40 | 6 | 46 | 39 |

TABLE 3-continued

| | | | | | | | | | Panelist # | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 |
| 30 | 1 | 3 | 4 | 2 | 41 | 42 | 46 | 2 | 17 | 2 | 6 | 19 | 40 | 32 | 43 | 10 | 43 | 44 | 1 |
| 1 | 27 | 14 | 40 | 30 | 21 | 29 | 32 | 32 | 30 | 4 | 2 | 14 | 18 | 46 | 17 | 2 | 17 | 3 | 30 |
| 32 | 18 | 17 | 28 | 19 | 17 | 9 | 6 | 10 | 10 | 41 | 40 | 31 | 5 | 21 | 44 | 21 | 31 | 17 | 21 |
| 5 | 42 | 19 | 5 | 43 | 44 | 18 | 27 | 21 | 2 | 20 | 41 | 33 | 1 | 1 | 14 | 20 | 10 | 6 | 10 |
| 18 | 28 | 10 | 9 | 39 | 6 | 4 | 30 | 44 | 40 | 28 | 18 | 3 | 41 | 2 | 2 | 43 | 39 | 31 | 33 |
| 17 | 17 | 33 | 2 | 46 | 19 | 39 | 16 | 17 | 19 | 16 | 14 | 17 | 30 | 28 | 10 | 32 | 32 | 4 | 2 |
| 28 | 39 | 5 | 6 | 6 | 40 | 5 | 43 | 3 | 9 | 1 | 3 | 40 | 3 | 27 | 4 | 1 | 1 | 40 | 3 |
| 19 | 4 | 18 | 15 | 33 | 31 | 30 | 39 | 30 | 44 | 30 | 5 | 41 | 39 | 14 | 42 | 5 | 3 | 32 | 27 |
| 3 | 44 | 41 | 33 | 17 | 15 | 32 | 4 | 18 | 16 | 17 | 28 | 39 | 46 | 33 | 16 | 14 | 33 | 1 | 40 |
| 4 | 15 | 29 | 29 | 42 | 39 | 40 | 44 | 41 | 43 | 10 | 31 | 2 | 43 | 3 | 28 | 30 | 28 | 42 | 17 |
| 14 | 21 | 4 | 39 | 1 | 1 | 46 | 33 | 4 | 27 | 9 | 33 | 28 | 20 | 39 | 9 | 46 | 2 | 21 | 28 |
| 29 | 31 | 9 | 42 | 4 | 29 | 21 | 15 | 6 | 14 | 14 | 21 | 20 | 2 | 40 | 30 | 6 | 14 | 28 | 44 |
| 6 | 29 | 39 | 17 | 31 | 4 | 28 | 19 | 1 | 33 | 6 | 1 | 16 | 32 | 4 | 29 | 19 | 9 | 2 | 46 |
| 2 | 30 | 20 | 1 | 14 | 2 | 19 | 3 | 33 | 46 | 27 | 42 | 30 | 14 | 18 | 18 | 29 | 20 | 9 | 18 |
| 10 | 41 | 42 | 14 | 16 | 16 | 17 | 21 | 43 | 32 | 46 | 30 | 27 | 17 | 42 | 6 | 39 | 30 | 20 | 6 |
| 20 | 9 | 6 | 31 | 20 | 46 | 14 | 20 | 39 | 3 | 32 | 17 | 9 | 31 | 6 | 3 | 33 | 46 | 39 | 5 |
| 9 | 43 | 15 | 10 | 41 | 30 | 2 | 28 | 14 | 42 | 3 | 44 | 4 | 44 | 19 | 20 | 3 | 29 | 33 | 32 |
| 21 | 40 | 27 | 32 | 27 | 18 | 3 | 1 | 29 | 5 | 44 | 20 | 43 | 15 | 20 | 46 | 9 | 15 | 14 | 41 |
| 44 | 32 | 43 | 30 | 10 | 32 | 27 | 14 | 20 | 41 | 19 | 27 | 42 | 27 | 16 | 31 | 27 | 21 | 10 | 20 |
| 43 | 46 | 1 | 46 | 32 | 43 | 16 | 29 | 15 | 6 | 21 | 43 | 15 | 21 | 30 | 27 | 16 | 4 | 16 | 19 |
| 39 | 19 | 2 | 16 | 29 | 10 | 15 | 2 | 46 | 15 | 40 | 4 | 1 | 10 | 9 | 39 | 4 | 16 | 19 | 16 |
| 15 | 2 | 40 | 21 | 3 | 5 | 43 | 9 | 19 | 28 | 42 | 9 | 21 | 42 | 44 | 19 | 42 | 40 | 41 | 14 |
| 27 | 16 | 31 | 43 | 15 | 9 | 41 | 18 | 9 | 21 | 33 | 39 | 46 | 16 | 10 | 32 | 41 | 19 | 43 | 9 |

After the seam noticeability grading test, the consumers are asked at what point on the 0 to 10 scale the noticeability of the seam negatively impacts their perception of the quality of the article. The average response in this example is 6.28.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of constructing a pull-on disposable absorbent article having a first waist region, a second waist region, and a crotch region disposed therebetween, the method comprising:
   attaching a first side panel to the first waist region such that a first seam is formed;
   attaching a second side panel to the first waist region such that a second seam is formed;
   attaching a third side panel to the second waist region such that a third seam is formed;
   attaching a fourth side panel to the second waist region such that a fourth seam is formed;
   attaching the first side panel to the third side panel such that a fifth seam is formed and a first leg opening is formed;
   attaching the second side panel to the fourth side panel such that a sixth seam is formed and a second leg opening and a waist opening is formed and such that the disposable absorbent article is in a pull-on configuration;
   stretching a web material used to form the first side panel such that the web material is in a stretched state;
   printing a first graphic object on the web material used to form the first side panel when the web material is in the stretched state;
   stretching the web material used to form the second side panel such that the web material is in a stretched state;
   printing a second graphic object on the web material used to form the second side panel when the web material is in the stretched state;
   stretching the web material used to form the third side panel such that the web material is in a stretched state;
   printing a third graphic object on the web material used to form the third side panel when the web material is in the stretched state;
   stretching the web material used to form the fourth side panel such that the web material is in a stretched state;
   printing a fourth graphic object on the web material used to form the fourth side panel when the web material is in the stretched state;
   printing a fifth graphic object on the backsheet; and
   printing a sixth graphic object on the backsheet.

2. The method of claim 1, wherein the first waist region is the front waist region.

3. The method of claim 1, further comprising a registering step performed using a beam radiation system.

4. The method of claim 3, wherein the registering step is performed by at least two vision capture devices.

5. The method of claim 4, wherein the at least two vision capture devices are placed opposite each other.

6. The method of claim 1, wherein a left side zone of the absorbent article comprises at least two seams.

7. The method of claim 1, wherein a right side zone of the absorbent article comprises at least three seams.

8. The method of claim 1, wherein fifth graphic object is printed on a film.

9. The method of claim 8, wherein the third and fourth side panels are disposed in the second waist region.

10. The method of claim 1, wherein each of the side panels have similar elastic properties.

11. The method of claim 1, wherein the pull-on disposable absorbent article comprises active graphics.

12. The method of claim 11, wherein the active graphics are capable of disappearing when wetted.

13. The method of claim 1, wherein the pull-on disposable absorbent article comprises a sensor.

14. The method of claim 1, wherein the fifth and sixth seams comprise refastenable fasteners.

15. The method of claim 1, wherein the web material comprises a plane elastomeric material, wherein the plane elastomeric material is an apertured film.

16. The method of claim 1, wherein the first and second seams have a Seam Noticeability Rating of less than about 4.

17. The method of claim 1, wherein the first and second seams have a Seam Noticeability Rating of less than about 5.

18. The method of claim 1, wherein multiple graphic objects in the first and second waist regions cooperate to form the appearance of a waistband.

19. The method of claim 1, wherein the pull-on disposable absorbent article comprises a wetness indicator.

20. The method of claim 1, wherein a position of at least one graphic object is controlled via a controlling process.

21. The method of claim 20, wherein the controlling process involves the use of a machine vision system.

22. The method of claim 1, wherein the first side panel is overlapped with and attached to the third side panel to form a refastenable fifth seam.

23. The method of claim 22, wherein the first graphic object is disposed immediately adjacent to the refastenable fifth seam.

24. The method of claim 22, wherein the third graphic object is disposed immediately adjacent to the refastenable fifth seam.

25. The method of claim 1, wherein the second side panel is overlapped with and attached to the fourth side panel to form a refastenable sixth seam.

26. The method of claim 25, wherein the second graphic object is disposed immediately adjacent to the refastenable sixth seam.

27. The method of claim 25, wherein the fourth graphic object is disposed immediately adjacent to the refastenable sixth seam.

28. The method of claim 1, wherein the web material comprises an elastomeric material joined to a nonwoven.

* * * * *